(12) United States Patent
Lin et al.

(10) Patent No.: US 12,226,477 B2
(45) Date of Patent: Feb. 18, 2025

(54) METHODS FOR PREPARING COMPLEX FOR ENHANCING IMMUNE RESPONSE

(71) Applicant: XINFU (BEIJING) MEDICAL TECHNOLOGY CO., LTD., Beijing (CN)

(72) Inventors: Haixiang Lin, Beijing (CN); Fang Liu, Beijing (CN); Li Zha, Beijing (CN)

(73) Assignee: BEIJING YISHENG BIOTECHNOLOGY CO., LTD., Beijing (CN)

( * ) Notice: Subject to any disclaimer, the term of this patent is extended or adjusted under 35 U.S.C. 154(b) by 1086 days.

(21) Appl. No.: 17/256,980

(22) PCT Filed: Jun. 28, 2019

(86) PCT No.: PCT/CN2019/093607
§ 371 (c)(1),
(2) Date: Mar. 31, 2021

(87) PCT Pub. No.: WO2020/001596
PCT Pub. Date: Jan. 2, 2020

(65) Prior Publication Data
US 2023/0210893 A1    Jul. 6, 2023
US 2024/0316189 A9    Sep. 26, 2024

(30) Foreign Application Priority Data

Jun. 29, 2018  (CN) .......................... 201810698033.6
Jun. 29, 2018  (CN) .......................... 201810700708.6

(51) Int. Cl.
*A61K 39/39* (2006.01)
*A61K 31/787* (2006.01)
*A61K 45/06* (2006.01)
*A61K 47/02* (2006.01)
*A61K 47/26* (2006.01)
*A61K 47/36* (2006.01)
*A61K 39/00* (2006.01)

(52) U.S. Cl.
CPC ............ *A61K 39/39* (2013.01); *A61K 31/787* (2013.01); *A61K 45/06* (2013.01); *A61K 47/02* (2013.01); *A61K 47/26* (2013.01); *A61K 47/36* (2013.01); *A61K 2039/55555* (2013.01); *A61K 2039/55561* (2013.01)

(58) Field of Classification Search
CPC ....... A61K 31/787; A61K 47/26; A61K 47/36
See application file for complete search history.

(56) References Cited

U.S. PATENT DOCUMENTS

| | | | | |
|---|---|---|---|---|
| 9,682,096 B2* | 6/2017 | Baert | .......... | A61K 9/16 |
| 2008/0095810 A1 | 4/2008 | Fernandez et al. | | |
| 2011/0118200 A1 | 5/2011 | Fugiang et al. | | |
| 2016/0312224 A1* | 10/2016 | Rohayem | .......... | C12P 19/34 |
| 2017/0281754 A1 | 10/2017 | Dow et al. | | |
| 2018/0360738 A1 | 12/2018 | Lin et al. | | |
| 2019/0328767 A1 | 10/2019 | Ye | | |

FOREIGN PATENT DOCUMENTS

| | | | |
|---|---|---|---|
| CA | 3105281 A1 | | 1/2020 |
| CN | 1095951 A | | 12/1994 |
| CN | 1997391 A | | 7/2007 |
| CN | 101134014 A | | 9/2007 |
| CN | 101124014 A | | 2/2008 |
| CN | 101166559 A | | 4/2008 |
| CN | 102318740 A | | 1/2012 |
| CN | 103405762 A | | 11/2013 |
| CN | 103599071 A | * | 2/2014 |
| CN | 104434784 A | | 3/2015 |
| CN | 105396130 A | | 3/2016 |
| CN | 106075431 A | | 11/2016 |
| CN | 107184973 A | | 9/2017 |
| CN | 108743938 A | | 11/2018 |

(Continued)

OTHER PUBLICATIONS

Machine translation of CN-103599071-A, 2014, pp. 1-6 (Year: 2014).*
ChitoLytic (https://chitolytic.com/chitosan-products/chitosan-oligosaccharide-mushroom/#:~:text=Chitosan%20oligosaccharide%20(COS)%20is%20an,D%2Dglucopyranose%20(GlcN)), accessed May 1, 2024 (Year: 2024).*
Abstract of "polyI:C anti-tumor and immunomodulatory effects", dated Oct. 3, 1991, China Academic Journal Electronic Publishing House, pp. 173-176.
International Search Report for PCT/CN2019/093558, dated Sep. 16, 2019, 9 pages including English translation.

(Continued)

*Primary Examiner* — Andrew S Rosenthal
(74) *Attorney, Agent, or Firm* — Quarles & Brady LLP

(57) ABSTRACT

A novel composite, and research on the preparation, application and the like of the composite. The method for preparing the composite comprises: contacting a polyinosinic-polycytidylic acid, at least one cationic stabilizer, and a soluble calcium salt in a liquid reaction system, the cationic stabilizer being a water-soluble non-antibiotic amino compound having a molecular weight of less than or equal to 5 kDa, or a graft copolymer formed by a water-soluble non-antibiotic amino compound and one or more of methoxypolyethylene glycol, polyethylene glycol, polyethylenimine, folic acid, or galactose. The composite has moderate viscosity and molecular weight, is convenient to use in pharmaceutical application, has stable chemical properties, is not easy to be degraded in long-term storage, and is safe to use. The composite, if used alone, can significantly enhance the non-specific immune response of the body and achieve the purpose of preventing and treating diseases, and other drugs, and can achieve better anti-tumor, anti-viral and anti-(super) bacteria efficacy and is easily absorbed by patients, if used in combination with other drugs.

18 Claims, 21 Drawing Sheets

(56) References Cited

FOREIGN PATENT DOCUMENTS

| CN | 109078180 A | 12/2018 |
|---|---|---|
| CN | 109125264 A | 1/2019 |
| IN | 6563DELP2008 | 10/2008 |
| RU | 2383552 C2 | 3/2010 |
| RU | 2647366 C1 | 3/2018 |
| WO | WO 2006/131023 | 12/2006 |
| WO | WO 2007/081287 | 7/2007 |
| WO | WO 2017080098 A | 5/2017 |
| WO | WO 2017161950 A1 | 9/2017 |

OTHER PUBLICATIONS

Office Action for CN application 201810698033.6, dated Dec. 14, 2018, 7 pages (in Chinese).
Office Action for CN 201810698033.6, dated Feb. 11, 2019, 3 pages (in Chinese).
Office Action for CN 201810700708.6, dated Feb. 22, 2019, 13 pages (in Chinese).
Reed et al., "Immune status of PIC Camborough-15 sows, 25% Meishan sows, and their offspring kept indoors and outdoors", Journal of Animal Science, 2000, 78:2561-2567.
Correia-Pinto, et al.; "Chitosan-Poly(I:C)-PADRE Based Nanoparticles as Delivery Vehicles for Synthetic Peptide Vaccines," Vaccines; vol. 3, No. 3; Jan. 1, 2015, pp. 730-750.
Lin, et al.; "Equally Knocking on the Door of Medical Breakthroughs: Safety and Efficacy of a New Anti-Cancer Drug Pamica (PICNH2Ca) for Late Stage Cancer Patients," Journal of Biosciences and Medicines; vol. 5; Feb. 22, 2017; pp. 49-54.
Liu, et al.; "Synergy effects of Polyinosinic-polycytidylic acid, CpG oligodeoxynucleotide, and cationic peptides to adjuvant HPV E7 epitope vaccine through preventive and therapeutic immunization in a TC-1 grafted mouse model," Human Vaccines and Immunotherapeutics; vol. 14, No. 4; Apr. 3, 2018; pp. 931-940.
Supplementary European Search Report for EP 19825645, dated Apr. 4, 2022, 9 pages.
Wu, et al.; "Anti-tumor outcome evaluation against non-small cell lung cancer in vitro and in vivo using PolyI:C as nucleic acid therapeutic agent," Am J Transl Res, Apr. 15, 2019, pp. 1919-1937.
Hafner, et al. "Particulate formulations for the delivery of poly(I:C) as vaccine adjuvant", Advanced Drug Delivery Reviews ; 65 (2013) pp. 1386-1399.
Zhang, et al. "The positive correlation of the enhanced immune response to PCV2 Subunit Vaccine by conjugation of chitosan oligosaccharide with the deacetylation degree", Marine Drugs; (2017) 15:236, pp. 1-14.
Office Action for CA application 3,105,283, dated Jan. 21, 2022, 5 pages.
Office Action for JP application 2020-573468, dated Mar. 14, 2022, 9 pages including English translation.
Bulletin of Applied Glycoscience, 2014, vol. 4, No. 2, pp. 127-132 (w/ English Abstract).
Kavaliauskis, et al. "Use of Poly(I:C) Stabilized with Chitosan As a Vaccine-Adjuvant Against Viral Hemorrhagic Septicemia Virus Infection in Zebrafish," Zebrafish, 2015, vol. 12, No. 6, pp. 1-11.
Dai, X., et al., Co-delivery of polyinosinic:polycytidylic acid and flagellin by poly(lactic-co-glycolic acid) MPs synergistically enhances immune response elicited by intranasally delivered hepatitis B surface antigen, Int'l Jour. of Nanomedicine vol. 12, pp. 6617-6632.
European Search Report for EP 19825644 dated Mar. 3, 2022, 9 pages.
Office Action mailed Aug. 2, 2022 with respect to Russian App. No. 2021101242, 28 pages w/ Eng. Machine Translation.
Office Action mailed Jan. 21, 2022 with respect to Canadian App. No. 3,105,281, 6 pages.
Office Action mailed Mar. 28, 2022 with respect to Japanese App. No. 2020-573491, 7 pages w/ English Summary.
Office Action of IN Application No. 202147003616 dated Apr. 30, 2021, 8 pages.
Wan, J. et al. "New insights into the role of chitosan oligosaccharide in enhancing growth performance, antioxidant capacity, immunity and intestinal development of weaned pigs", (2017) RSC Advances, vol. 7, pp. 9669-9679.
Office action mailed Feb. 21, 2024, with respect to U.S. Appl. No. 17/256,979.

\* cited by examiner

METHODS FOR PREPARING COMPLEX FOR ENHANCING IMMUNE RESPONSE

CROSS-REFERENCE TO RELATED APPLICATION

This application is a national stage application for International application PCT/CN2019/093607, filed Jun. 28, 2019 entitled "METHOD FOR PREPARING COMPOSITE FOR ENHANCING IMMUNE RESPONSE" which application claims priority of Chinese Patent Application No. 201810698033.6, filed 29 Jun. 2018 to the China Patent Office and entitled "METHOD FOR PREPARING COMPLEXES FOR POTENTIATING AN IMMUNE RESPONSE", and of Chinese Patent Application No. 201810700708.6, filed 29 Jun. 2018 to the China Patent Office and entitled "COMPLEXES FOR POTENTIATING AN IMMUNE RESPONSE", the entire contents of which are incorporated by reference herein in their entirety.

TECHNICAL FIELD

The present disclosure relates to the biomedicine field and in particular to a method for preparing a complex for potentiating an immune response.

BACKGROUND

Double-stranded RNA (dsRNA) adjuvants, which are currently and generally considered to include PIC (polyriboinosinic-polyribocytoidylic acid), PICLC (PIC with poly-L-lysine and carboxymethyl cellulose), $PIC_{12}U$ (PIC with uridylic acid in specific interval, trade name of Ampligen), and PICKCa (PIC-kanamycin-$CaCl_2$), are ligands for a variety of pattern recognition receptors (PRRs), and are possible, on the one hand, by potentiating the immune response and, on the other hand, by changing the types of immunity, to make prophylactic vaccines to be therapeutic vaccines.

PIC (polyinosinic-polycytidylic acid) was developed by Merck (U.S.) in the 1960s. In mice, PIC is an IFN-α inducer with anti-viral activity. PIC may protect mice from lethal infections in the nasal cavity and lungs. However, due to the degradation of PIC by serum nucleases of primates and human, PIC has a reduced structure stability, with few IFN-α produced and without anti-tumor activity.

PICLC (polyinosinic-polycytidylic acid with poly-L-lysine and carboxymethyl cellulose), a conjugate of PIC, polylysine (Poly L-lysine, relative molecular weight of 27,000) and carboxymethyl cellulose (CMC, relative molecular weight of 700,000) which was developed by Levy HB in the 1970s, has a larger relative molecular weight and a resistance to hydrolysis by the nucleases that is 5-10 times greater than PIC, and produces significant interferon (15) in monkeys. Preliminary clinical studies on PICLC showed that a moderate-to-severe response, such as fever (100%), myalgia (50%), hypotension (50%), significant decline in white blood cell, and the like may be caused just at a therapeutic dose. This leads to a misunderstanding that a larger molecular weight leads to a greater toxicity.

$PIC_{12}U$, in which uracil nucleotides are inserted at a position in the PIC strand, was developed by Johns Hopkins University in the mid-1970s, and has potency similar to that of PIC, but less toxicity. In August 2012, Hemispherx Biopharmaceutical Company submitted further original clinical research data; however, $PIC_{12}U$ was not approved by the U.S. Food and Drug Administration (FDA) due to insufficient safety and efficacy data.

PICKCa contains an antibiotic, i.e. kanamycin. Kanamycin has moderate ototoxicity, and has an amount present in the vaccine that exceeds the standard set by the national pharmacopoeia.

It can be seen that, PIC alone cannot be used in primates and more advanced animals than primates, including humans, $PIC_{12}U$ has not been approved by the U.S. FDA due to its poor effect, and PICLC actually has strong side effects.

In view of this, the present disclosure is hereby presented.

SUMMARY

The present disclosure relates to a novel complex, and the preparation, use and the like of the complex has been studied.

In the inventor's previous work, PIC, kanamycin, and calcium chloride were used to prepare vaccine adjuvants (trade name: PIKA adjuvant). Kanamycin is used due to the fact that it contains 4 amino groups that will bind to a phosphate group in the PIC to stabilize structure thereof. However, the application of the product in vaccines is limited due to the inclusion of the antibiotic.

Furthermore, the inventors found that replacing kanamycin with chitosan (hydrochloride) can also act as a cationic stabilizer, however, chitosan (hydrochloride) has a large molecular weight and is not easily absorbed by human, thus it is difficult to obtain a desired efficacy.

Therefore, the present disclosure provides a complex for potentiating an immune response. The complex is prepared by at least the following components under a suitable condition: a polyinosinic-polycytidylic acid, at least a cationic stabilizer and a soluble calcium salt.

The complex is prepared by at least the following components under a suitable condition: a polyinosinic-polycytidylic acid, at least a cationic stabilizer, a soluble calcium salt or/and a manganese salt.

Wherein, the cationic stabilizer is a water-soluble non-antibiotic amino compound having a molecular weight of less than or equal to 5 kDa, or a graft formed by the water-soluble non-antibiotic amino compound and one or more of methoxypolyethylene glycol, polyethylene glycol, polyethylenimine, folic acid and galactose.

Compared with the prior art, the complex has a moderate viscosity and a molecular weight, easily prepared into a drug, and has stable chemical properties, being difficult to be degraded in long-term storage and safe to use. The complex can significantly potentiate the non-specific immune response in the body and achieve the purpose of preventing and treating a disease when is used alone, and can achieve better anti-tumor, anti-viral and anti-(super) bacteria efficacy and is easily absorbed by a patient when is used in combination with other drugs.

BRIEF DESCRIPTION OF THE DRAWINGS

To illustrate the technical solutions according to the embodiments of the present invention or in the prior art more clearly, the accompanying drawings for describing the embodiments or the prior art are introduced briefly in the following. Apparently, the accompanying drawings in the following description are only some embodiments of the present invention, and persons of ordinary skill in the art can derive other drawings from the accompanying drawings without creative efforts.

FIG. 18: The curves of tumor volume changes under the treatments with different drugs.

FIG. 19: Tumor weight under the treatments with different drugs (the vehicle control group has a tumor volume of 2201.09±68.01 $mm^3$ on the $14^{th}$ day after administration, and the experiment ended on the $14^{th}$ day after administration).

FIG. 20: A: vehicle control, by nasal drip, once every two days; B: cisplatin (5 mg/kg), by tail vein injection, once a week; C: Pamica-1 (i.e. Pamica), 200 μg/mouse, by nasal drip, once every two days; D: Pamica-1, 200 μg/mouse, by nasal drip (administered immediately after inoculation), once every two days; E: Pamica-1, 150 μg/mouse, by nasal drip, once every two days; F: Pamica-1, 200 μg/mouse, by intramuscular injection, once every two days; G: Pamica-1+cisplatin, 200 μg/mouse+5 mg/kg, by nasal drip+by tail vein injection, once every two days+once a week; scale bar=1 cm.

FIG. 21: The tumor inhibition rate of murine PD-1 antibody.

FIG. 22: The curves of tumor volume changes.

FIG. 23: The curves of the body weight changes of mice.

FIG. 24: The effects of treatments with different drugs on tumor weight.

FIG. 25: A photo of tumors under the influence of different drugs.

FIG. 26: The effects of treatments with different drugs on spleen weight.

FIG. 27: A photo of the front of the lungs under the influence of different drugs.

FIG. 28: A photo of the back of the lungs under the influence of different drugs.

FIGS. 29~35: The photos of the site of a tumor and bioluminescence intensity of metastasis displayed by the small-animal imager.

FIG. 29: The bioluminescences of mice in the Pamica 7-day advanced group.

FIG. 30: The bioluminescences of mice in the Pamica 0-day group.

FIG. 31: The bioluminescences of mice in the vehicle group.

FIG. 32: The bioluminescences of mice in the 200 μg/mouse Pamica nasal drip group.

FIG. 33: The bioluminescences of mice in the 300 μg/mouse Pamica nasal drip group.

FIG. 34: The bioluminescences of mice in the 200 μg/mouse Pamica intramuscular injection group.

FIG. 35: The bioluminescences of mice in the 300 μg/mouse Pamica intramuscular injection group.

DETAILED DESCRIPTION OF THE EMBODIMENTS

Figure 1:
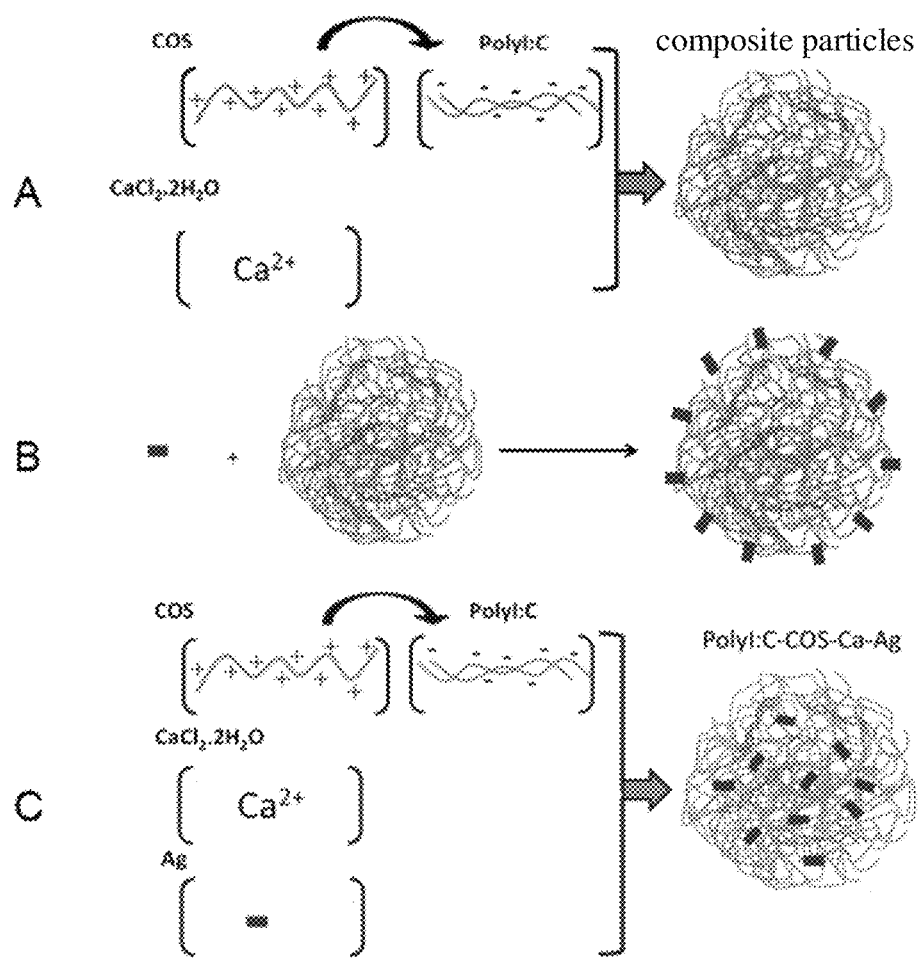
FIG. 1 is a schematic diagram of the structure of the Pamica complex; A: a schematic diagram of the structure of a Poly I: C-COS-$Ca^{2+}$ complex; B: a schematic diagram of the structum of an antigen (Ag)+complex particle; C: a schematic diagram of the structure of a Poly I: C-COS-$Ca^{2+}$+Ag complex.

The present disclosure can become more apparent through the following description of some embodiments thereof and the detailed contents of the examples included therein.

Before further describing the present disclosure, it should be understood that the present disclosure is not limited to the specific embodiments, because these embodiments are necessarily diverse. It should also be understood that the terms used in this specification are only to illustrate specific embodiments, rather than to provide as limitation, because the scope of the present disclosure will only be defined in the appended claims.

Term Definition

Before stating the details of the present disclosure, several terms used in the present specification should be understood.

The term "Pamica" generally refers to a complex prepared from a polyinosinic-polycytidylic acid, a cationic stabilizer and a soluble calcium salt (calcium ions), regardless of the specific physical property and immunogenicity of the complex.

"Polyinosinic-polycytidylic acid" is also known as poly inosine-cytidine, polyinosinic acid polycytidylic acid, polyinosinic acid cytosine nucleotide, polyinosinic acid-polycytidylic acid, PIC or Poly I:C.

As used in the present specification, the term "potentiating an immunoreaction" refers to inducing or potentiating an immune response to an antigenic substance in a host, or potentiating the function of immune cells, or promoting the release of inflammatory factors or cytokines from immune cells, or enhancing the resistance to a pathogenic substance in a host.

The term "inducing an immune response" refers to stimulating, initiating or developing an immune response.

"Potentiating an immune response" refers to the improvement, development, supplement, expansion, increase, and extension of an existing immune response.

The expression "potentiating an immune response" or similar expressions means that, compared with the previous immune response state, the immune response is enhanced, improved or increased, which is beneficial to the host. The previous immune response state, for example, is the state of the previous immune response before the immunogenic composition of the present disclosure is administered.

The term "individual" is used herein interchangeably with "host", "subject" and "animal", and includes humans and all livestocks (such as domestic animals and pets) and wild animals and birds, including, without limitation, cattle, horse, dairy cow, pig, sheep, goat, rat, mouse, dog, cat, rabbit, camel, donkey, deer, mink, chicken, duck, goose, turkey, cockfight, etc.

The term "antibody" includes polyclonal antibodies and monoclonal antibodies as well as the antigen compound binding fragments of these antibodies, including Fab, $F(ab')_2$, Fd, Fv, scFv, bispecific antibodies and the minimum recognition unit of antibodies, as well as single-chain derivatives of these antibodies and fragments. The type of antibody can be selected from IgG1, IgG2, IgG3, IgG4, IgA, IgM, IgE, and IgD. In addition, the term "antibody" includes naturally-occurring antibodies and non-naturally-occurring antibodies, including, for example, chimeric, bifunctional and humanized antibodies, and related synthetic isoforms. The term "antibody" can be used interchangeably with "immunoglobulin".

As used in the present specification, the term "antigen compound" refers to any substances that can be recognized by the immune system (for example, bound to an antibody or processed to induce a cellular immune response) under appropriate circumstances.

As used in the present specification, "antigen" includes, but is not limited to, cells, cell extracts, proteins, lipoproteins, glycoproteins, nucleoproteins, polypeptides, peptides, polysaccharides, polysaccharide conjugates, peptide mimics of polysaccharides, fats, glycolipids, saccharides, viruses, viral extracts, *bacterium*, bacterial extracts, fungi, fungal extracts, multicellular organisms such as parasites, and allergens. Antigens may be exogenous (for example, from an other source except the individual to whom the antigen is administered, for example, from a different species) or endogenous (for example, from the host body, such as disease factors, cancer antigens, antigens produced by cells being infected with viruses in the body, etc.). Antigens may be natural (for example, naturally occurring), synthetic or recombinant. Antigens include cell extracts, intact cells, and purified antigens, wherein, the term "purified" means that the antigen is presented in a more enriched form compared to that in the environment in which the antigen usually exists and/or compared to that in a form of crude extract (such as the form of antigen culture).

The term "vaccine composition" as used in the present specification refers to a combination of two or more substances (such as antigens and adjuvants), which will jointly stimulate an immune response, when administered to a host.

The terms "polypeptide", "peptide", "oligopeptide" and "protein", and the like, are used interchangeably in the present specification and mean the polymer form of amino acids having any length. The polymer form may include encoded and non-encoded amino acids, chemically or biochemically modified or derived amino acids and polypeptides having a modified peptide backbone.

The term "immune response" refers to any responses of the immune system of a vertebrate individual to an antigenic or immunogenic compound. Typical immune responses include, but are not limited to, local and systemic cellular and humoral immune responses, such as cytotoxic T lymphocyte (CTL) responses including antigen-specific induction of CD8+CTLs, helper T-cell responses including T-cell proliferation responses and cytokines releases, and B-cell immune responses including antibody responses.

The term "adjuvant" as used herein refers to any substance or mixture of substances that increase or change the immune response to an antigen compound in a host.

The term "treatment" used in the present specification generally refers to the achievement of the desired pharmacological and/or physiological efficacy. The efficacy may be of a preventive nature from the perspective of completely and/or partially preventing diseases or the symptoms thereof, and/or the effects may be of a medical nature from the perspective of completely and/or partially stabilizing or curing diseases and/or the negative effects caused by the diseases. The term "treatment" used in the present specification covers any treatments of diseases in an individual (especially a mammalian individual, and more particularly human), and include: (a) preventing the individual that may be predisposed to a disease but have not yet been diagnosed from developing the disease or a symptom thereof, (b) inhibiting the symptom of disease, for example, preventing the development of the symptom of disease; or relieving the symptom of disease, such as causing the disease or symptoms to subside; (c) reducing the level of products produced by the infectious substance of disease (such as toxins, antigens, etc.); (d) reducing adverse physiological reactions (such as fever, tissue edema, etc.) by infectious substances of disease.

The chemical substance of "pharmaceutically acceptable salt" means that the salt is pharmaceutically acceptable and possesses the desired pharmacological activity of the parent compound. These salts include: (1) salts formed together from inorganic acids that synthesize salts, such as hydrochloric acid, hydrobromic acid, sulfuric acid, nitric acid, phosphoric acid, etc.; or salts formed together with organic acids and the like such as acetic acid, propionic acid, caproic acid, cyclopentapropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4, 4'-methylenebis (3-hydroxy-2-ene-1-carboxylic acid), 3-phenylpropionic acid, trimethylacetic acid, tertiary butyl lactic acid, lauryl sulfuric acid, gluconic acid, glutamic acid, hydroxynaphthoic acid, salicylic acid, stearic acid, muconic acid, etc.; or (2) salts formed, when the acidic protons present in the parent compound are replaced by metal ions such as metal ions of alkali group, metal ions of alkaline earth group or aluminum ions, or coordinated with organic compounds such as ethanolamine, diethanolamine, triethanolamine, tromethamine, N-methylglucamine, and the like.

Exemplary Embodiments of the Present Disclosure

An aspect of the present disclosure relates to a combination product for potentiating an immune response, comprising a polyinosinic-polycytidylic acid, at least a cationic stabilizer, and a soluble calcium salt; The cationic stabilizer is a water-soluble non-antibiotic amino compound having a molecular weight of less than or equal to 5 kDa, or a graft formed by the water-soluble non-antibiotic amino compound, and one or more of methoxypolyethylene glycol, polyethylene glycol, polyethylenimine, folic acid and galactose.

An important advantage lies on that Pamica used alone can significantly potentiate the non-specific immune response in a body, and can more effectively initiate a specific humoral immune response and cellular immune response, enhancing protective immunity; better effects can be achieved when used in combination with an antigen substance.

An important advantage lies on that Pamica can pass "1141 Abnormal Toxicity Test", PHARMACOPOEIA OF THE PEOPLE'S REPUBLIC OF CHINA, the 4$^{th}$ vol., 2015, and can be safely applied into the human body. Complexes (such as PIC-amino compound-CaCl$_2$ adjuvant or PIC-amino compound-CaCl$_2$ adjuvant vaccine) prepared with PIC having a molecular weight that has not been treated by heating cannot pass the abnormal toxicity test.

An important advantage lies on that Pamica has better chemical and/or physical stability, thus makes it easier to store.

An important advantage lies on that Pamica can promote tumor cell apoptosis through a signaling pathway, and can also stimulate immune cells to express a variety of cytokines and change a microenvironment in which the tumor cells are present, allowing immune cells to attack pathogenic substances, such as tumor cells, viruses, *bacterium* and the like.

An important advantage lies on that Pamica is more easily absorbed by a host or swallowed by a host cell, which in turn, may further bring more antigens into cells, thereby potentiating the immune responses caused by proteins and peptides.

An important advantage lies on that Pamica has obvious analgesic effect for a patient with cancer pain.

An important advantage lies on that Pamica can turn the virus titer of HPV infected people from strong positive to negative.

An important advantage lies on that the Pamica plus *Bacterium burgeri* inactivated vaccine has a good protective effect.

It should be noted that Pamica, as described in the present disclosure, is a complex having a completely new structure rather than a simple composition.

In some embodiments, the cationic stabilizer has a molecular weight that may further be selected from 4 kDa, 4.5 kDa, 3 kDa, 3.5 kDa, 2.5 kDa, 2 kDa, 1.5 kDa, 1 kDa, 500 Da, 400 Da, 300 Da, 200 Da and 100 Da.

In some embodiments, the water-soluble non-antibiotic amino compound is one or more selected from the group consisting of chitosan oligosaccharides, chitooligosaccharides, glucosamines, cationic liposomes, DEAE-dextran, polyacrylamide, polyamines, tetraaminofulvene, and polyethyleneimine.

In some embodiments, the cationic stabilizer is selected from the group consisting of a graft (COS-g-MPEG) of chitosan oligosaccharide and methoxypolyethylene glycol, a graft (PEG-g-CS) of chitosan hydrochloride and polyethylene glycol, a graft (FA-g-CS) of folic acid and chitosan hydrochloride, a graft (GAL-g-PEG-g-PEI) of galactose, polyethylene glycol and polyethyleneimine, a graft (COS-g-MPEG-g-PEI) of chitosan and methoxypolyethylene glycol and polyethyleneimine, a graft (CS-g-PEG-g-PEI) of chitosan, methoxypolyethylene glycol and polyethyleneimine, a graft (PEI-g-PEG) of polyethylene glycol and polyethyleneimine, a graft (PEI-g-COS) of chitosan oligosaccharide and polyethyleneimine, a graft (PEI-g-CS) of chitosan hydrochloride and polyethyleneimine, a graft (COS-g-PEG) of chitosan oligosaccharide and polyethylene glycol, and a graft (COS-g-PEG-g-PEI) of chitosan oligosaccharide, polyethylene glycol and polyethyleneimine.

In some embodiments, the cationic stabilizer is selected from the group consisting of a chitosan oligosaccharide (COS), a graft (COS-g-MPEG) of chitosan oligosaccharide and methoxypolyethylene glycol, a graft (COS-g-MPEG-g-PEI) of chitosan oligosaccharide, methoxypolyethylene glycol and polyethyleneimine.

In some embodiments, the graft has molecular weight of less than or equal to 50 kDa.

In some embodiments, the molecular weight of the cationic stabilizer may be further selected from 45 kDa, 40 kDa, 35 kDa, 30 kDa, 25 kDa, 20 kDa, 15 kDa, 10 kDa, 9 kDa, 8 kDa, 7 kDa, 8 kDa, 5 kDa, 4 kDa, 3 kDa, 2 kDa, 1 kDa, 500 Da, 400 Da, 300 Da, 200 Da and 100 Da.

In some embodiments, the chitosan oligosaccharide has a degree of deacetylation of greater than or equal to 70%; 80%, 85%, 90% or 95% may also be selected, preferably 90%-100%.

In some embodiments, the chitosan oligosaccharide monomer has a molecular weight of 161, a degree of polymerization of 2-20, and a selected molecular weight in a range of 322-3220.

In some embodiments, the molecular weight of chitosan oligosaccharide, chitooligosaccharide, and glucosamine is less than or equal to 3200.

In some embodiments, methoxypolyethylene glycol, polyethylene glycol, and polyethyleneimine has a molecular weight of less than or equal to 40,000, and 30,000, 20,000, 15,000, 10,000, 8,000, 6,000, 4,000, 2,000, 1,500, 1,000 or 500 may be further selected.

In some embodiments, the soluble calcium salt is selected from CaCl$_2$ and/or CaNO$_3$.

In some embodiments, the polyinosinic-polycytidylic acid has a molecular weight of 100 bp-3000 bp.

In some embodiments, the polyinosinic-polycytidylic acid has a molecular weight of 100 bp-1500 bp.

In some embodiments, the combination product further comprises one or more of pH adjuster, sodium tripolyphosphate, sodium alginate, phenylboronic acid, catechol, a buffer salt/reagent, and water.

In some embodiments, respective components in the combination product are packaged separately;

In some embodiments, at least two components in the combination product are mixed and packaged together, for example, positive ions and water and/or a buffer salt are packaged together, In some embodiments, polyinosinic-polycytidylic acid is packaged in the form of its raw materials, for example, polyinosinic acid (PI) and polycytidylic acid (PC).

According to an aspect of the present disclosure, the present disclosure also relates to a complex for potentiating an immune response, which is prepared from the reagents in the combination product as described above.

In some embodiments, the preparation is carried out in a solution system, and in the reagent, the polyinosinic-polycytidylic acid has a concentration of 0.1 mg/ml-10 mg/ml; The concentration of polyinosinic-polycytidylic acid can reach a higher concentration theoretically by grafting to increase the solubilit;

In some embodiments, the preparation is carried out in a solution system, and in the reagent, the concentration of the polyinosin is 0.5 mg/ml-5 mg/ml, and 1 mg/ml, 2 mg/ml, 3 mg/ml, 4 mg/ml, 5 mg/ml, 6 mg/ml, 6.4 mg/ml, 7 mg/ml, 8 mg/ml or 9 mg/ml may be further selected.

In some embodiments, the preparation is carried out in a solution system, and in the reagent, the concentration of cationic stabilizer is 0.5 mg/ml~51.2 mg/ml;

In some embodiments, the cationic stabilizer has a concentration of 0.8 mg/ml~25.6 mg/ml, and 1 mg/ml, 2 mg/ml, 3 mg/ml, 4 mg/ml, 5 mg/ml, 10 mg/ml, 15 mg/ml or 20 mg/ml may be further selected.

In some embodiments, the preparation is carried out in a solution system, and in the reagent, the mass ratio of the polyinosinic-polycytidylic acid to the cationic stabilizer is 1:0.8~25.6; 1:6.4 or 1:12.8 may be further selected.

In some embodiments, the preparation is carried out in a solution system, and in the reagent, the concentration of calcium ions in the soluble calcium salt is 0.1 mM~1 mM, and 0.2 mM, 0.3 mM, 0.4 mM, 0.5 mM, 0.6 mM, 0.7 mM, 0.8 mM or 0.9 mM may be further selected.

In some embodiments, the complex is stored in a solution. The solution is preferably a buffer solution.

In some embodiments, the solution has a PH in a range from 5.0 to 7.2.

In some embodiments, the pH of the solution is equal to 5.9~6.9, and 6.0, 6.2, 6.4, 6.8, 7.0, 7.2, 7.4, 7.6 or 7.8 may also be selected.

According to an aspect of the present disclosure, the present disclosure also relates to the non-therapeutic use of the complex as described above as an immune adjuvant.

According to an aspect of the present disclosure, the present disclosure also relates to the use of the complex as described above for preparing an antibody, a vaccine formulation or a vaccine composition, or the use for preparing a vaccine excipient or a vaccine adjuvant.

According to an aspect of the present disclosure, the present disclosure also relates to a vaccine composition comprising the complex as described above and at least one antigen.

In some embodiments, the antigen is a virus, a *bacterium*, a protein, a polypeptide, a polysaccharide, a nucleic acid, or a small molecule-protein conjugate.

In some embodiments, the vaccine composition is, for example, an attenuated vaccine (for example, an attenuated vaccine of virus or bacteria), an inactivated vaccine (for example, an inactivated vaccine of virus or bacteria), a protein vaccine, a polysaccharide vaccine, a protein subunit vaccine, a chimeric vector vaccine, a DNA vaccine, a RNA vaccine, a polypeptide vaccine or a small molecule-protein conjugate vaccine.

According to an aspect of the present disclosure, the present disclosure also relates to the use of the complex as described above in regulating immune cell activity, which is applied in vivo or in vitro.

In some embodiments, the regulating immune cell activity is specifically potentiating immune cell activity.

In some embodiments, the immune cell is selected from macrophages, lymphocytes, and dendritic cells.

In some embodiments, the regulating or potentiating immune cell activity is promoting the immune cell releasing an inflammatory factor.

In some embodiments, the inflammatory factor includes IL-2, IL-6, IL-12p40, IL-18, IL-22, IFN-α, IFN-γ, and TNF-α.

In some embodiments, the inflammatory factor includes IFN-γ and TNF-α.

According to an aspect of the present disclosure, the present disclosure also relates to the use of the complexes as described above in the preparation of drugs for treating and/preventing tumors, anti-virus, anti-bacteria, anti-fungus, anti-parasitism, reducing side effects of chemotherapy, resisting fatigue or improving immunity, relieving host pain, and promoting an immune response to an antigen in a host.

In some embodiments, the drug is a dosage form of injection administration, a dosage form of respiratory administration, nasal drops, a dosage form of skin administration, a dosage form of mucosal administration, or a dosage form of cavitary administration.

In some embodiments, the dosage form of injection administration is selected from, for example, injections (including a variety of injection routes, such as intravenous injection, intramuscular injection, subcutaneous injection, and intradermal injection).

In some embodiments, the dosage form of respiratory administration is selected from: for example, sprays, aerosols, power aerosols and the like.

In some embodiments, the dosage form of skin administration is selected from the group consisting of: for example, solutions, lotions, liniments, ointments, plasters, pastes, and patches, etc., which is externally used and acts locally or exerts systemic effect by percutaneous absorption after administration.

In some embodiments, the dosage form of mucosal administration is selected from the group consisting of: for example, eye drops, nose drops, ophthalmic ointments, gargles, and sublingual tablets, etc., the mucosal administration may act locally or by mucosal absorption to exert systemic effect. ⑤ The dosage form of cavitary administration comprises, such as suppositories, aerosols, etc., used for a rectum, a vagina, an urethra, a nasal cavity, an ear canal, and the like. The cavitary administration may act locally or exert systemic effect after absorption.

In some embodiments, the antigen includes a tumor, a virus, a *bacterium*, a fungus or a parasite antigen.

In some embodiments, the host is a mammal.
In some embodiments, the host is a primate.
In some embodiments, the host is a human.

In some embodiments, when the antigen is a virus, a *bacterium*, a fungus, or a parasite antigen, the drug has an amount of 1 mg~8 mg per dose; In some embodiments, when the antigen is a tumor antigen, the drug has an amount of 1 mg~10 mg per dose.

According to an aspect of the present disclosure, the present disclosure also relates to a pharmaceutical composition comprising the complexes as described above. The pharmaceutical composition further comprises one or more of an immune cell therapy drug, an antibody therapy drug, a chemical drug, a substance that promotes mucosal immune absorption or mucosal adhesion, an immunomodulator, a pathogenic antigen, a pattern recognition receptor-ligand, and a pharmaceutically acceptable excipient.

In some embodiments, the immune cell therapy drug is one or more selected from the group consisting of tumor infiltrating lymphocytes (TILs), dendritic cells (DCs), cytokine induced killer cells (CIKs), dendritic cells-cytokine induced killer cells (DCs-CIKs), natural killer cells (NKs), γδT cells, CD3AK, CAR-T and TCR-T.

In some embodiments, the antibody therapeutic drug is selected from the group consisting of an anti-PD1 antibody, an anti-PDL1 antibody, an anti-CTLA4 antibody and an anti-CD antigen antibody.

In some embodiments, the chemical drug is one or more selected from the group consisting of an alkylating agent, an antimetabolity, an antitumor antibiotic, a plant antitumor drug, a hormone drug and a miscellaneous drug;

The miscellaneous drug is selected from the group consisting of L-asparaginase, cisplatin, carboplatin, oxaliplatin, dacarbazine, hexamethylmelamine drugs, and derivatives of aforementioned drugs.

In some embodiments, the alkylating agent is selected from the group consisting of cyclophosphamide, busulfan, dacarbazine, cisplatin, mechlorethamine, phenylalanine mustard, nitrosoureas and derivatives of the foregoing drugs;

In some embodiments, the antimetabolity is selected from the group consisting of 5-fluorouracil, methotrexate, cytarabine, cyclocytidine, hydroxyurea, and derivatives of the foregoing drugs;

In some embodiments, the antitumor antibiotic is selected from the group consisting of actinomycin, mitomycin, jaundice, doxorubicin, daunomycin, dactinomycin, bleomycin and derivatives of the foregoing drugs;

In some embodiments, the hormone drug is selected from the group consisting of a sex hormone, a corticosteroid hormone, and derivatives of the foregoing drugs.

In some embodiments, the substance that promotes mucosal immune absorption or mucosal adhesion is one or more selected from the group consisting of anionic surfactants (such as carboxylates, sulfonates, sulfates, phosphates, etc.), cationic surfactants (such as amine salts, quaternary ammonium salts, heterocycles, onium salts, etc.), zwitterionic surfactants (such as carboxylate type, sulfonate type, phosphate type, betaine type, imidazoline type, amino acid type, etc.), non-ionic surfactants (such as alkyl polyglycoside type, polyoxyethylene type, polyol type, alkanolamide type, block polyether type), special surfactants (such as fluorine-containing type, silicon-containing type, boron-containing type, polymer type, etc.), chelating agents (such as polyphosphate, aminocarboxylic acid, 1,3-diketone, hydroxycarboxylic acid, polyamine, etc.), adhesives [water-soluble adhesives (such as starch, dextrin, polyvinyl alcohol, carboxymethyl cellulose, etc.), hot melt adhesives (such as polyurethane, polystyrene, polyacrylate, ethylene-vinyl acetate copolymer, etc.), solvent adhesives (such as shellac, butyl rubber, etc.), emulsion adhesives (such as vinyl acetate resin, acrylic resin, chlorinated rubber, etc.), solvent-free liquid adhesives (such as epoxy resin, etc.)], polylactic acid-hydroxyacetic acid copolymer, dextran, and polysaccharide.

In some embodiments, the immunomodulator is one or more selected from the group consisting of cytokines, chemokines, stem cell growth factors, lymphotoxins, hematopoietic factors, colony stimulating factors (CSFs), interferons, erythropoietins, thrombopoietins, tumor necrosis factors (TNFs), interleukins (ILs), granulocyte-colony stimulating factors (G-CSFs), granulocyte macrophage-colony stimulating factors (GM-CSFs) and stem cell growth factors.

In some embodiments, the pathogenic antigen is selected from the group consisting of tumors, virus, *bacterium*, fungi or parasite antigens.

In some embodiments, the tumors include: tumors arising from any lesions in bone, bone connection, muscle, lung, trachea, pharynx, nose, heart, spleen, artery, vein, blood, capillary, lymph node, lymphatic vessel, lymphatic fluid, oral cavity, pharynx, esophagus, stomach, duodenum, small intestine, colon, rectum, anus, appendix, liver, gallbladder, pancreas, parotid gland, sublingual gland, urinary kidney, ureter, bladder, urethra, ovary, fallopian tube, uterus, vagina, vulva, scrotum, testes, vas deferens, penis, eyes, ears, nose, tongue, skin, brain, brainstem, medulla oblongata, spinal cord, cerebro-spinal fluid, nerves, thyroid, parathyroid gland, adrenal gland, pituitary gland, pineal gland, pancreatic islet, thymus, gonad, sublingual gland, and parotid gland.

In some embodiments, the *bacterium* includes one or more of *Staphylococcus, Streptococcus, Listeria, Erysipelothrix, Renibacterium, Bacillus, Clostridiun, Mycobacteriun, Actinomyces, Nocardia, Corynebacteriun, Rhodococcus, Bacillus anthracis, erysipelas bacillus, Bacillus tetani, Listeria monocytogenes, Bacillus perfringens, Bacillus gangraenae emphysematosae, tuberculosis, Escherichia coli, Bacterium proteus, Shigella dysenteriae, Pneumobacillus, Bacterium burgeri, Clostridiun perfringens, Haemophilus influenzae, Haemophilus parainfluenzae, Moraxella catarrhalis, Acinetobacter, Yersinia, Legionella pnewnophila, Bordetella pertussis, Bordetella parapertussis, Shigella, Pasteurella, Vibrio cholerae*, and *Vibrio Parahemolyticus*.

In some embodiments, the parasite includes one or more of parasites in the digestive tract (such as roundworms, hookworms, tapeworms, endoamoeba *histolytica*, and Yal's flagellum, etc.), intraluminal parasites (such as *Trichomonas vaginalis*), intrahepatic parasites (such as liver fluke, *echinococcus*), intrapulmonary parasites (such as *paragonimus westermani*), brain tissue parasites (such as *Cysticercus cellulosae, Toxoplasma gondii*), intravascular parasites (such as schistosomiasis), intralymphatic parasites (such as filaria), muscle tissue parasites (such as *Trichinella* larvae), intracellular parasites (such as *plasmodium, Leishmania*), bone tissue parasites (such as hydatid; skin parasites, such as sarcoptid, follicle mite), and intraocular parasites (such as *thelazia callipaeda*, Cysticerecus cellulosaes).

In some embodiments, the viruse includes one or more of adeniviridae, arenaviridae, astroviridae, bunyaviridae, cliciviridae, flaviviridae, hepatitis delta virus, hepeviridae, mononegavirales, nidovirales, piconaviridae, orthomyxoviridae, papillomaviridae, parvoviridae, polyomaviridae, poxviridae, reoviridae, retroviridae, or togaviridae.

In some embodiments, the virus is Human papillomavirus.

In some embodiments, the fungus include one or more of *Coccidioides immitis, Coccidioides posadasii, Histoplasma capsulatum, Histoplasma duboisii, Blastomyces lobo, Paracoccidioides brasiliensis, Blastomyces dermatitis, Sporothrix schenckii, Penicillium marneffei, Candida albicans, Candida glabrata, Candida tropicalis, Candida lusitaniae, Pneumocystis carinii, Aspergillus, Erophiala jeansebnei,*

*Fonsecaea Pedmsoi, Fonsecaea compacta, Chmmomyces verruciformis, Pigmentation dermatitis, Geotrichum candidum, Pseudallescheria boydii, Cryptococcus neoformans, Trichosporon Cutaneum, Rhizopus oryzae, Mucor indicus, Absidia corymbifera, Syncephalastrum racemosum, Basidiobolus ranarum, Conidiobolus coronatus, Conidiobolus incongruus, Enterocytozoon bieneusi, Encephalitozoon intestinalis, Rhinosporidium seeberi*, hyalohyphomycet, and *phaeohyphomycete*.

In some embodiments, the pattern recognition receptor-ligand is selected from the group consisting of a TLR receptor-ligand, a RLR receptor-ligand, a CLR receptor-ligand, and a NLR receptor-ligand.

In some embodiments, the ligand binding to a TLR receptor includes: for example, peptidoglycan, disaccharide, mannan, lipopeptide, glycolipid, atypical lipopolysaccharide, Serum amyloid protein. CPG DNA, dsRNA, ssRNA, LPS, PGN, saturated fatty acids, lipoteichoic acid, resistin, lactoferrin, surfactant protein, flagellin, hyaluronic acid, RNA-related antigen, Profilin-like molecules, etc.

In some embodiments, the ligand binding to a RLR receptors includes: for example, RNA, PIC, PICLC, PIC12u, etc.

In some embodiments, the ligand binding to a CLR receptor includes: for example, mannose and β-glucan on the surface of fungal cell walls, etc.

In some embodiments, the ligand binding to a NLR receptor include: for example, MDP, Mesθ DAP, etc.

According to an aspect of the present disclosure, the present disclosure also relates to a method for preparing a complex for potentiating an immune response, comprising:

contacting a polyinosinic-polycytidylic acid, at least a cationic stabilizer, and a soluble calcium salt in a liquid reaction system;

the cationic stabilizer is a water-soluble non-antibiotic amino compound having a molecular weight of less than or equal to 5 kDa, or a graft formed by the water-soluble non-antibiotic amino compound and one or more of methoxypolyethylene glycol, polyethylene glycol, polyethylenimine, folic acid and galactose.

In some embodiments, the polyinosinic-polycytidylic acid is prepared from a polycytidylic acid and a polyinosinic acid via a base pairing reaction.

In some embodiments, the molecular weights of the polycytidylic acid and the polyinosinic acid are greater than 23,000 Daltons.

In some embodiments, the molecular weight of the polycytidysic acid is in a range from 66,000 Daltons to 660,000 Daltons.

In some embodiments, the molecular weight of the polyinosinic acid is in a range from 66,000 Daltons to 660,000 Daltons.

In some embodiments, the base pairing reaction is carried out at a temperature of 40° C.~50° C., 41° C., 42° C., 43° C., 44° C., 45° C., 46° C., 47° C., 48° C., or 49° C. may be further selected.

In some embodiments, the base pairing reaction is carried out at pH from 6.8 to 7.6, 7.0, 7.2, 7.4 may be further selected.

In some embodiments, before contacting, the polyinosinic-polycytidylic acid is heated at 88° C.~92° C. for 70 min~120 min; In some embodiments, the temperature may be further selected from 82° C., 84° C., 86° C., 88° C., 90° C., 92° C., 94° C., 96° C. or 98° C.

In some embodiments, the heating time may be further selected from 80 min, 90 min, 100 min or 110 min.

In some embodiments, the liquid reaction system is at a temperature of 40° C.~50° C., and 41° C., 42° C., 43° C., 44° C., 45° C., 46° C., 47° C., 48° C., or 49° C. may be further selected.

In some embodiments, a method for preparing the graft includes:

firstly activating one or more of methoxypolyethylene glycol, polyethylene glycol, polyethylenimine, folic acid and galactose using carbonyl diimidazole, and then grafting the activated product with the water-soluble non-antibiotic amino compound in ionic liquid [bmim]Cl.

In some embodiments, the graft is a graft of chitosan oligosaccharide and methoxypolyethylene glycol, firstly activating methoxypolyethylene glycol (MPEG) using carbonyl diimidazole (CDI), and then grafting an activated MPEG with the chitosan oligosaccharide (COS) in ionic liquid [bmim]Cl.

In some embodiments, the grafting is reacted at 60° C.~80° C. under a non-oxidizing atmosphere.

In some embodiments, the method further includes:

adding a cross-linking agent solution dropwise to an obtained complex while stirring until Tyndall effect appears in the reaction system, and then stirring to obtain nanoparticles;

the cross-linking agent is at least one selected from the group consisting of sodium tripolyphosphate, sodium alginate, phenylboronic acid, and catechol.

In some embodiments, the cross-linking agent contains a (pathogen) antigen.

In some embodiments, the method further includes: co-incubating the complex or the nanoparticles with an antigen.

In some embodiments, the antigen is a protein or a polypeptide antigen.

According to an aspect of the present disclosure, the present disclosure also relates to a method for promoting an in vivo immune response in a host to an antigen, regulating and potentiating immune cell activity in a host, helping a host to reduce fatigue, or alleviating pains in a host, the method comprises: administrating the host for the complex as described above, or the vaccine composition as described above, or the pharmaceutical composition as described above.

In some embodiments, the host suffers from an infectious disease, and is administrated of the antigen compound to stimulate an immune response against the pathogen that causes the infectious disease.

In some embodiments, the administrating is carried out by parenteral injection, intramuscular injection, intraperitoneal injection, intravenous injection, subcutaneous injection, local administration, transdermal administration, or intradermal administration.

In some embodiments, the host is a tumor patient, a viral infected patient, a bacterial infected patient, a parasite infected patient, or a rhinitis patient who has failed surgery, chemotherapy, radiotherapy, or immunotherapy, or has been abandoned to treat by medical institutions.

In some embodiments, the method can be used in combination with surgery, radiotherapy, chemotherapy, and various immunotherapies, or, may also be used in combination with traditional therapies for the viral infected patient, the bacterial infected patient, or the parasite infected patient.

In some embodiments, the pain is that caused by microbial or parasitic infection, that caused by a cancer, or a neuropathic pain.

In some embodiments, when the antigen is a virus, a *bacterium*, a fungus, or a parasite antigen, the drug is administered at 1 mg/kg~8 mg/kg each time, and alternatively, is preferably administered once every day, every 2 days, every 3 days, or every 4 days;

When the antigen is a tumor antigen, the drug is administered at 1 mg/kg~10 mg/kg each time, and preferably, is administrated for a period of at least 360 days, at least 180 days, at least 60 days or at least 30 days.

The present disclosure provides a complex for potentiating an immune response prepared according to the method of the present disclosure.

The present disclosure provides the use of the complex for potentiating an immune response prepared according to the method of the present disclosure for preparing an antibody, a vaccine formulation or a vaccine composition, potentiating immune cell activity, treating and/preventing a tumor, antivirus, anti-bacteria, anti-fungus, anti-parasitism, reducing side effects of chemotherapy, resisting fatigue or improving immunity, relieving a pain in a host, and promoting an immune response in a host to an antigen.

The embodiments of the present disclosure will be described in detail below in combination with examples, but those skilled in the art will understand that the following examples are only intended to illustrate the present disclosure and should not be regarded as limiting the scope of the present disclosure. The examples that are indicated at no specific condition are carried out in accordance with conventional conditions or conditions recommended by the manufacturer. The reagents or instruments used without the indication of manufacturer are all conventional products that are commercially available.

Example 1 Preparation of Pamica

I. Preparation of Pamica Complex
1. Preparation of PBS Solution (pH 7.2):
1.1 Preparation of sodium chloride solution (0.85%, 1500 ml): 12.75 g of sodium chloride was weighed, added into a 2000 ml measuring cylinder, and fixed at 1500 ml by water injection;
1.2 Preparation of disodium hydrogen phosphate solution (0.006 mol/L, 500 ml): 0.4259 g (0.006×0.5×141.96) of disodium hydrogen phosphate was weighed, added into a 500 ml volumetric flask, and diluted to 500 ml with 0.85% saline;
1.3 Preparation of sodium dihydrogen phosphate solution (0.006 mol/L, 500 ml): 0.4140 g (0.006×0.5×137.99) of sodium dihydrogen phosphate was weighed, added into a 500 ml volumetric flask, and diluted to 500 ml with 0.85% saline;
1.4 Preparation of PBS solution with a pH of 7.2:273.6 ml of "the solution at 1.2" is mixed with 126.4 ml of "the solution at 1.3".
2. Preparation of PIC Solution (2.0 mg/ml, 100 ml):
2.1 114.5 mg (2.0 mg/ml*100 ml*[1.04/(1.04+1)]/91.5%/(1-2.7%)) of PI was weighed, added into a 250 ml triangular flask, dissolved by adding 50 ml PBS solution, and equilibrated in a water bath at 40° C.-60° C.;
2.2 113.2 mg (2.0 mg/ml*100 ml*[1/(1.04+1)]/90.4%/(1-4.2%)) of PC was weighed, added into a 250 ml triangular flask, dissolved by adding 50 ml PBS solution, and equilibrated in a water bath at 40° C.-60° C.;
2.3 Preparation of PIC solution: 50 ml PI solution was poured into 50 ml PC solution, and the mixture was reacted in a water bath at 45° C. for 30 minutes.
2.4 The PIC solution was heated at 80° C.-99° C. for 15 minutes~300 minutes.
3. Preparation of Calcium Chloride Solution (0.16 Mol/L, 25 ml):
0.5881 g of CaCl$_2$.2H$_2$O (MW: 147.02) was weighed, added into a 100 ml triangular flask, dissolved by adding about 25 ml of water for injection, and diluted to 100 ml.

4. Preparation of COS-g-MPEG:

The method for preparing COS-g-MPEG graft is as follows: chitosan oligosaccharide grafted methoxypolyethylene glycol (COS-g-MPEG) graft copolymer was prepared and used as an excipient for the preparation of an anti-cancer drug.

Principle: carbonyl diimidazole (CDI) coupling is used for the preparation of COS-g-MPEG. Firstly, methoxypolyethylene glycol (MPEG) is activated with carbonyl diimidazole to prepare an activated MPEG, and then the activated MPEG is reacted with chitosan oligosaccharide (COS) in an ionic liquid to synthesize COS-g-MPEG copolymer. The specific reaction includes the following three steps:

4.1 Preparation of ionic liquid 1-butyl-3-methylimidazole chloride salt ([BMIM]Cl)

1-methyl imidazole is reacted with chlorobutane to prepare ionic liquid [BMIM]Cl, and the synthetic reaction equation is as follows:

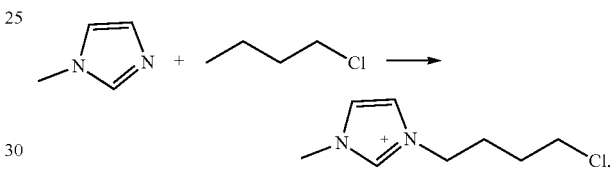

4.2 Activation of methoxypolyethylene glycol (MPEG, molecular weight of 1000)

MPEG is actived with CDI, and the synthetic reaction equation is as follows:

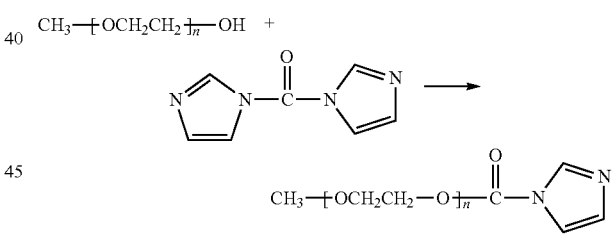

4.3 Synthesis of COS-g-MPEG copolymer;

The activated MPEG is grafted and polymerized with COS in an ionic liquid, and the synthetic reaction equation is as follows:

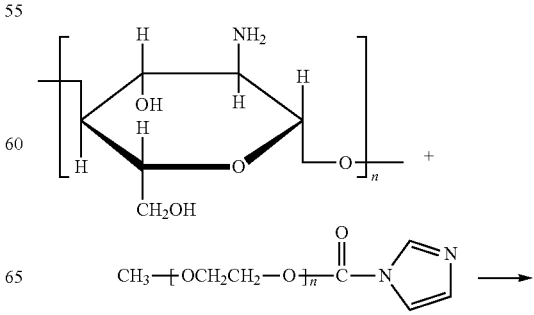

-continued

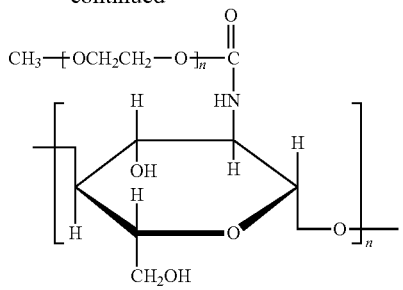

4.4 Equipments and reagents:

Methyl imidazole, chlorobutane, toluene, methoxypolyethylene glycol, carbonyl diimidazole, anhydrous ether, 4A molecular sieve (2 mm-3 mm), dimethyl sulfoxide, 1,4-dioxane, chitosan oligosaccharide, heat-collecting thermostatic magnetic heating stirrer (DF-101S type), electronic balance, electrothermal blast drying oven, circulating water vacuum pump, automatic triple pure water distiller, vacuum drying oven, freeze dryer, glass instrument airflow dryer, single-phase capacitor starting motor, rotary vane vacuum pump, sextuple magnetic heated stirrer, cellulose dialysis bag, ready-to-use dialysis bag 45-2000RC membrane, three-necked flask (500 mL, 1000 mL), glass stopper, magnetic stir bar, disposable paper cup, 500 mL beaker, 2 L beaker, disposable dropper, medicine spoon, reagent bottle, desiccator, etc.

4.5 Preparations:

4.5.1 Preparation of distilled water

The distilled water was prepared using Z-97A automatic triple pure water distiller for three times.

4.5.2 Cleaning of glasswares

The three-necked flask, the glass stopper, the petri dish, and the magnetic stir bar, etc. were firstly washed with tap water, then rinsed with distilled water three times, and finally dried in a glass instrument airflow dryer.

4.5.3 Solvent drying: to a disposable beaker added was appropriate amount of molecular sieve, followed by appropriate amount of dimethyl sulfoxide, 1,4-dioxane, and anhydrous ether, and water was removed.

4.5.4 Freezing anhydrous ether in advance.

4.6. Operations (points for attention at each step):

4.6.1 Preparation of ionic liquid (1) To a 500 mL three-necked flask added was 100 g of 1-methylimidazole and 148.5 mL of chlorobutane in sequence. A condenser was installed onto the flask, and argon was introduced for 30 min. The solution was stirred magnetically, then heated to 80° C. in an oil bath, and reacted for 24 h;

(2) After completion of the reaction, the flask was taken out, and the solution was cooled to room temperature, and frozen in a refrigerator at −18° C. for 2 h. Stratification of the solution can be observed, and then the supernatant liquid was discarded (mainly for chlorobutane removal);

(3) The remainder was put in a blast drying oven at 80° C., and after the solid was completely melted, an appropriate amount of toluene was added while it was hot and shaken to thoroughly mix toluene with the solution. The mixture was then cooled to room temperature, frozen in the refrigerator, and then taken out, and the supernatant liquid was discarded (1-methylimidazole and chlorobutane were dissolved in toluene, and toluene, 1-methylimidazole and chlorobutane were removed);

(4) The step (3) was repeated twice for the complete removal of unreacted chlorobutane;

(5) The sample was put in a vacuum drying oven and heated to 90° C. After being completely melted, the sample was dried in vacuo at 90° C. for 8 h (for toluene removal), then taken out, stood for cooling to room temperature, and then put in a desiccator for use.

4.6.2 Activation of MPEG (1) 10 mL of dimethyl sulfoxide and 20 mL of 1,4-dioxane were added into a 500 mL three-necked flaskand stirred magnetically. 20 g of MPEG was added, and after MPEG was completely melted, 3.24 g of CDI was added. The mixture was heated to 37° C. in a water bath and reacted for 18 h;

(2) After completion of the reaction, the sample was added to pre-cooled anhydrous ether in the ice-water bath while stirring magnetically, and the opening of the beaker was covered with preservative film, and then the sample was put in the refrigerator for 30 min;

(3) The sample was taken out after 30 min, and the supernatant solution was discarded. Pre-cooled anhydrous ether was added to the precipitate and stirred magnetically for 30 min, and then the mixture was put in the refrigerator for 30 min.

(4) The step (3) was repeated twice to fully wash away the unreacted CDI;

(5) The supernatant solution was discarded and the remainder was put in a blast drying oven at 40° C. for 6 h to remove ether preliminarily;

(6) The residue was put into a vacuum drying oven at 40° C., dried in vacuo for 2.5 h to completely remove ether, then taken out, stood for cooling to room temperature, and then put in a desiccator for use.

4.6.3 Preparation of COS-g-MPEG:

(1) The ionic liquid was melted in a blast drying oven at 80° C.;

(2) 105 g of ionic liquid was weighed, added into a three-necked flask, and heated to 70° C. in an oil bath. Argon was introduced, and 9 g of COS was slowly added. After COS was completely dissolved, 6 g of activated MPEG was added and the mixture was stirred magnetically. After all raw materials were added, the mixture was reacted for 6 h under the protection of argon. After completion of the reaction, the reaction bottle was cooled to room temperature;

(3) Firstly, a dialysis bag was clamped at a side with a clip, and an appropriate amount of distilled water was added to wash the dialysis bag for three times and to check whether water leaks from the dialysis bag. Then, the sample in the reaction bottle was put into the dialysis bag (molecular weight cut-off of 2000) and dialysed for 72 hours, the distilled water is at an amount that is suitable for submerging the dialysis bag. Water was refreshed every 2 h~3 h on the first day, then every 12 h.

(4) After completion of the dialysis, the solution was added into a 1000 mL three-necked flask and put into a water bath. A vacuum distillation apparatus was installed well, and the distillation temperature was gradiently increased from room temperature to 25° C., 30° C., 35° C., 40° C., 45° C., 50° C., 55° C., 60° C. The distillation continued until about 50 mL of the solution remained, then the distillation apparatus was removed. The sample was poured into a disposable beaker while it was hot. The opening of the beaker was covered with a disposable glove, and the sample was frozen in the refrigerator for no less than 8 hours.

(5) The freeze dryer was pre-cooled for 30 min, so that the freezing temperature reached −52° C. The sample was crushed, and spread and flattened in a petri dish. The petri dish was put in the pre-cooled freeze dryer, and freeze-dried at −52° C. for 30 h. After completion of the freezing, the freeze dryer was turned off, and the sample was taken out, weighed, put in a reagent bag, and then stored in a desiccator.

(6) Infrared analysis: an appropriate amount of sample was taken, and tableted with potassium bromide. The infrared spectrum of the sample was measured with the scan area of 400 cm-1~4000 cm-1.

components. In this example, taking MPEG for example, the compatibility significantly increased when the graft of MPEG with a cationic stabilizer (such as chitosan oligosaccharide) was prepared with PIC. In theory, the compatibility will also increase if a PEG (and the like)-grafted cationic stabilizer such as chitosan is prepared with PIC; after the cationic stabilizer is grafted with PEG, the graft itself will also have the characteristics of PEG.

| | | PBS solution of COS-g-MPEG | | | | | | | Results |
|---|---|---|---|---|---|---|---|---|---|
| No. | PIC (2 mg/ml) | 0.16% (1.6 mg/ml) | 0.32% (3.2 mg/ml) | 0.64% (6.4 mg/ml) | 1.28% (12.8 mg/ml) | 2.56% (25.6 mg/ml) | 5.12% (51.2 mg/ml) | CaCl$_2$ (0.16 mol/L) | Solubility | Hyperchromic effect (standard for polyinosinic-polycytidylic acid ≥55%) |
| 6.1 | 1.0 ml | 1.0 ml | | | | | | 0.005 ml | clear solution | 65.3% |
| 6.2 | 1.0 ml | | 1.0 ml | | | | | 0.005 ml | clear solution | 70.6% |
| 6.3 | 1.0 ml | | | 1.0 ml | | | | 0.005 ml | clear solution | 62.7% |
| 6.4 | 1.0 ml | | | | 1.0 ml | | | 0.005 ml | clear solution | 64.7% |
| 6.5 | 1.0 ml | | | | | 1.0 ml | | 0.005 ml | clear solution | 44.1% |
| 6.6 | 1.0 ml | | | | | | 1.0 ml | 0.005 ml | clear solution | 15.6% |

5. Preparation of a Solution of COS-g-MPEG in PBS:
5.1 5.12%: 0.128 g of COS-g-MPEG was weighed, added into a 5 ml centrifuge tube, dissolved by adding PBS solution, and diluted to 2.5 ml;
5.2 2.56%: 1.2 ml of 5.12% solution+1.2 ml of PBS solution;
5.3 1.28%: 1.2 ml of 2.56% solution+1.2 ml of PBS solution;
5.4 0.64%: 1.2 ml of 1.28% solution+1.2 ml of PBS solution;
5.5 0.32%: 1.2 ml of 0.64% solution+1.2 ml of PBS solution;
5.6 0.16%: 1.2 ml of 0.32% solution+1.2 ml of PBS solution;
6. Preparation of Pamica Solution of PIC, COS-g-MPEG and Calcium Chloride Solution:
6.1 1.0 ml of PIC solution was put in a water bath at 45° C., 1.0 ml of 5.1 was added dropwise, and then 0.005 ml of calcium chloride solution was added to reach its final concentration of 0.0004 mol/L.
6.2 1.0 ml of PIC solution was put in a water bath at 45° C., 1.0 ml of 5.2 was added dropwise, and then 0.005 ml of calcium chloride solution was added to reach its final concentration of 0.0004 mol/L.
6.3 1.0 ml of PIC solution was put in a water bath at 45° C., 1.0 ml of 5.3 was added dropwise, and then 0.005 ml of calcium chloride solution was added to reach its final concentration of 0.0004 mol/L.
6.4 1.0 ml of PIC solution was put in a water bath at 45° C., 1.0 ml of 5.4 was added dropwise, and then 0.005 ml of calcium chloride solution was added to reach its final concentration of 0.0004 mol/L.
6.5 1.0 ml of PIC solution was put in a water bath at 45° C., 1.0 ml of 5.5 was added dropwise, and then 0.005 ml of calcium chloride solution was added to reach its final concentration of 0.0004 mol/L.
6.6 1.0 ml of PIC solution was put in a water bath at 45° C., 1.0 ml of 5.6 was added dropwise, and then 0.005 ml of calcium chloride solution was added to reach its final concentration of 0.0004 mol/L.
7. Results
MPEG, PEG, PEI, and the like all have good water solubility, and have good compatibilities with many organic It was shown from the test results that the solution is still clear at 1: 25.6 mg of PIC: COS-g-MPEG, but results for the hyperchromic effect show that more grafts do not means better. In addition, the samples at 6.1, 6, 6.3, 6.4, 6.5 and 6.6 was left at room temperature after being prepared on May 7, 2018, and on May 14, 2018, it was observed that flake precipitate appeared in the sample at 6.6 and could not be dissolved again. Based on a comprehensive consideration, the ratio of PIC to COS-g-MPEG in the Pamica formulation is limited within a range of 1 mg:6.4 mg.

II. Preparation of Pamica Nanoparticles

Sodium tripolyphosphate (TPP) with medical standards was purchased. The PIC-COS-g-MPEG-CaCl$_2$ complex at an appropriate ratio was stirred with a constant temperature magnetic stirrer at a speed, and TPP aqueous solutions at different concentrations were added dropwise. Dropwise addition stopped immediately when an obvious opalescence was observed, and the reaction was maintained for 30 minutes. The nanoparticles with a particle size of less than 1000 nm were formed by self-assembly through ion cross-linking and obtained by high-speed centrifugation. The nanoparticles were verified at various test to be qualified.

III. Polypeptide or Protein Antigen Nanoparticles

Scheme 1: a polypeptide or protein antigen was added during the formation of above-mentioned nanoparticles: the respective components were incorporated into the PEG-COS graft or COS matrix, and the polypeptide or protein antigen entered the water phase containing TPP and bonded. The respective components must be bonded at a suitable ratio and at a pH while stirring with magnetic beads to form complex and polypeptide or protein antigen nanoparticles.

Scheme 2: the polypeptide or protein antigen was incubated with the above-mentioned pre-formed complex and nanoparticles, so that the polypeptide or protein antigen was bonded on a surface of the complex and the nanoparticles, or the polypeptide or protein antigen was mixed with the above-mentioned complex and nanoparticles at a ratio. The mixture was stirred magnetically for 5 minutes, stood at room temperature for 1 hour, and ultracentrifuged under glycerol matrix at 20,000 rcf at 4° C. for 2 hours, and then the complex and polypeptide or protein antigen nanoparticles were obtained.

The complexes and polypeptide or protein antigen nanoparticles of Scheme 1/Scheme 2 need to be verified at various tests to be qualified.

IV. The Formulation of Pamica

The above-mentioned complex/complex comprising the graft/complex nanoparticles/polypeptide or protein antigen nanoparticles were aseptically packed into suitable/qualified packaging material to prepare various dosage forms such as an injection, a spray or an aerosol, and made into various products after being verified at various product tests to be qualified.

The above-mentioned complex/complex comprising graft/complex nanoparticles/polypeptide or protein antigen nanoparticles were aseptically packed into suitable/qualified packaging material and prepared into ointment.

An example of preparing a spray: Pamica was prepared according to the above method, and Pamica solution was put in spray bottles. A spray pattern detection of medical solution and a data detection of droplet distribution were performed for 20 bottles of Pamica solution, respectively.

The spa patterns are shown in the following table:

| Client medical solution | | D1(cm) Maximum value | D2(cm) Minimum value | Spraying distance (cm) | Ovality (D1/D2) | Average ovality | Full-spraying angle | Average full-spraying angle |
|---|---|---|---|---|---|---|---|---|
| APF 100 snap on NTS | 1# | 4.4 | 4.1 | 5 | 1.07 | 1.20 | 46 | 43 |
| | 2# | 4.2 | 3.0 | 5 | 1.40 | | 40 | |
| | 3# | 4.5 | 3.5 | 5 | 1.29 | | 44 | |
| | 4# | 4.5 | 3.6 | 5 | 1.25 | | 44 | |
| | 5# | 4.2 | 3.7 | 5 | 1.14 | | 43 | |
| | 6# | 4.0 | 3.0 | 5 | 1.33 | | 39 | |
| | 7# | 4.7 | 4.1 | 5 | 1.15 | | 48 | |
| | 8# | 4.5 | 4.0 | 5 | 1.13 | | 46 | |
| | 9# | 4.0 | 3.7 | 5 | 1.08 | | 42 | |
| | 10# | 4.0 | 3.5 | 5 | 1.14 | | 41 | |

Note:
The spraying forms were evaluated by the ratio of the longest diameter to the shortest diameter (the closer to 1.0, the better the spray forms).

| Client medical solution | | <10 μm (%) | D10 (μm) | D50 (μm) | D90 (μm) | SPAN | Average |
|---|---|---|---|---|---|---|---|
| APF 100 snap on NTS | 1# | 1.2 | 55.32 | 115.28 | 187.52 | 1.15 | 1.1 |
| | 2# | 1.1 | 48.37 | 98.36 | 166.84 | 1.20 | |
| | 3# | 1.0 | 54.13 | 115.22 | 192.30 | 1.20 | |
| | 4# | 1.3 | 42.18 | 89.78 | 132.54 | 1.01 | |
| | 5# | 1.0 | 60.77 | 123.53 | 190.03 | 1.05 | |
| | 6# | 1.3 | 51.81 | 111.83 | 173.90 | 1.09 | |
| | 7# | 1.3 | 56.99 | 120.23 | 183.28 | 1.05 | |
| | 8# | 1.4 | 43.88 | 87.50 | 126.41 | 0.94 | |
| | 9# | 1.2 | 53.66 | 115.04 | 195.98 | 1.24 | |
| | 10# | 1.2 | 53.28 | 125.02 | 197.17 | 1.15 | |

Example 2 the Test of Pamica Combined with PEI to Increase Solubility

Preparation was performed referring to the preparation method of "Pamica combined with PEG" (i.e. Example 1). After increasing the amount of COS in Pamica, precipitation appeared, which affected the uniformity of administration thereof. Precipitation may be avoided after adding PEI, and the dosage of COS was increased to further enhance the immune effect thereof.

| | The content of each component per 1 ml sample | | | | |
|---|---|---|---|---|---|
| Name | PIC (mg/ml) | COS (mg/ml) | PEI (mg/ml) | CaCl$_2$ (mol/L) | Results |
| Group 1 | 1 | 0.4 | 0 | 0.0004 | clear solution |
| | 1 | 0.8 | 0 | 0.0004 | clear solution |
| | 1 | 1.6 | 0 | 0.0004 | precipitation |
| Group 2 | 1 | 0.8 | 32 | 0.0004 | clear solution |
| | 1 | 1.6 | 32 | 0.0004 | clear solution |
| | 1 | 3.2 | 32 | 0.0004 | clear solution |
| | 1 | 6.4 | 32 | 0.0004 | clear solution |

The experiment clearly shows that after Pamica combined with PEI, the solubility of COS in PIC increased from 1.6 mg/ml to 6.4 mg/ml, increasing to at least 4 times.

The patent application No. CN105396130A discloses a "PIC-amino compound-$CaCl_2$ adjuvant and vaccine comprising the PIC-amino compound-$CaCl_2$ adjuvant", and discloses that the non-antibiotic amino compound may be optionally chitosan.

In this comparative example, water-soluble chitosan (chitosan hydrochloride, CS for short) was used to replace the chitosan oligosaccharide in Example 1 to compare the effects of water-soluble chitosan and chitosan oligosaccharide on the uniformity of administration. The results are shown in the following table.

| Name | PIC (mg/ml) | CS (mg/ml) | COS (mg/ml) | $CaCl_2$ (mol/L) | Results |
|---|---|---|---|---|---|
| Group 1 | 1 | 0.4 | 0 | 0.0004 | precipitation |
|  | 1 | 0.8 | 0 | 0.0004 | precipitation |
| Group 2 | 1 | 0 | 0.4 | 0.0004 | clear solution |
|  | 1 | 0 | 0.8 | 0.0004 | clear solution |

Studies have found that the addition of water-soluble chitosan leads to precipitation that can not be dispersed by shaking during the preparation, which affects the uniformity of administration thereof, while chitosan oligosaccharide can be used to solve the above problem. In addition, both chitosan grafted PEG or water-soluble chitosan need to be degraded into chitosan oligosaccharide having small molecular weight so as to be easily absorbed by human body, but chitosan oligosaccharide may be directly absorbed.

Example 3 PIC Heating and Molecular Weight Detection

PIC solution was prepared according to the preparation method of Example 1, 260 ml of PIC solution was divided into 13 tubes in total with 20 ml/tube. 12 tubes of samples were put in a constant temperature water bath when the temperature thereof rose to 80° C.-99° C. (preferably 90° C.). After the tubes were put in water bath, timing starts, and one tube was taken out at 10 minutes (band 3), 20 minutes (band 4), 30 minutes (band 5), 40 minutes (band 6), 50 minutes (band 7), 60 minutes (band 9), 70 minutes (band 10), 80 minutes (band 11), 90 minutes (band 12), 100 minutes (band 13), 110 minutes (band 14) and 120 minutes (band 15), respectively. The sample in band 2 is unheated.

Figure 2:
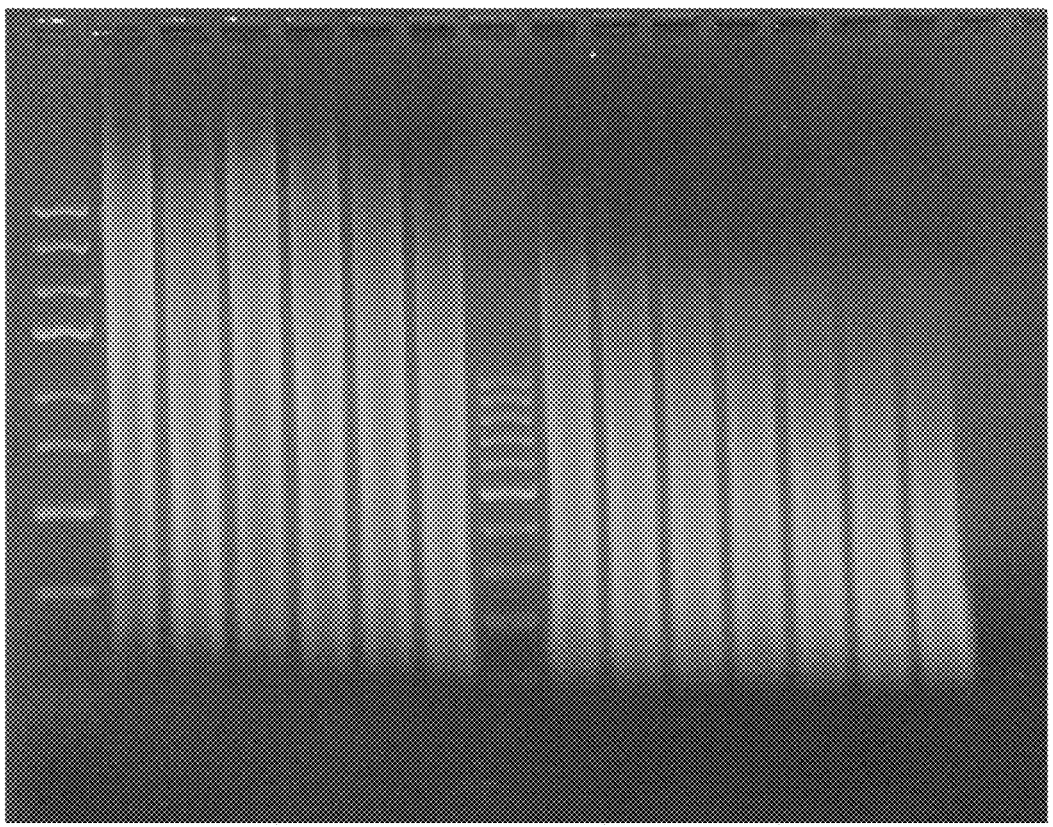
FIG. 2 is a molecular weight electrophoretogram of PIC after being heated for different periods of time.

The complex prepared by PIC (Pamica) and vaccine thereof heated for 70-120 minutes (preferably heated for 120 minutes) can pass the detection of abnormal toxicity in mice and guinea pigs according to "1141 Abnormal Toxicity Test", PHARMACOPOEIA OF THE PEOPLE'S REPUBLIC OF CHINA, the $4^{th}$ vol., 2015. The PIC used to prepare Pamica should be heated at 90° C. for at least 70 minutes, preferably at 90° C. for 120 minutes, before it is used for product preparation. The selected complexes prepared by unheated PIC (band 2) and prepared by heating for 60 minutes (band 9) and vaccines thereof cannot pass the detection of abnormal toxicity in guinea pigs. The results are shown in FIG. 2. Comparative band 1 from bottom to top: 100 bp, 300 bp, 500 bp, 750 bp, 1000 bp, 1500 bp, 2000 bp, 3000 bp, 5000 bp. Comparative band 8 from bottom to top: 100 bp, 200 bp, 300 bp, 400 bp, 500 bp, 600 bp, 700 bp, 800 bp, 900 bp, 1000 bp.

Example 4 Enzymatic Degradation Test of Pamica Complex

Method: the Pamica complex was prepared according to the preparation method of Example 1 of the present disclosure. After completion of the preparation, the respective samples of the Pamica complex and the polyinosinic-polycytidylic acid injection (polyinosinic-polycytidylic acid-kanamycin-calcium chloride) was diluted to 0.04 mg/ml, respectively, 5 ml sample diluent was added to each of 13 tubes (each 10 ml), then 25 μg of RNase (Cat. No. R4642) from sigma was added into each tube. The tubes were placed in a water bath at 37° C. 1 tube was taken out every 5 minutes to measure the OD value at 248 nm and a curve was drawn.

Figure 3:
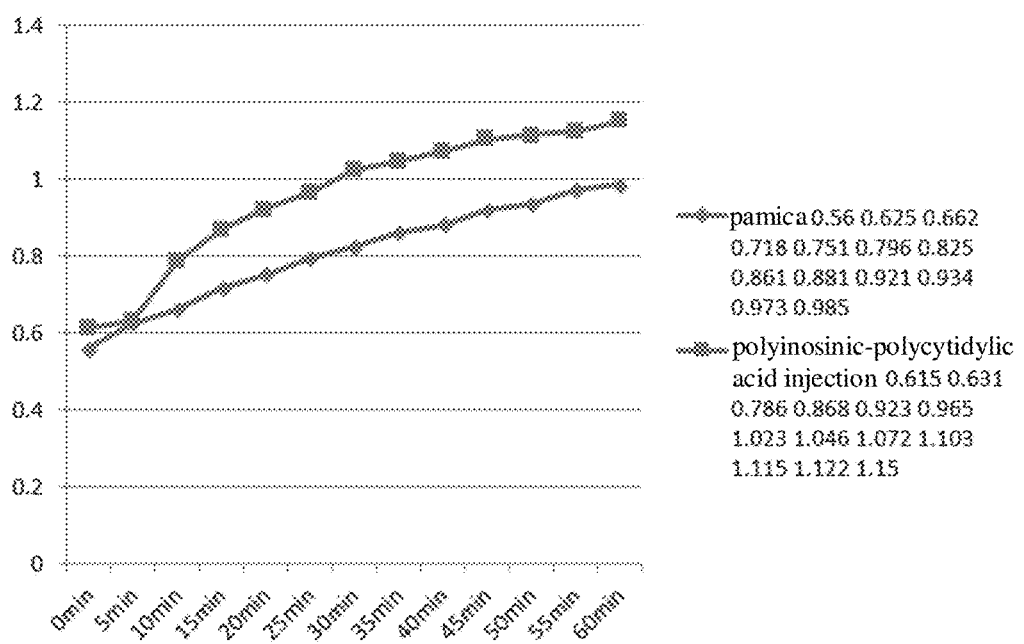
FIG. 3 is an enzymatic degradation curve of a Pamica complex according to an embodiment of the disclosure.

The result is shown in FIG. 3.

Example 5 the Pamica Complex of the Present Disclosure is a Complex with a New Structure (1) Determination of Melting Curve Peak Method: the respective samples of the Pamica complex and polyinosinic-polycytidylic acid injection of the present disclosure were diluted to 0.04 mg/ml, then transferred to 250 ml reagent bottles. The reagent bottles were placed in a water bath, and the water bath was heated up continuously. 3 ml of the respective samples were taken out every 5° C. and placed in a quartz cuvette. The OD value at 248 nm was measured, and a curve was drawn.

Figure 4:
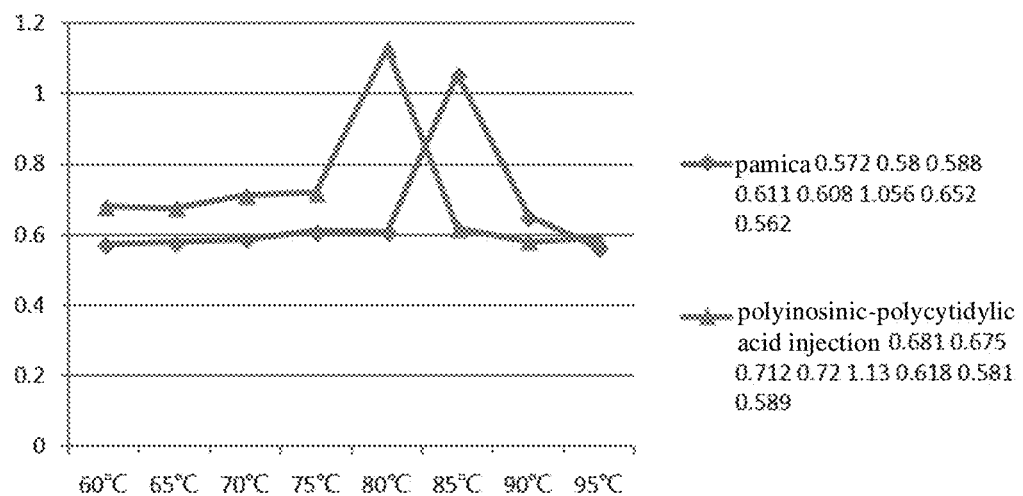
FIG. 4 is a melting curve of a Pamica complex according to an embodiment of the present disclosure.

The result is shown in FIG. 4.

The test result shows that the Pamica complex (PIC-cationic stabilizer-calcium chloride) of the present disclosure has a melting curve peak at 85° C., and the polyinosinic-polycytidylic acid injection (PIC-kanamycin-calcium chloride) has a melting curve peak at 80° C., which indicates that the Pamica complex of the present disclosure is a new complex.

(2) Absorption Peak Scanning

Figure 5:
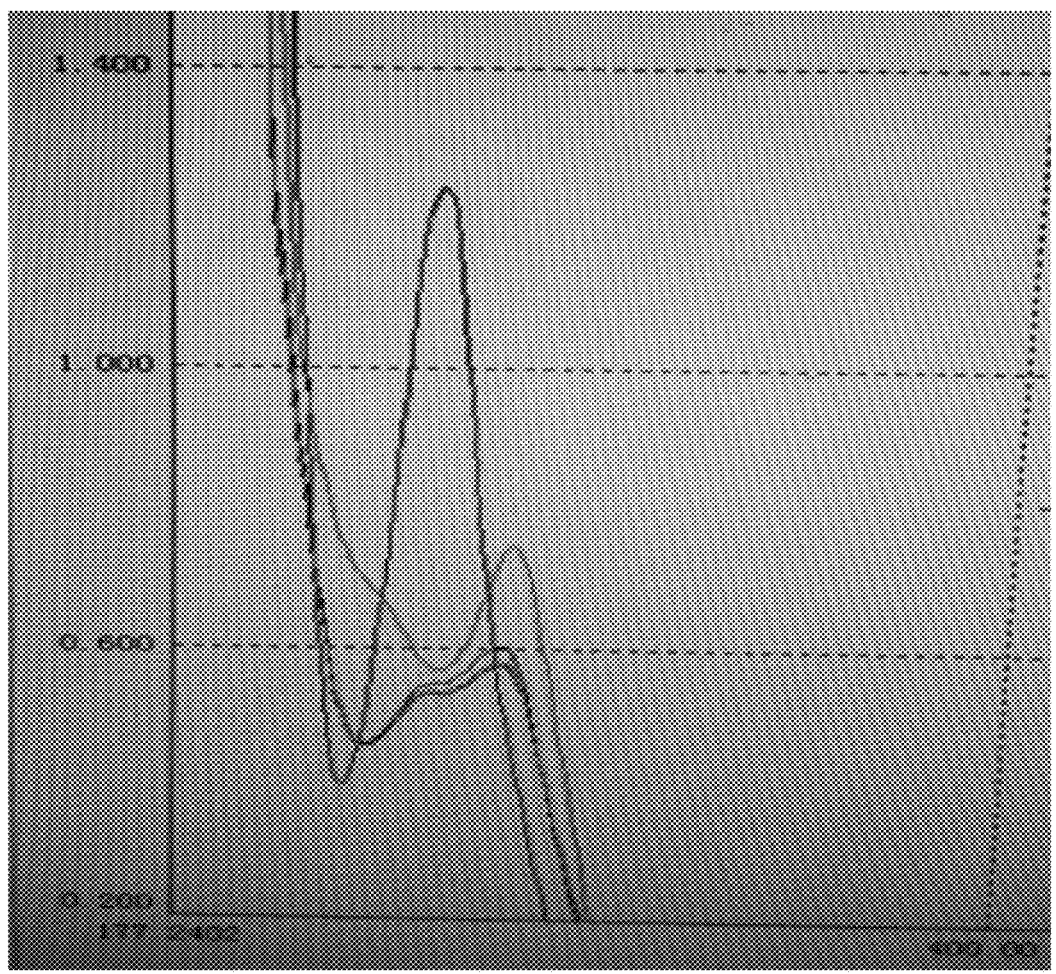
FIG. 5 is a scanning absorption spectrum of respective substances at 240 nm-260 nm according to an embodiment of the disclosure.

PI solution, PC solution, PIC solution, PIC-COS solution. PIC-COS-$CaCl_2$ solutions were prepared according to the preparation method of Example 1, respectively. The above samples were diluted to 0.04 mg/ml with PBS buffer, and the scanning absorption spectrum was measured separately by ultraviolet. FIG. 5 shows that the peaks appearing at 240 nm-260 nm from high to low are those of PI, PC, PIC, PIC-COS, PIC-COS-$CaCl_2$, of these peaks, the peaks of PIC-COS and PIC-COS-$CaCl_2$ were overlapped, which shows that the Pamica complex (PIC-COS-$CaCl_2$) of the present disclosure is a complex with a new structure.

Example 6 Partial Nanoparticles Formed by PIC, COS and Calcium Chloride

Figure 6:
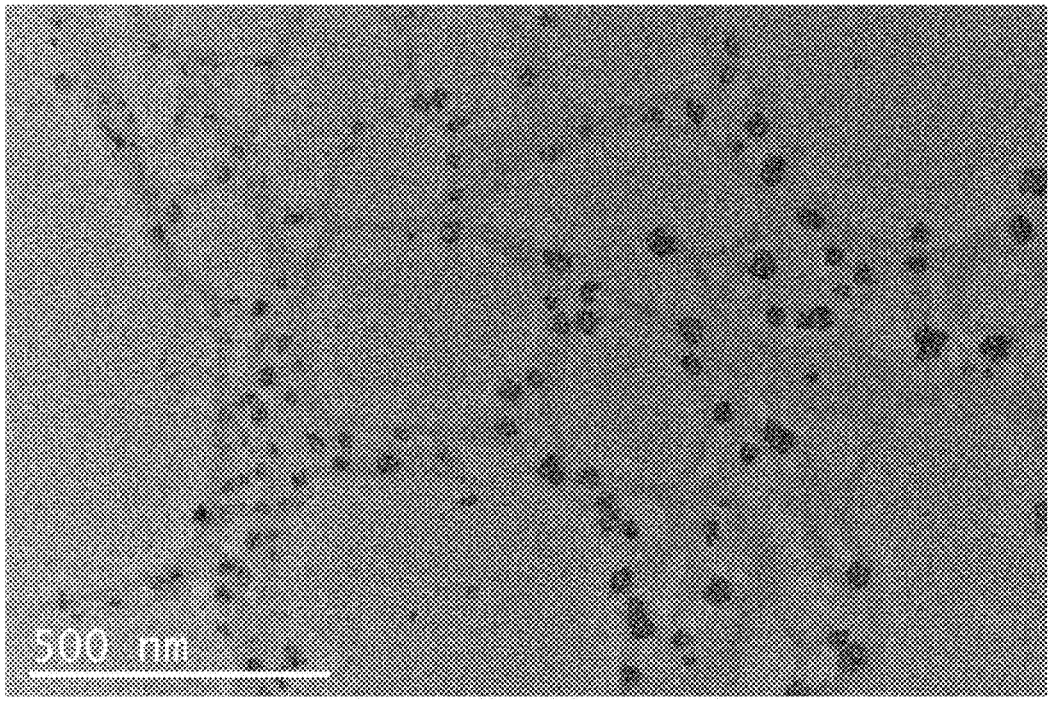
FIG. 6 is a transmission electron microscope image of a PIC-COS-$CaCl_2$ complex according to an embodiment of the disclosure; scale bar=500 int.
Figure 7:
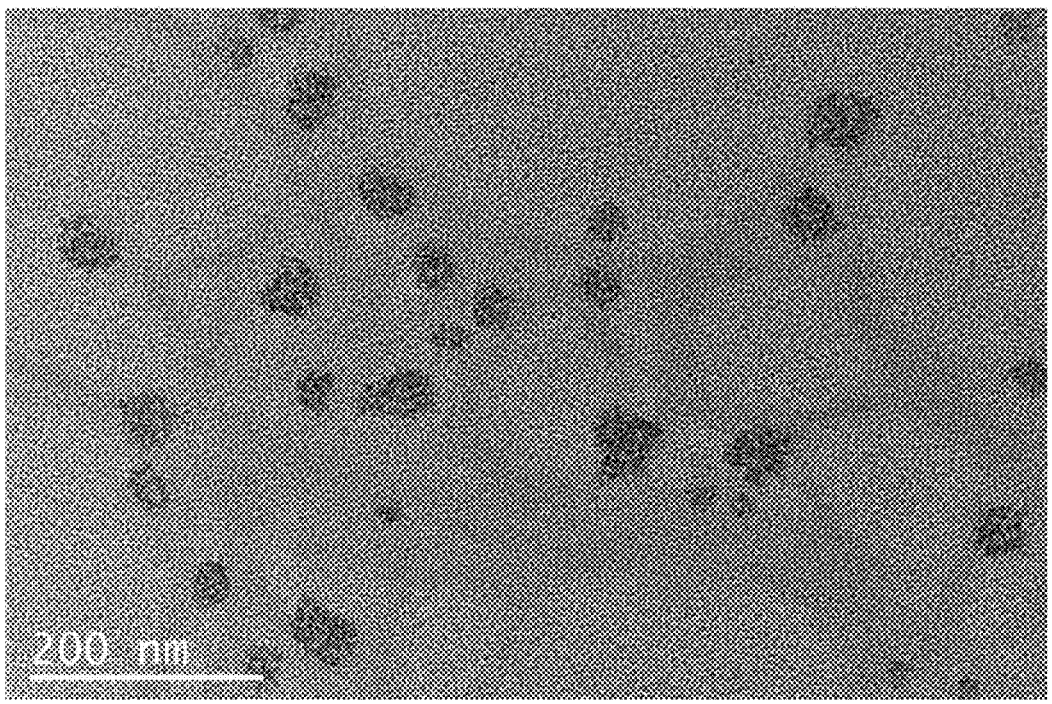
FIG. 7 is a transmission electron microscope image of a PIC-COS-$CaCl_2$ complex according to an embodiment of the disclosure; scale bar=200 nm.

Pamica was prepared according to the method of Example 1, wherein COS was selected as the cationic stabilizer, and calcium chloride was selected as the metal cation. It can be seen from the transmission electron micrographs (FIG. 6 and FIG. 7) that nanoparticles were formed in the Pamica solution. Most of the nanoparticles are spherical and relatively uniform, with a particle size of about 50 nm, and some of the nanoparticles are square with side lengths exceeding 100 nm.

Example 7 Partial Nanoparticles Formed by PIC, COS-g-MPEG and Calcium Chloride

Figure 8:
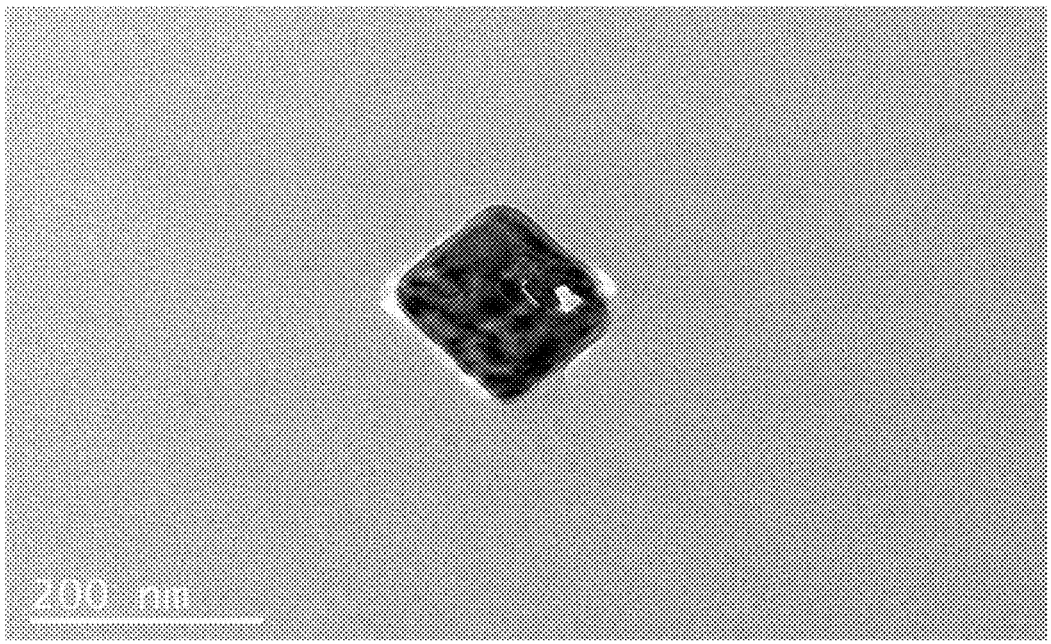
FIG. 8 is a transmission electron microscope image of a PIC-COS-g-MPEG-$CaCl_2$ complex according to an embodiment of the disclosure; scale bar=200 m.
Figure 9:
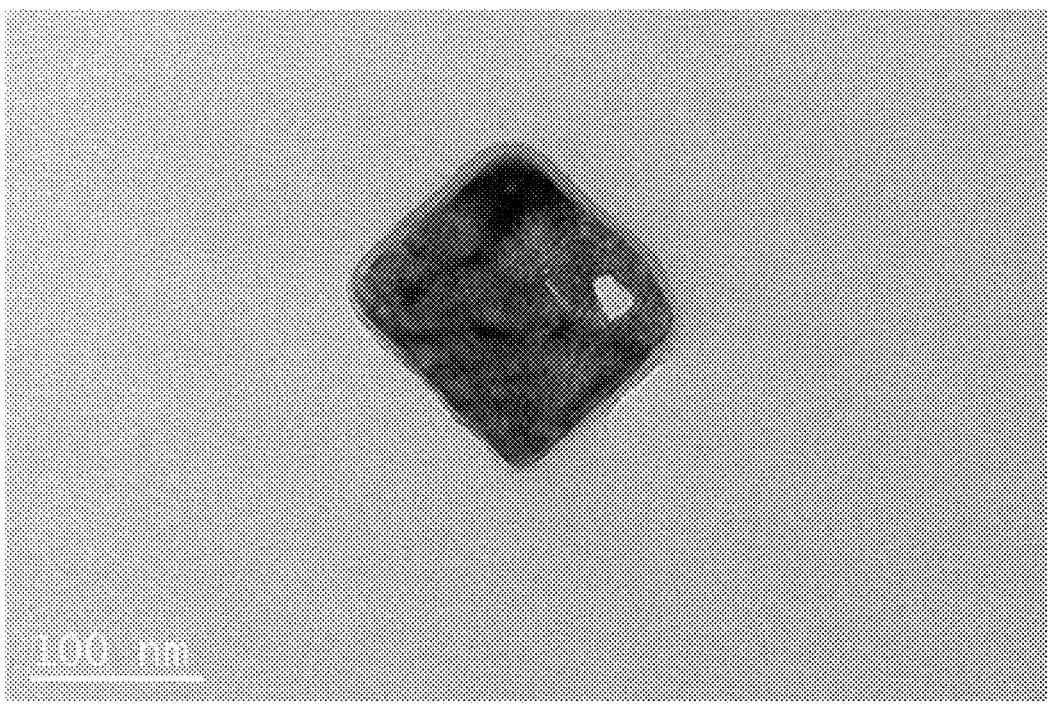
FIG. 9 is a transmission electron microscope image of a PIC-COS-g-MPEG-$CaCl_2$) complex according to an embodiment of the disclosure; scale bar=100 m.

Pamica was prepared according to the method of Example 1, wherein COS-g-MPEG was selected as the cationic stabilizer, and calcium chloride was selected as the metal cation. It can be seen from the transmission electron micrographs (FIG. 8 and FIG. 9) that nanoparticles, most of which are square with side lengths exceeding 100 nm, and a few are spherical, were formed in the Pamica solution.

Example 8 Partial Nanoparticles Formed by PIC, COS, TPP and Calcium Chloride

Figure 10:
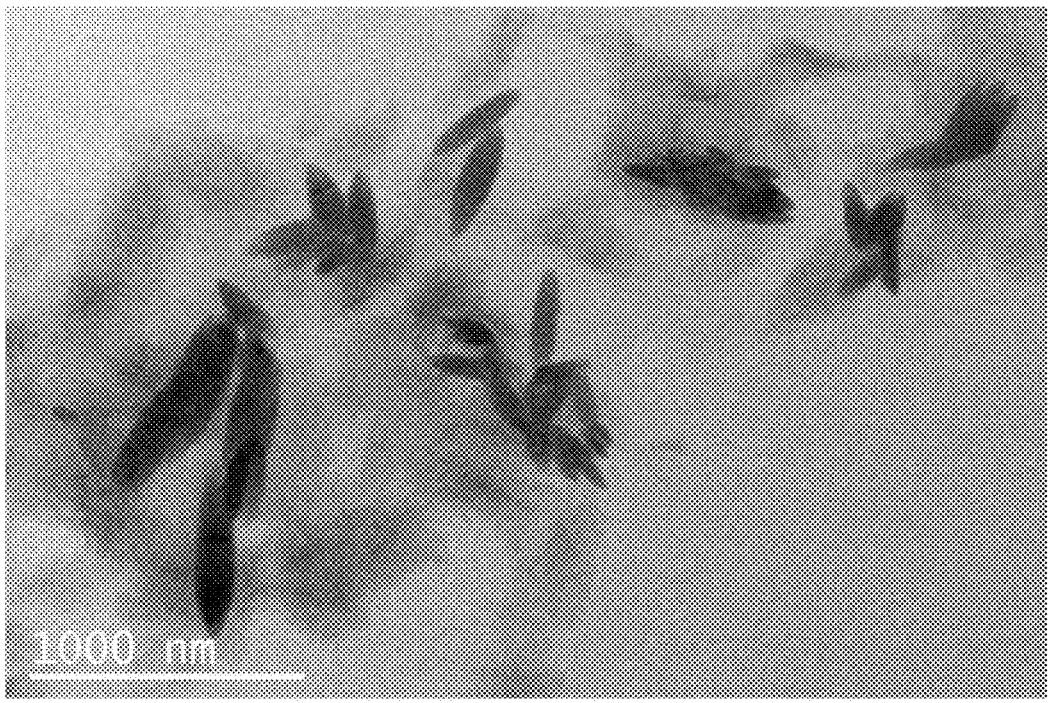
FIG. 10 is a transmission electron microscope image of the nanoparticles formed from the PIC-COS-$CaCl_2$ complex and TPP according to an embodiment of the disclosure; scale bar=1000 nm.
Figure 11:
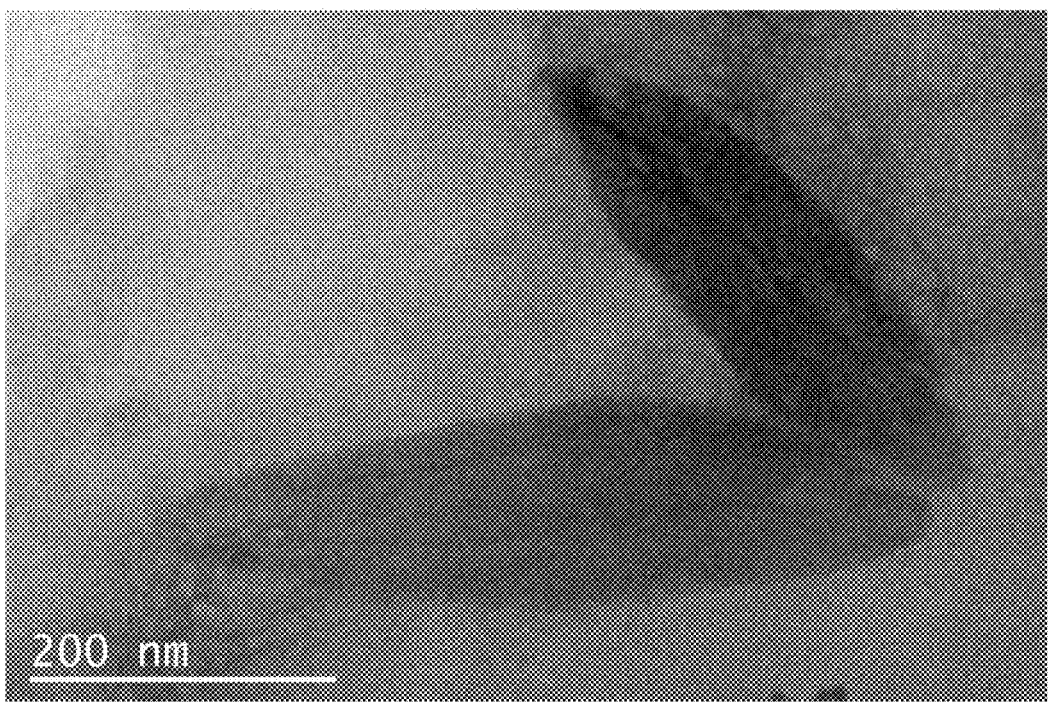
FIG. 11 is a transmission electron microscope image of the nanoparticles formed from the PIC-COS-$CaCl_2$ complex and TPP according to an embodiment of the disclosure; scale bar=200 m.

COS was dissolved in a phosphate buffer solution, and a solution of PIC in TPP was prepared according to the method of Example 1. The solution of PIC in TPP was slowly added dropwise into the COS solution under stirring, and then the calcium chloride solution was added dropwise. It can be seen from the transmission electron micrographs (FIG. 10, FIG. 11) that the formed nanoparticles are fusiform.

It can be found through Examples 5-8 that, surprisingly, the Pamica complex solution contains two states of substances at the same time, in which one is nanoparticles (the results of electron microscopy) and the other is non-nanoparticle (electrophoresis result of Example 3) solution.

The advantage of nanoparticles is that they may directly penetrate the cell membrane without endocytosis and enter the cell, and work quickly; non-nanoparticle solution can only enter the cell through endocytosis, and work more slowly than nanoparticles do. Pamica may exert its effect in two modes: endocytosis and directly entry into cells. In addition, more importantly, the nanoparticles has a structure that can protect Pamica from the degradation of PIC by ribonuclease in serum of primates and more advanced animals than primates, including human, in order to achieve a breakthrough in anti-viral and anti-tumor and have greater effects. These effects allow Pamica to have outstanding effects on the anti-cancer in humans and mice.

Experimental Example Evaluation of the Immune Effect of Pamica Complex

In the following experimental examples, the Pamica refers to the Pamica solution of PIC, COS and calcium chloride solution prepared according to Example 1, unless otherwise mentioned.

Experimental Example 1 Evaluation of the Immune Effect of Pamica Complex on Recombinant Hepatitis B Vaccine [rHBsAg (CHO)]

Materials: rHBsAg (CHO): 20 ug/ml; Pamica adjuvant: 1 mg/ml; ADV20 adjuvant: 400 ug/ml; aluminum hydroxide adjuvant: 10 mg/ml; saline.

Aluminum adjuvant/rHBsAg (CHO): aluminum adjuvant 0.07 ml+rHBsAg (CHO) 0.5 ml+saline 0.43 ml ADV20 (cytokine adjuvant)/rHBsAg (CHO): ADV20 0.25 ml+rHBsAg (CHO) 0.5 ml+saline 0.25 ml Pamica adjuvant/rHBsAg (CHO): Pamica adjuvant 0.5 ml+rHBsAg (CHO) 0.5 ml Method: mice were immunize intramuscularly with 0.1 ml of aluminum adjuvant/rHBsAg (CHO), ADV20 (cytokine adjuvant)/rHBsAg (CHO), Pamica/rHBsAg (CHO) on 0 day and on the $14^{th}$ day, respectively, and were detected for their cellular immunity and humoral immunity on the $21^{th}$ day.

Figure 12:
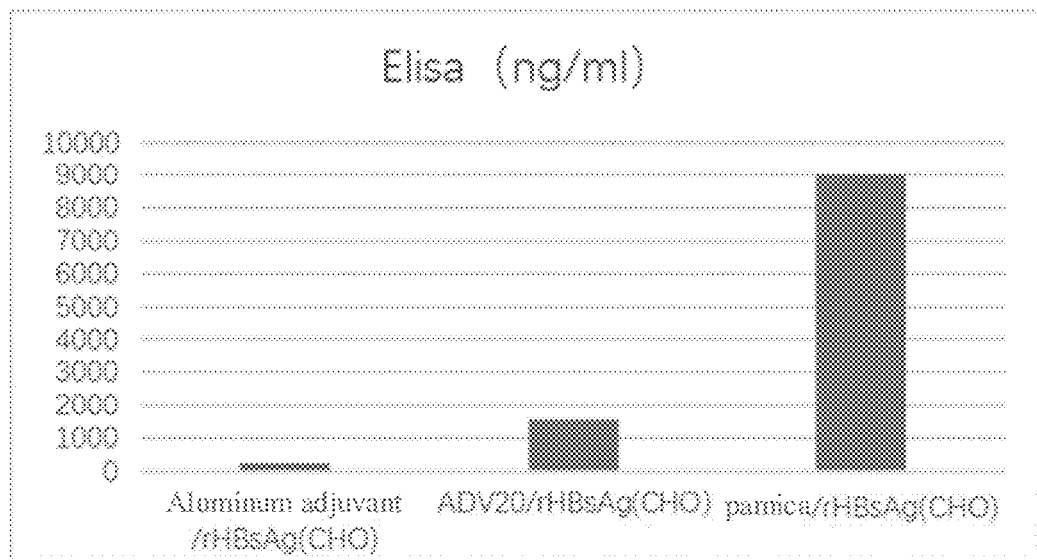
FIG. 12 is a detection graph of IgG antibodies detected by Elisa method in the serum of mice on the $21^{th}$ day after immunized with an aluminum adjuvant/rHBsAg (CHO), ADV20/rHBsAg (CHO) and Pamica/rHBsAg (CHO) respectively, according to an embodiment of the disclosure.
Figure 13:
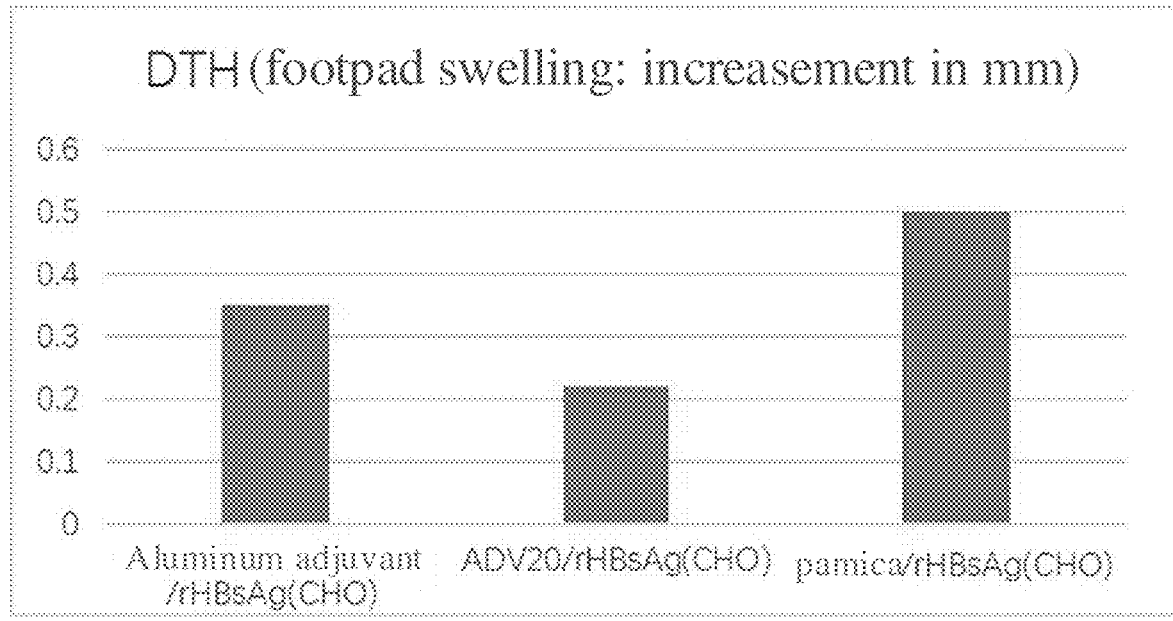
FIG. 13 is the humoral immunity of mice on the $21^{th}$ day after immunized with an aluminum adjuvant/rHBsAg (CHO), ADV20/rHBsAg (CHO) and Pamica/rHBsAg (CHO) respectively, according to an embodiment of the disclosure; the ordinate shows footpad swelling: mm increase.

Results: the Pamica complex of the present disclosure has outstanding immune effect; especially, the ELISA antibody and cellular immunity are greatly improved, which is significantly better than that of aluminum adjuvant and ADV20 (cytokine adjuvant). Pamica is a promising immune adjuvant, see FIG. 12 and FIG. 13 for details.

Experimental Example 2 Evaluation of the Immune Effects of Pamica Complex and Inactivated *Bacterium burgeri* Antigen Method: mice were immunized with PBS, polyinosinic-polycytidylic acid injection+inactivated *Bacterium burgeri* antigen, Pamica complex of the present disclosure+inactivated *Bacterium burgeri* antigen, respectively, immunized once at 0 day, and the mice were attacked using *Brucella* virulent strain after immunization for 45 days. After challenge for 15 days, the mice were killed to isolate the spleens of the mice, and the *Bacterium burgeri* in the spleen was cultured for 3 days, counted, and then the protective efficacy of the Pamica complex of the present disclosure+inactivated *Bacterium burgeri* antigen was evaluated.

| Groups Number of mouse | 1 | 2 | 3 | 4 | 5 | 6 | 7 | 8 | Mean value |
|---|---|---|---|---|---|---|---|---|---|
| Blank control group (log value) | 5.9 | 6.17 | 6.08 | 6.04 | 6.16 | 6.08 | 6.10 | 6.12 | 6.08 |
| polyinosinic-polycytidylic acid injection + inactivated *Bacterium burgeri* antigen (log value) | 5.16 | 5.18 | 3.97 | 3.54 | 4.37 | 4.2 | — | — | 4.4 |
| the Pamica complex of the present disclosure + inactivated *Bacterium burgeri* antigen (log value) | 2.59 | 2.78 | 3.32 | 3.11 | 2.88 | 2.9 | 3.81 | 3.02 | 3.05 |

Results: the Pamica complex of the present disclosure has outstanding immune effects and has prospect in the development of inactivated *Bacterium burgeri* antigens. The number of isolated bacterial using the Pamica complex of the present disclosure+inactivated *Bacterium burgeri* antigen differs by 3.03 logs from that using and the blank control group and differs by 1.35 from that using the polyinosinic-polycytidylic acid injection+inactivated *Bacterium burgeri* antigen. The Pamica complex and inactivated *Bacterium burgeri* has an outstanding protective effect.

Experimental Example 3 Use of the Pamica Complex and MYO Antigen (Human Myoglobin) in the Preparation of Antibodies Materials: MYO antigen (human myoglobin), with a concentration of 1 mg/ml The Pamica complex of the present disclosure, with a concentration of 1 mg/ml Complete Freund's adjuvant (CFA, Sigma)

Method: the negative blood from 2.3 kg-2.5 kg rabbits was collected and serum was separated as control before immunization. After different samples were subcutaneously injected in the abdomen and back at several sites, the serum was separated for antibody detection. The antigen+adjuvant was prepared in 0.5 ml+0.5 ml, and the dosage at each immunization was 1 ml.

Figure 14:
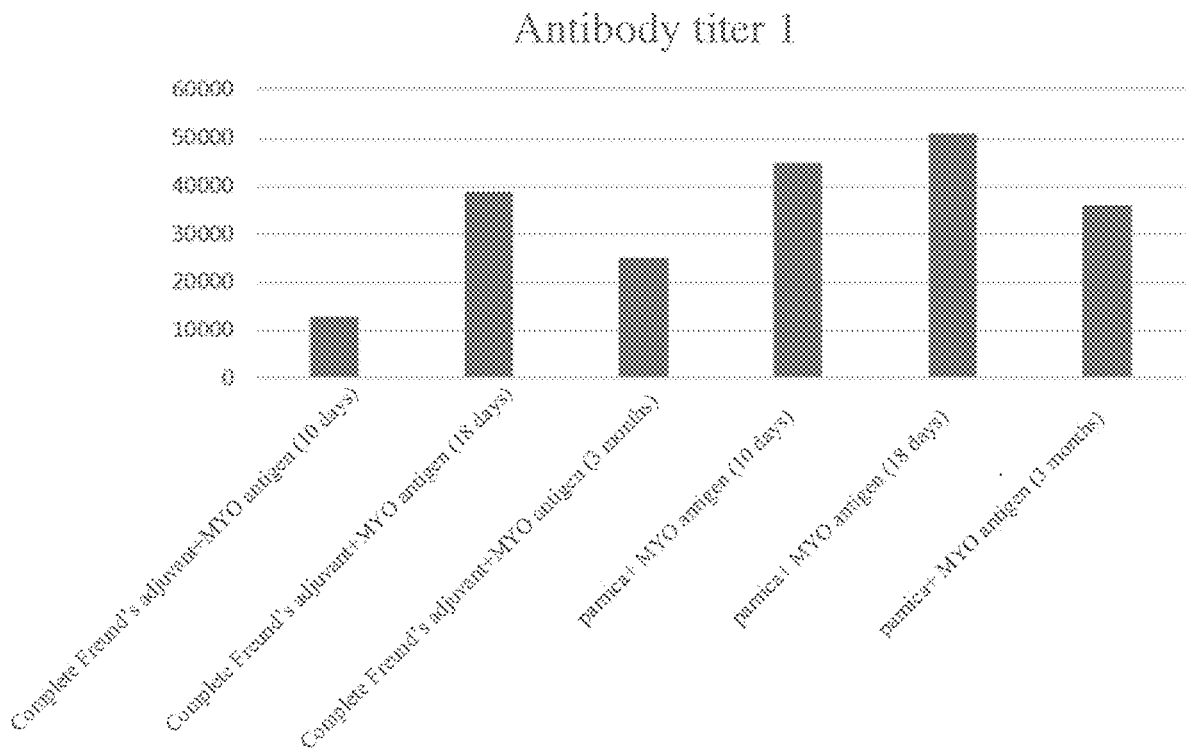
FIG. 14 is comparison of the effects of Pamica complex and complete Freund's adjuvant in the preparation of an antibody against the MYO antigen according to an embodiment of the present disclosure.

Results:

(1) Rabbits were immunized with the Pamica complex of the present disclosure+MYO antigen, complete Freund's adjuvant+MYO antigen once every 7 days. Complete Freund's adjuvant was added for immunization for 2 times (10 days), with an ELTSA antibody titer of 13,000; complete Freund's adjuvant was added for immunization for 3 times (18 days), with an ELTSA antibody titer of 39,000; complete Freund's adjuvant was added for immunization for 6 times (3 months), with an ELTSA antibody titer of 25,000; the Pamica complex of the present disclosure was added for immunization for 2 times (10 days), with an ELTSA antibody titer of 45,000, for immunization for 3 times (18 days), with an ELTSA antibody titer of 51,000, and for immunization for 3 times (3 months), with an ELTSA antibody titer of 36,000. Pamica adjuvant has a relatively high antibody titer in the early stage on MYO antigen and a better duration of immunization, indicating that the Pamica complex of the present disclosure is significantly better than complete Freund's adjuvant as the gold standard of immune adjuvant on MYO antigen, see FIG. 14 for details.

Figure 15:
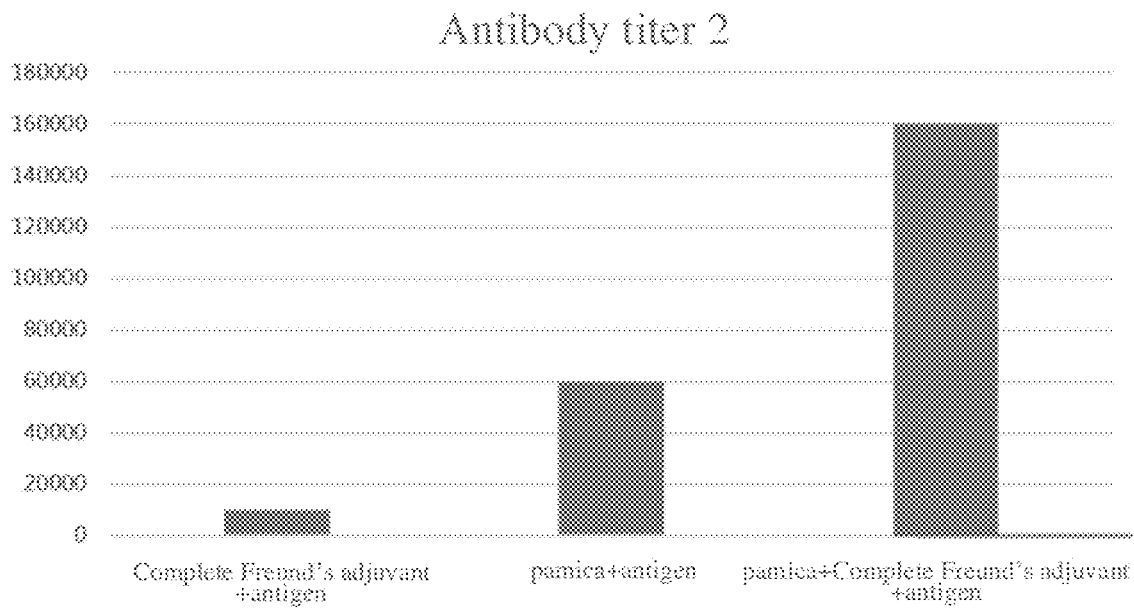
FIG. 15 is comparison of the effects of Pamica complex and complete Freund's adjuvant in the preparation of an antibody against the MYO antigen according to an embodiment of the present disclosure.

(2) rabbits were immunized for MYO antigen with the Pamica complex of the present disclosure combined with complete Freund's adjuvant twice (once immunized on 0 day, once immunized on the 14$^{th}$ day), the ELISA antibody titer (35 days after immunization) is 10.000, by using complete Freund's adjuvant. 60.000 by using Pamica complex of the present disclosure, and 160.000 by using Pamica complex of the present disclosure+complete Freund's adjuvant (FIG. 15).

Kits were prepared with antibodies produced by immunizing rabbits with complete Freund's adjuvant+antigen. Pamica adjuvant+complete Freund's adjuvant+antigen, and Pamica adjuvant+antigen, respectively. After clinical verification, the antibodies produced by complete Freund's adjuvant group or complete Freund's adjuvant+Pamica adjuvant antigen group do not match with clinical samples and cannot pass the clinical examination. Only antibodies produced by Pamica adjuvant+antigen can pass the clinical examination, which will completely break the Dutch Dako company's monopoly on the supply of antibody raw materials used in the human myoglobin latex turbidity kit, and solves the serious situation of common low immune titers, insufficient epitope diversity, and ineffective clinical sample detection when using complete Freund's adjuvant for domestic products.

The kits prepared with antibodies produced by using Pamica adjuvant+antigen group and the clinically used kits prepared with antibodies provided by Dutch Dako company are compared in the following table.

| Human serum | Chemiluminescence kit (prepared with an imported monoclonal antibody, high sensitivity) | CHUAN ZHI Latex kit from Chuanzhi Biotechnology | Latex kit from Homa Biological | Latex kit from JIEMEN Biotechnology | Pamica antigen group Latex kit |
|---|---|---|---|---|---|
| 1 | 35 | 25.44 | 12.48 | 17.09 | 55.54 |
| 2 | 24 | 35.59 | 17.66 | 9.12 | 37.48 |
| 3 | 186 | 130.11 | 88.6 | 71.33 | 79.17 |
| 4 | 1200 | 353.25 | 248.66 | OVER | 523.29 |
| 5 | 47 | 51.65 | 32.91 | 25.35 | 44.2 |
| 6 | 74 | 85.55 | 63.5 | 73.74 | 46.54 |
| 7 | 18 | 14.89 | 8.91 | 1.32 | 39.13 |
| 8 | 37 | 46.42 | 30.05 | 27.58 | 37.21 |
| 9 | 54 | 50.46 | 31.37 | 30.51 | 58.14 |
| 10 | 56 | 63.63 | 32.12 | 21.78 | 106.3 |

Experimental Example 4 Evaluation of NIH Efficacy of Pamica Complex on Rabies Vaccine Antigen Name: Evaluation of NIH efficacy of Pamica complex of the present disclosure on rabies vaccine antigen Method: mice were immunized with the Pamica complex of the present disclosure (1 mg/ml)+antigen, polyinosinic-polycytidylic acid injection (1 mg/m)+antigen PBS+antigen and antigen on 0 day challenged on the 14$^{th}$ day, and the potency was determined after 28 days.

Results: see the table below.

| | Preparation | | | | |
|---|---|---|---|---|---|
| Groups | the Pamica complex of the present disclosure (ml) | polyinosinic-polycytidylic acid injection (ml) | PBS (ml) | antigen (ml) | Results (IU/ml) |
| 1 | 0 | 0 | 0 | 1.0 | 3.5 |
| 2 | 0 | 0 | 0.8 | 0.2 | 1.0 |
| 3 | 0 | 0.8 | 0 | 0.2 | 2.0 |
| 4 | 0.8 | 0 | 0 | 0.2 | 3.6 |

The results show that:

a. the protective effect of the Pamica complex of the present disclosure+rabies vaccine antigen from CTN strain is 3.6 times that of the rabies vaccine antigen from CTN strain alone, and antigen is saved by ⅕;

b. the protective effect of the Pamica complex of the present disclosure+rabies vaccine antigen from CTN strain is 1.8 times that of the polyinosinic-polycytidylic acid injection+rabies vaccine antigen from CTN strain, and is outstanding.

Experimental Example 5 Pamica Complex Induces the Production of Multiple Cytokines in Mice Method: mice were immunized with the Pamica complex of the present disclosure and polyinosinic-polycytidylic acid injection. The mice eyeballs were removed at 1 hour, 2 hours, and 5 hours after immunization and blood was collected into a sterilized 2 ml centrifuge tube. The centrifuge tube was stood at room temperature for 30 minutes, centrifuged at 3500 rpm for 5 minutes. The supernatant was suck into a new centrifuge tube, and the serum was frozen at −20° C.

Results: the yields of cytokine TNF-α and IFN-γ induced by the Pamica complex of the present disclosure are obviously superior to that of polyinosinic-polycytidylic acid injection. The obtained data are all geometric average values, and the specific results are shown in the following table.

| Groups | Induce the production of cytokines | Tumor necrosis factor (TNF-α) pg/ml | Interferon (IFN-γ) pg/ml |
|---|---|---|---|
| Blank control | 0 h | 2 | 3 |
| polyinosinic-polycytidylic acid injection | 1 h | 12 | 4 |
| | 2 h | 5 | 38 |
| | 5 h | 13 | 258 |
| Pamica | 1 h | 863 | 32 |
| | 2 h | 331 | 71 |
| | 5 h | 143 | 285 |

Summary: TNF-α can kill and inhibit tumor cells, promote neutrophil phagocytosis, and resist infection, and it is a type of cytokine that can directly cause death of tumor cells; IFN-γ can induce cell resistance to viral infection, and by interfering with the transcription of viral genes or the translation of viral protein components, IFN-γ can prevents from or limits viral infections, and is currently the most important anti-viral infection and anti-tumor cytokine.

The levels of produced TNF-α and IFN-γ cytokines induced by Pamica in mice are higher than those induced by polyinosinic-polycytidylic acid injection, indicating that the produced TNF-α and IFN-γ induced by the Pamica complex of the present disclosure have more powerful ability of killing tumor cells and anti-infection synergistically.

Experimental Example 6 Examination of Abnormal Toxicity

1. The Test of the Pamica Complex of the Present Disclosure in Mice:

1.1 Test:

Sample injection: 18 g~22 g healthy SPF mice from Kunming were intraperitoneally injected at 0.5 ml/mouse and 5 mice/sample, and 5 healthy mice as blank controls were weighed at 18 g~22 g at the same time.

1.2 Criteria:

Each mouse is intraperitoneally injected with 0.5 ml of the test substance and observed for 7 days. During the observation, all the mice should survive without abnormal reactions. When the time expires, each mouse should gain weight, and then the test substance is deemed qualified. If the above requirements are not met, 10 mice may be used for one retest, and the criteria are the same as the above (ip. is short for intraperitoneal injection).

1.3. Results

| Serial Nos | Body weight before injection | Injection Dosage | Route | 1 | 2 | 3 | 4 | 5 | 6 | 7 | Body weight after injection | Results |
|---|---|---|---|---|---|---|---|---|---|---|---|---|
| Pamica parallel sample 1 (prepared with PIC heated for 120 minutes) | 20.2 g | 0.5 ml/ mouse | ip. | survived | survived | survived | survived | survived | survived | survived | 33.7 g | qualified |
| Pamica parallel | 20.3 g | 0.5 ml/ mouse | ip. | survived | survived | survived | survived | survived | survived | survived | 32.6 g | qualified |

-continued

| Serial Nos | Body weight before injection | Injection Dosage | Route | 1 | 2 | 3 | 4 | 5 | 6 | 7 | Body weight after injection | Results |
|---|---|---|---|---|---|---|---|---|---|---|---|---|
| sample 2 (prepared with PIC heated for 120 minutes) | | | | | | | | | | | | |
| Pamica parallel sample 3 (prepared with PIC heated for 120 minutes) | 21.4 g | 0.5 ml/ mouse | ip. | survived | survived | survived | survived | survived | survived | survived | 33.4 g | qualified |
| Pamica parallel sample 4 (prepared with PIC heated for 120 minutes) | 19.3 g | 0.5 ml/ mouse | ip. | survived | survived | survived | survived | survived | survived | survived | 27.3 g | qualified |
| Pamica parallel sample 5 (prepared with PIC heated for 120 minutes) | 21.2 g | 0.5 ml/ mouse | ip. | survived | survived | survived | survived | survived | survived | survived | 31.3 g | qualified |
| Pamica parallel sample 1 (prepared with unheated PIC) | 20.9 g | 0.5 ml/ mouse | ip. | survived | survived | survived | survived | survived | survived | survived | 32.1 g | qualified |
| Pamica parallel sample 2 (prepared with unheated PIC) | 20.4 g | 0.5 ml/ mouse | ip. | survived | survived | survived | survived | survived | survived | survived | 32.2 g | qualified |
| Pamica parallel sample 3 (prepared with unheated PIC) | 19.9 g | 0.5 ml/ mouse | ip. | survived | survived | survived | survived | survived | survived | survived | 29.8 g | qualified |
| Pamica parallel sample 4 (prepared with unheated PIC) | 20.1 g | 0.5 ml/ mouse | ip. | survived | survived | survived | survived | survived | survived | survived | 30.7 g | qualified |
| Pamica parallel sample 5 (prepared with unheated PIC) | 19.7 g | 0.5 ml/ mouse | ip. | survived | survived | survived | survived | survived | survived | survived | 30.6 g | qualified |
| PBS parallel sample 1 | 20.6 g | 0.5 ml/ mouse | ip. | survived | survived | survived | survived | survived | survived | survived | 33.7 g | qualified |
| PBS parallel sample 2 | 19.8 g | 0.5 ml/ mouse | ip. | survived | survived | survived | survived | survived | survived | survived | 31.9 g | qualified |
| PBS parallel sample 3 | 19.2 g | 0.5 ml/ mouse | ip. | survived | survived | survived | survived | survived | survived | survived | 30.2 g | qualified |
| PBS parallel sample 4 | 21.3 g | 0.5 ml/ mouse | ip. | survived | survived | survived | survived | survived | survived | survived | 31.5 g | qualified |
| PBS parallel sample 5 | 19.2 g | 0.5 ml/ mouse | ip. | survived | survived | survived | survived | survived | survived | survived | 27.8 g | qualified |

2 The Test of Pamica Complex of the Present Disclosure in Guinea Pigs:

2.1 Test:

Sample injection: 250 g~350 g healthy SPF grade Hartely guinea pigs were intraperitoneally injected at 5 mi/guinea pig and 2 guinea pigs/sample and 2 healthy guinea pigs as blank controls were weighed at 250 g~350 g at the same time.

2.2 Criteria:

Each guinea pig is intraperitoneally injected with 5 ml of the test substance and observed for 7 days. During the observation, all the guinea pigs should survive without abnormal reactions. When the time expires, each guinea pig should gain weight, and then the test substance is deemed qualified. If the above requirements are not met, 4 guinea pigs may be used for one retest, and the criteria are the same as the above.

2.3. Test Results:

| Serial Nos | Body weight before injection | Injection Dosage | Injection Route | Observation days, abnormal reactions and deaths 1 | 2 | 3 | 4 | 5 | 6 | 7 | Body weight after injection | Results |
|---|---|---|---|---|---|---|---|---|---|---|---|---|
| Pamica parallel sample 1 (prepared with PIC heated for 120 minutes) | 271 g | 5 ml/guinea pig | ip. | survived | survived | survived | survived | survived | survived | survived | 295 g | qualified |
| Pamica parallel sample 2 (prepared with PIC heated for 120 minutes) | 263 g | 5 ml/guinea pig | ip. | survived | survived | survived | survived | survived | survived | survived | 301 g | qualified |
| Pamica parallel sample 1 (prepared with PIC heated for 90 minutes) | 276 g | 5 ml/guinea pig | ip. | survived | survived | survived | survived | survived | survived | survived | 298 g | qualified |
| Pamica parallel sample 2 (prepared with PIC heated for 90 minutes) | 296 g | 5 ml/guinea pig | ip. | survived | survived | survived | survived | survived | survived | survived | 326 g | qualified |
| Pamica parallel sample 1 (prepared with PIC heated for 70 minutes) | 266 g | 5 ml/guinea pig | ip. | survived | survived | survived | survived | survived | survived | survived | 297 g | qualified |
| Pamica parallel sample 2 (prepared with PIC heated for 70 minutes) | 273 g | 5 ml/guinea pig | ip. | survived | survived | survived | survived | survived | survived | survived | 302 g | qualified |
| Complex parallel sample 1 (prepared with PIC heated for 60 minutes) | 263 g | 5 ml/guinea pig | ip. | loose hair, loss of appetite, listlessness | | | | | died, weight of 230 g | | | unqualified |
| Complex parallel sample 2 (prepared with PIC heated for 60 minutes) | 277 g | 5 ml/guinea pig | ip. | loose hair, loss of appetite, listlessness died | | | | | died, weight of 246 g | | | unqualified |
| Complex parallel sample 1 (prepared with PIC heated for 50 minutes) | 287 g | 5 ml/guinea pig | ip. | loose hair, loss of appetite, listlessness died | | | | | died, weight of 234 g | | | unqualified |
| Complex parallel sample 2 (prepared with PIC heated for 50 minutes) | 293 g | 5 ml/guinea pig | ip. | loose hair, loss of appetite, listlessness died | | | | | died, weight of 268 g | | | unqualified |
| Complex parallel sample 1 | 280 g | 5 ml/guinea pig | ip. | loose hair, loss of appetite, listlessness | | | | | died, weight of 258 g | | | unqualified |

| Serial Nos | Body weight before injection | Injection Dosage | Route | Observation days, abnormal reactions and deaths 1 | 2 | 3 | 4 | 5 | 6 | 7 | Body weight after injection | Results |
|---|---|---|---|---|---|---|---|---|---|---|---|---|
| (prepared with unheated PIC) Complex parallel sample 2 (prepared with unheated PIC) | 290 g | 5 ml/ guinea pig | ip. | loose hair, loss of appetite, listlessness | | | | | died, weight of 265 g | | | unqualified |
| PBS parallel sample 1 | 288 g | 5 ml/ guinea pig | ip. | survived | survived | survived | survived | survived | survived | survived | 308 g | qualified |
| PBS parallel sample 2 | 301 g | 5 ml/ guinea pig | ip. | survived | survived | survived | survived | survived | survived | survived | 334 g | qualified |

Note:
the retest was still unqualified.

3 The Test of Pamica Complex of the Present Disclosure+ Purified Rabies Vaccine Antigen in Guinea Pigs:

3.1 Test:

Sample injection: 250 g~350 g healthy SPF grade Hartley guinea pigs were intraperitoneally injected at 5 ml/guinea pig and 2 guinea pigs/sample, and 2 healthy guinea pigs as blank controls were weighed at 250 g~50 g at the same time.

3.2 Criteria:

Each guinea pig is intraperitoneally injected with 5 ml of the test substance and observed for 7 days. During the observation, all the guinea pigs should survive without abnormal reactions. When the time expires, each guinea pig should gain weight, and then the test substance is deemed qualified. If the above requirements are not met, 4 guinea pigs may be used for one retest, and the criteria are the same as the above.

3.3. Test Results:

| Serial Nos | Body weight before injection | Injection Dosage | Route | Observation days, abnormal reactions and deaths 1 | 2 | 3 | 4 | 5 | 6 | 7 | Body weight after injection | Results |
|---|---|---|---|---|---|---|---|---|---|---|---|---|
| Pamica (prepared with PIC heated for 120 minutes) + purified rabies vaccine antigen 1 | 281 g | 5 ml/ guinea pig | ip. | survived | survived | survived | survived | survived | survived | survived | 303 g | qualified |
| Pamica (prepared with PIC heated for 120 minutes) + purified rabies vaccine antigen 2 | 273 g | 5 ml/ guinea pig | ip. | survived | survived | survived | survived | survived | survived | survived | 316 g | qualified |
| Complex (prepared with PIC heated for 60 minutes) + purified rabies vaccine antigen 1 | 275 g | 5 ml/ guinea pig | ip. | loose hair, loss of appetite, listlessness | | | | | | | 238 g | unqualified |
| Complex (prepared with PIC heated for 60 minutes) + purified rabies vaccine antigen 2 | 302 g | 5 ml/ guinea pig | ip. | loose hair, loss of appetite, listlessness | | | | died | | | died, body weight of 266 g | unqualified |

| Serial Nos | Body weight before injection | Injection Dosage | Route | 1 | 2 | 3 | 4 | 5 | 6 | 7 | Body weight after injection | Results |
|---|---|---|---|---|---|---|---|---|---|---|---|---|
| | | | | | | Observation days, abnormal reactions and deaths | | | | | | |
| PBS parallel sample 1 | 293 g | 5 ml/guinea pig | ip. | survived | survived | survived | survived | survived | survived | survived | 328 g | qualified |
| PBS parallel sample 2 | 314 g | 5 ml/guinea pig | ip. | survived | survived | survived | survived | survived | survived | survived | 340 g | qualified |

Note:
1) the retest was still unqualified;
2) purified rabies vaccine antigen: cell: Vero cell; virus strain: CTN strain (this is not intended to just limited to Vero cell and CTN strain virus strain).

4 The Test of Pamica Complex of the Present Disclosure+Hepatitis B Vaccine Antigen in Guinea Pigs:

4.1 Test:

Sample injection: 250 g~350 g healthy SPF grade Hartely guinea pigs were intraperitoneally injected at 5 ml/guinea pig and 2 guinea pigs/sample, and 2 healthy guinea pigs as blank controls were weighed at 250 g~350 g at the same time.

4.2 Criteria:

Each guinea pig is intraperitoneally injected with 5 ml of the test substance and observed for 7 days. During the observation, all the guinea pigs should survive without abnormal reactions. When the time expires, each guinea pig should gain weight, and then the test substance is deemed qualified. If the above requirements are not met, 4 guinea pigs may be used for one retest, and the criteria are the same as the above.

4.3 Test Results:

| Serial Nos | Body weight before injection | Injection Dosage | Route | 1 | 2 | 3 | 4 | 5 | 6 | 7 | Body weight after injection | Results |
|---|---|---|---|---|---|---|---|---|---|---|---|---|
| | | | | | | Observation days, abnormal reactions and deaths | | | | | | |
| Pamica (prepared with PIC heated for 120 minutes) + hepatitis B vaccine antigen 1 | 263 g | 5 ml/guinea pig | ip. | survived | survived | survived | survived | survived | survived | survived | 299 g | qualified |
| Pamica (prepared with PIC heated for 120 minutes) + hepatitis B vaccine antigen 2 | 259 g | 5 ml/guinea pig | ip. | survived | survived | survived | survived | survived | survived | survived | 294 g | qualified |
| Complex (prepared with PIC heated for 60 minutes) + hepatitis B vaccine antigen 1 | 265 g | 5 ml/guinea pig | ip. | | | loose hair, loss of appetite, listlessness | | | | | 229 g | unqualified |
| Complex (prepared with PIC heated for 60 minutes) + hepatitis B vaccine antigen 2 | 272 g | 5 ml/guinea pig | ip. | | | loose hair, loss of appetite, listlessness | | | died, body weight of 246 g | | | unqualified |
| PBS parallel sample 1 | 288 g | 5 ml/guinea pig | ip. | survived | survived | survived | survived | survived | survived | survived | 318 g | qualified |
| PBS parallel sample 2 | 294 g | 5 ml/guinea pig | ip. | survived | survived | survived | survived | survived | survived | survived | 326 g | qualified |

Note:
1) the retest was still unqualified;
2) hepatitis B vaccine antigen: yeast expressed (this is not intended to just limited to yeast expressed, and recombinant CHO engineered cells may also be used to express hepatitis B antigen).

Summary and Analysis:

PIC (double-stranded nucleic acid) unwinds after being heated at a certain temperature and the two single strands are paired via hydrogen bonds with the temperature slowly decreasing to restore the double strand. Heating can reduce the molecular weight of PIC and reduce its toxicity. If PIC is unheated or prepared without being heated for enough time, the complex prepared by this method is very toxic itself, and the vaccine prepared by this complex is also very toxic, which it is difficult to put into use.

Experimental Example 7 the Use of Pamica Complex in Some Advanced Cancer Patients and for Infection Treatment

| Name | Gender | Age | Disease | Before administration | After administration | Administration time |
|---|---|---|---|---|---|---|
| XX Lin | Female | 80 years old | 2016.5. metastasis occured in multiple organs after 2 operations of submandibular gland carcinoma. A survival period of 1-2 months was expected by a doctor. | Bedridden, nausea, vomiting, only one meal every day, listlessness, life support by blood transfusion and protein. | Since October 2016, appetite had gradually increased, with 3 meals a day, gained weight, and good mental state. The survival period is longer than the doctor reckoned and extended to 14 months (July 2016~September 2017). After intramuscular injection, the patient was administrated at 4 mg each time. Since the injection site was painful and indurated, and then nasal spray administration was applied at 4 mg-6 mg each time. | June 2016-July 2017, the patient died of relapse in July 2017, 2 months after stopping the drug |
| XX Wen | male | 67 years old | Lung adenocarcinoma, diagnosed as lung cancer in Peking Union Medical College Hospital and Tianjin Quanjian Hospital in February 2017 and March 2017, respectively. There was a duck egg-sized tumor in the mediastinum. | listlessness, received chemotherapy without surgery. | The patient was nasal spray administered at 6 mg each time, once every day without side effects. The mucosal immune formulation combined with a chemotherapy drug (cisplatin) has reduced side effects, with baraly any nausea and vomiting, and the white blood cells increased from $1000/mm^3$-$2000/mm^3$ when taking no drug to more than $3000/mm^3$. | March 2017-June 2017, the patient's family took the drug proactively in October 2017 (alive). |
| XX Zhu | Female | 62 years old | The patient was diagnosed with right breast cancer with multiple metastatic carcinoma in the liver, and cancer cells nests within fibrous tissue observed in the lymph gland, diagnosed by Jilin Provincial Tumor Hospital on May 8, 2017. | serious side effects after two chemotherapies, weight loss, nausea and vomiting, growing tumor and high transaminase. | , The patient was administered once every other day from May 4, 2017, with first nasal spray administration at 4 mg every time and then intramuscularly injection at 2 mg every time. After more than 10 such cycle of administration, the patient reported no side effects. Combination with chemotherapy drugs significantly reduced the side effects of chemotherapy with increased Diet, greater physical strength, and softer breast masses. The glutamic-pyruvic transaminase decreased from 130.5 U/L to 38.4 U/L. The liver maximum hypoechoic halo reduced from 7.6 cm × 5.1 cm on Apr. 9, 2017 to 5.9 cm × 3.0 cm Jun. 2, 2017. | May 2017-August 2017, XX Zhu reported a significant improvement in the quality of life. She died soon of liver failure due to smoking after returning to her hometown in Northeast China. |
| XX Wang | Female | 73 years old | Being subjected to colon cancer surgery in 2002, breast cancer surgery in 2008, lung cancer surgery in 2015, and radiotherapy and chemotherapy for lung cancer in April 2017. | No appetite, no taste, light sleep, fatigue and weakness, mild hair loss, poor gastric motility, coughing and taking cough drug, no treatment. | The patient was administered every other day from May 27, 2017, with nasal spray administration at 4 mg every time. After 6 administrations, the patient and her family reported no side effects, increased diet, reduced tumors, and obvious relief of cough, and stopped taking cough drug. Laboratory results on Mar. 29, 2018: 1) the level of carcinoembryonic antigen is 1.93, reference value is 0 ng/ml-5 ng/ml; 2) the level of carbohydrate antigen CA153 is 9.2, reference | May 2017-present (alive) |

-continued

| Name | Gender | Age | Disease | Before administration | After administration | Administration time |
|---|---|---|---|---|---|---|
| | | | | | value is 0 IU/ml-25 IU/ml; 3) the level of carbohydrate antigen CA-125 is 1.2 U/ml, reference value is 0 U/ml-35 U/ml; 4) the level of carbohydrate antigen CA19-9 is 6.24, reference value <39 U/ml; 5) the level of carbohydrate antigen CA-724 is 0.72, reference value is 0 U/ml-6.9 U/ml; 6) the level of neuron specific enolase is 12.36, reference value is 0 ng/ml-16.3 ng/ml; 7) the level of fecal occult blood is 0, reference value <100 ng/ml. | |
| XX Gao | Female | 72 years old | Laryngeal cancer; no any medication after the surgery in 2014, and replase in early 2016. | Lack of physical strength (activity within a limited range), tiredness, loss of appetite, dyspnea, easy to awake by choke when sleeping. | The patient was administered at 2 mg every other two days by intramuscular injection. After half a month, the fatigue symptom alleviated, the patient could go to the market, with increased appetite, relieved dyspnea was, and good sleeping. The patient felt significantly better and well tolerated, no obvious adverse reactions, and gave up taking analgesics. The patient was then administered intratumorally every other two days at 2 mg injection each time to the tumor in skin surface. After 7 injections, the tumor in skin surface disappeared after suppuration. | April 2016-January 2017 (Died) |
| XX Bai | male | 59 years old | Esophageal cancer; cancer was found in the prison around June 2016, and the patient was brought back to the village by the Su Village Committee from the prison. The patient did not receive any treatment and dictated the cancer as benign tumor. | Sweating, fatigue, loss of appetite (only 1 egg custard consumption), dyspnea, and systemic discomfort. | The patient was intramuscular injected once at 2 mg every other day, half a month after the first administration, appetite greatly increased (the patient can eat 7 or 8 egg custard, and can drink alcohol), and gained weight. The patient felt significantly better, with improved spiritual outlook, no fever, no diarrhea, no obvious adverse reactions, no fever in hands and feet, normal body temperature, no sweating, and no pain at the injection site. | August 2016-February 2017, died in 2 months after stopping taking the drug. |
| XX Zheng | male | 48 years old | Liver cancer; one third of his liver was cut off, the bile was removed, and the patient took analgesics. | Lack of physical strength (activity within a limited range), tiredness, loss of appetite. | The patient was intramuscular injected once at 2 mg every other day. 4 days after the first administration, the patient had relieved fatigue symptom, increased physical strength, and stopped taking medicine. A few days later, the patient continued to take medicine, with relieved pain symptom. The patient then gave up taking analgesics, and appetite increased. | September 2016-January 2017 (alive) |
| XX Qi | male | 50 years old | Lung cancer discovered in 2016, no treatment, only took anti-inflammatory and analgesic drugs. | Bedridden, lack of physical strength (the patient could walk with a crutch and support), skinny (50 catty), fatigue, loss of | The patient was intramuscular injected once at 2 mg every other day. Half a month after the first administration, the patient had relieved fatigue symptom, could walk to the outside of court without the crutch, with increased appetite, but no significantly relieved pleural fluid. Fever (no temperature measurement) and diarrhea occurred after | August 2016-October 2016 (died) |

-continued

| Name | Gender | Age | Disease | Before administration | After administration | Administration time |
|---|---|---|---|---|---|---|
| XX Zhao | Female | 63 years old | Breast cancer; two chemotherapy after surgery. | appetite, dyspnea, about half a catty pleural fluid per day. Multiple metastases to lung, liver, and bone, nausea, anorexia | administration. Pamica was administered once every other day since early May 2017, with nasal spray administration at 3.6 mg each time. The patient had no side effects, normal diet, and good physical strength. The patient had extremely high transaminase before taking Pamica and could not be subjected to chemotherapy, but she had normal transaminase after the administration, and accepted the third chemotherapy. One month later, the hospital reported that the liver metastatic cancer reduced from 7.5 cm × 5.3 cm to 5.9 cm × 3.5 cm. On July 18, the hospital informed by phone that the liver tumor had shrunk to about 5 cm, and the patient felt like a normal person (hospital test report). | May 2017-present (Alive) |
| XX Ji | male | 64 years old | The Patient was diagnosed with an advanced lung cancer on Nov. 13, 2017 by Peking University Third Hospital | Systemic multiple bone metastases, pneumonia, pulmonary embolism, etc., Cytokaratin 19, (i.e. CYFRA21-1) at 3.04 ng/ml, carcinoembryonic antigen at 298.50 ng/ml, and lymphadenectasis., The patient suffered from pain in back, buttock and sacrococcygeal region. After hospitalization, dolantin was increasing day by day to 5 needles/day for pain relief but failed. | Pamica nasal spray was nasal spray administrated once at 3.6 mg every other day sinc Nov. 14, 2017 (the weight of the patient is 90 kg). Gefitinib was taken orally at 1 tablet/day at the same time. After 10 days, the pain disappeared day by day. Dolantin was reduced at 1 needle/day, until dolantin was not administrated at all, and the pain disappeared completely. The level of carcinoembryonic antigen (2017 Dec. 1) was 174.50 ng/ml (298.50 ng/ml before administration). CT image report sheet on Dec. 7, 2017: multiple nodule shadows less than 5 mm in both lungs, lamellar increased density shadow in the inferior lobe of left lung, with clear boundary, unobstructed openings of the trachea and bronchi, and no mediastinal lymphadenectasis. Imaging diagnosis: small nodule shadows in both lungs, follow-up observation was recommended, chronic inflammation in the left lower lung. | November 2017-present (alive) |
| XX Lin | male | 73 years old | Pharyngitis | Pharyngalgia, accompanied by cough, yellow sputum, purulent nasal discharge | The pharynx was sprayed with Pamica, the pharyngalgia and cough improved significantly after a few times, and healed in about 3 days. The patient was absolved from antibiotics that must be taken in the past and had no side effects. | Nov. 20, 2017-Nov. 22, 2017 |

From many cases with advanced cancer, it can be seen that the present product can be administered through nasal spray in addition to the injected administration route and has a significant effect on metastatic cancer.

(1) Good safety, no obvious side effects; Pamica immune formulation is a non-cytotoxic drug;

(2) reduced side effects of radiotherapy and chemotherapy: the number of white blood cells and serum protein content increases;

(3) Significant clinical effects: pain relief, increased appetite, increased physical strength, spirit changing from pessimism to optimism, confidence, extended overall survival by several months and by 13 months for some cases;

(4) Significantly reduced size of metastatic cancer, by ⅓-½ for some cases.

Test Example 8: Stability Tests

After the production of the Pamica complexes of the present disclosure were completed, they were stored indoors in the dark, and the samples were tested every 6 months

| Test Item | polyinosinic-polycytidylic acid injection | Pamica Lot P-20170801 | | Pamica Lot P-20170801 | |
|---|---|---|---|---|---|
| Storage Conditions | store in a cool and dark place (not exceeding 20° C.) | store at room temperature for 0 month | store at room temperature for 6 months | store at room temperature for 0 month | store at room temperature for 6 months |
| Character | clear solution | clear solution | clear solution | clear solution | clear solution |
| Fluorescence reaction | fluorescence increasing | fluorescence increasing | fluorescence increasing | fluorescence increasing | fluorescence increasing |
| pH | 6.8 | 6.66 | 6.51 | 6.85 | 6.48 |
| Hyperchromic effect | 58.1% | 70.5% | 65.7% | 71.0% | 67.7% |
| Molecular weight | 25 kD–500 kD | 100 bp-1500 bp | 100 bp-1500 bp | 100 bp-1500 bp | 100 bp-1500 bp |
| Content | 94.2% | 95.8% | 102.3% | 91.3% | 95.3% |
| Sterility test | qualified | qualified | qualified | qualified | qualified |
| Bacterial endotoxin | >100 EU/ml | <10 EU/ml | <10 EU/ml | <10 EU/ml | <10 EU/ml |

Results: the samples were stored at room temperature (the room temperature was over 30 degrees from August to September in Beijing) within 6 months, and the test indexs of the products did not significantly change, indicating that the products were relatively stable; Pamica prepared at 1 mg/ml may stabilize for at least 12 months; Pamica prepared at 3 mg/ml of may stabilize for at least 9 months. The pH of the products is relatively stable, and does not significantly change within 3 years. The bacterial endotoxin of Pamica of the present disclosure is less than 10 EU/ml, while the bacterial endotoxin of polyinosinic-polycytidylic acid injection is greater than 100 EU/ml. As it is the common technology in the art that, bacterial endotoxin is the cell wall component of gram-negative bacteria, a bacteria will releases endotoxins after it dies or autolyzes. Therefore, bacterial endotoxin is widely found in nature. For example, the endotoxin contained in tap water has an amount from 1 EU/ml to 100 EU/ml. When bacterial endotoxin was introduced into human body through the digestive tract, it is harmless, but when endotoxin enters the blood through injection or other ways, it can cause different diseases. After a small amount of endotoxin enters the blood, it is inactivated by Kupffer cells of the liver and is harmless to the human body. A large amount of endotoxin enters the blood will cause a fever reaction, i.e. "pyrogen reaction". Therefore, formulation such as biological products, injection medicaments, chemicals, radiopharmaceuticals, antibiotics, vaccines, dialysate and the like, as well as medical equipments (such as disposable syringes, implantable biological materials) must pass verified via the bacterial endotoxin test to be qualified before use.

Experimental Example 9 the Determination of Pamica Promoting the Phagocytic Function of Macrophage Location: Institute of Materia *Medica*, Chinese Academy of Medical Sciences Method: collection of macrophages: 6 SPF grade Kunming mice of 20 g-25 g were randomly divided into 2 groups with 3 mice in each group. The mice were immunized with Pamica and PBS on 0 day, each mouse was nasal dripped at 200 μL. 2 hours later, each mouse was injected with 5.0% chicken red blood cells in 0.85% saline suspension. 4 hours later, 3 mice in each mice group were sacrificed by dislocation. After disinfection, the skin was cut and Hanks buffer was peritoneally injected at 2.5 mL/mouse, and the abdomen of the mouse was gently rubbed to make the Hanks buffer fully wash the macrophages in the abdominal cavity. Then a small hole was cut in the middle of the peritoneum, and about 2 mL of liquid in the abdominal cavity was sucked using a 5 mL pipette and placed in a test tube.

Slide dropping: the peritoneal lotion was aseptically suck out from the test tube, and dropped on a glass slide. The dropping slide was horizontally put on a wet gauze. The slide was incubated in a constant temperature incubator at 37° C. for half an hour and at this time; a large number of macrophages were adhered to the glass slide. The chicken red blood cells and other tissue cells on the glass slide that have not been phagocytized were washed off with 0.85% saline, then the glass slide was dried in cold air.

Fixation and staining of specimens: the specimens were fixed with methanol for 5 minutes and stained with Giemsa-Wright staining solution. The staining was carried out according to Giemsa's staining method, and the PBS buffer used was adjusted to the pH of 6.5. The specimens were observed and calculated with an oil immersion lens after drying in cold air.

Percentage of phagocytosis: the total number of macrophages that phagocytize red blood cells÷the total number of macrophages×100%.

Phagocytosis index: the total number of red blood cells phagocytized by macrophages÷the total number of macrophages that phagocytize red blood cells×100% (100 macrophages were observed under an oil immersion lens, and the value, which is obtained by counting the numbers of red blood cells phagocytized by each macrophage, summing the numbers up and dividing the obtained sum by 100, is the phagocytic index).

Figure 16:
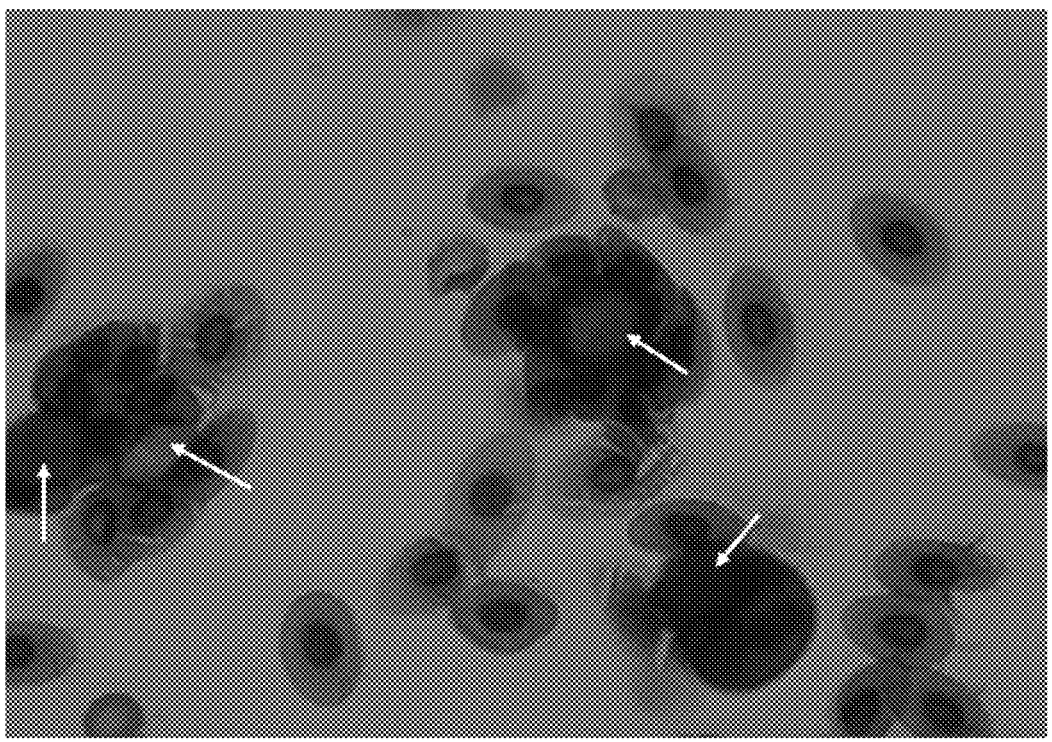
FIG. 16 is an exemplary picture of an experiment in which the Pamica group stimulates the phagocytic function of macrophage according to an embodiment of the present disclosure.
Figure 17:
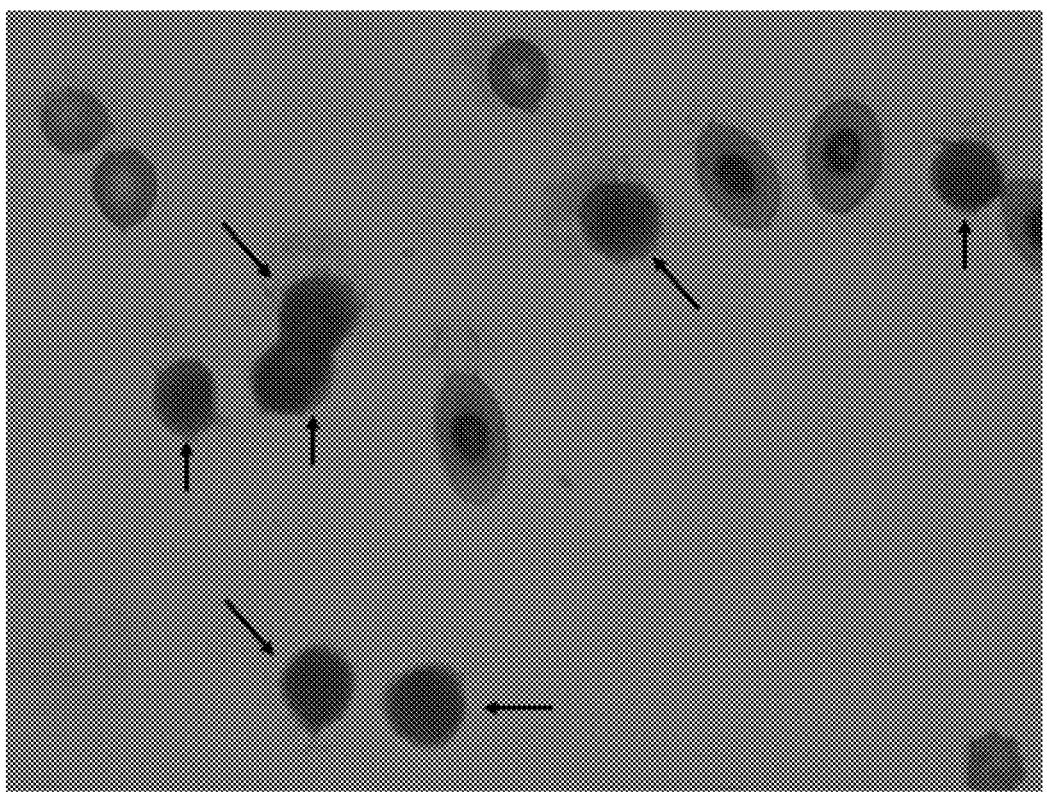
FIG. 17 is an exemplary picture of an experiment in which the PBS control group does not stimulate the phagocytic function of macrophage according to an embodiment of the disclosure.
Figure 18:
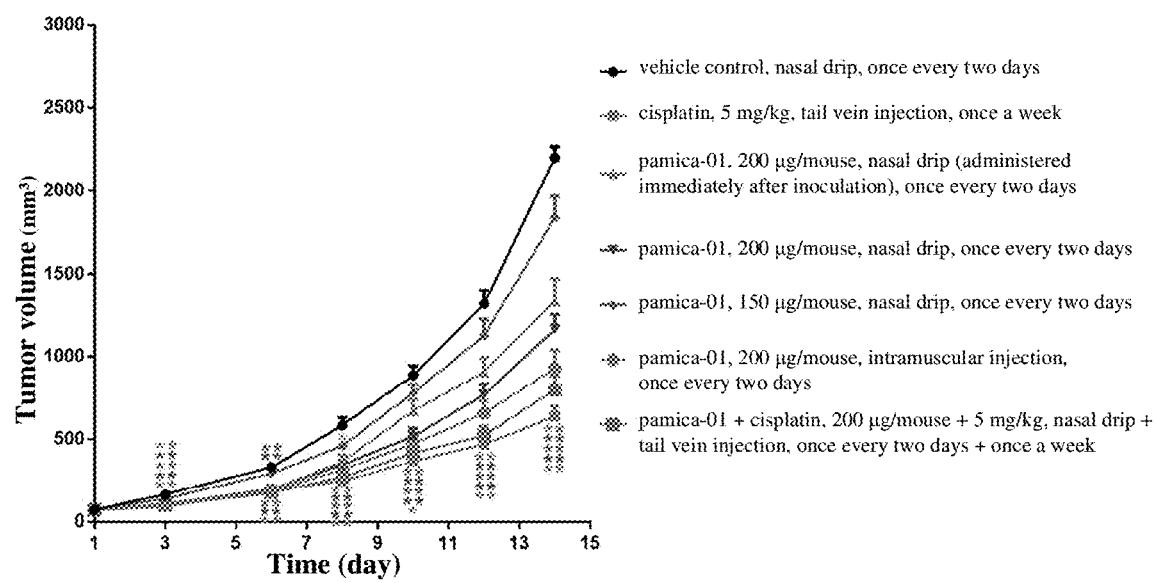
FIGS. 18-21 are experimental results of the anti-cancer effects of Pamica mucosal immune formulation in the tumor-bearing mouse model of LL2 lung cancer according to an embodiment of the present disclosure.
Figure 19:
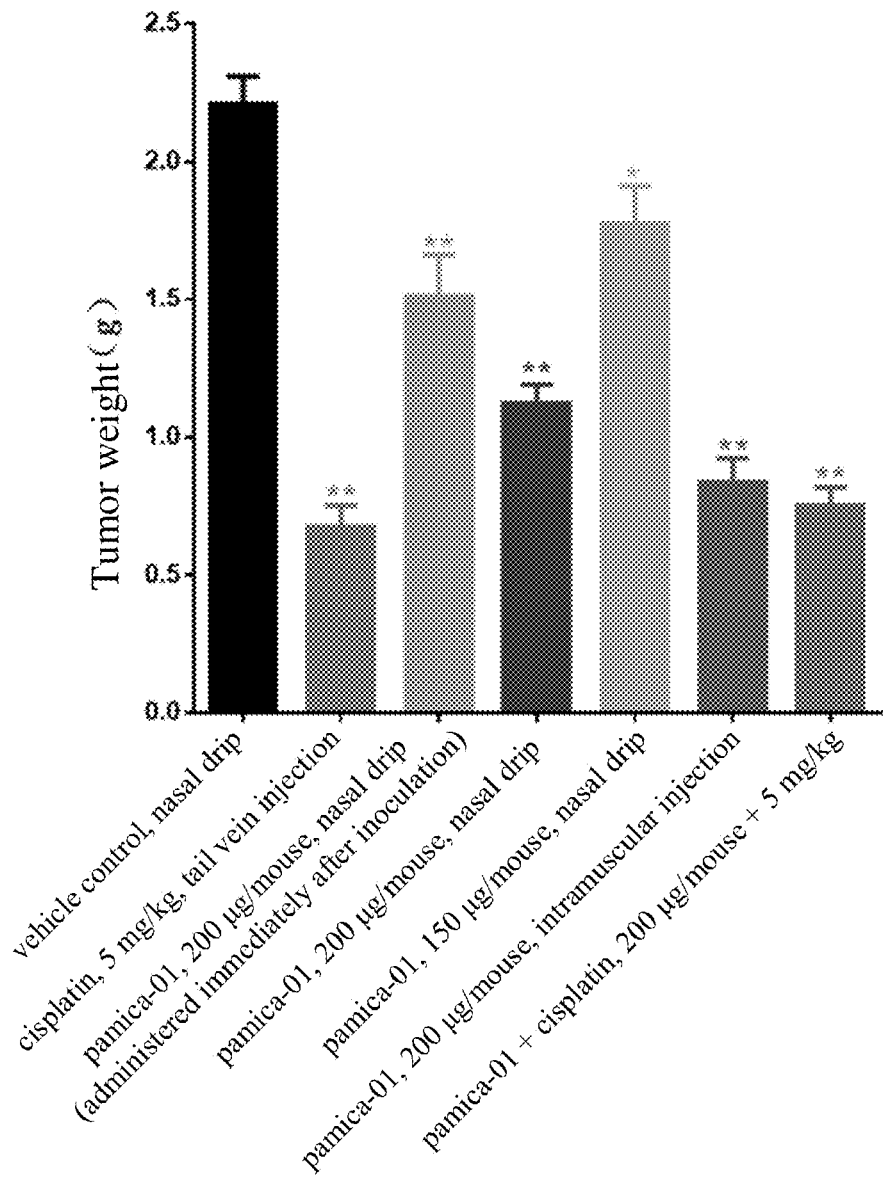
Figure 20:
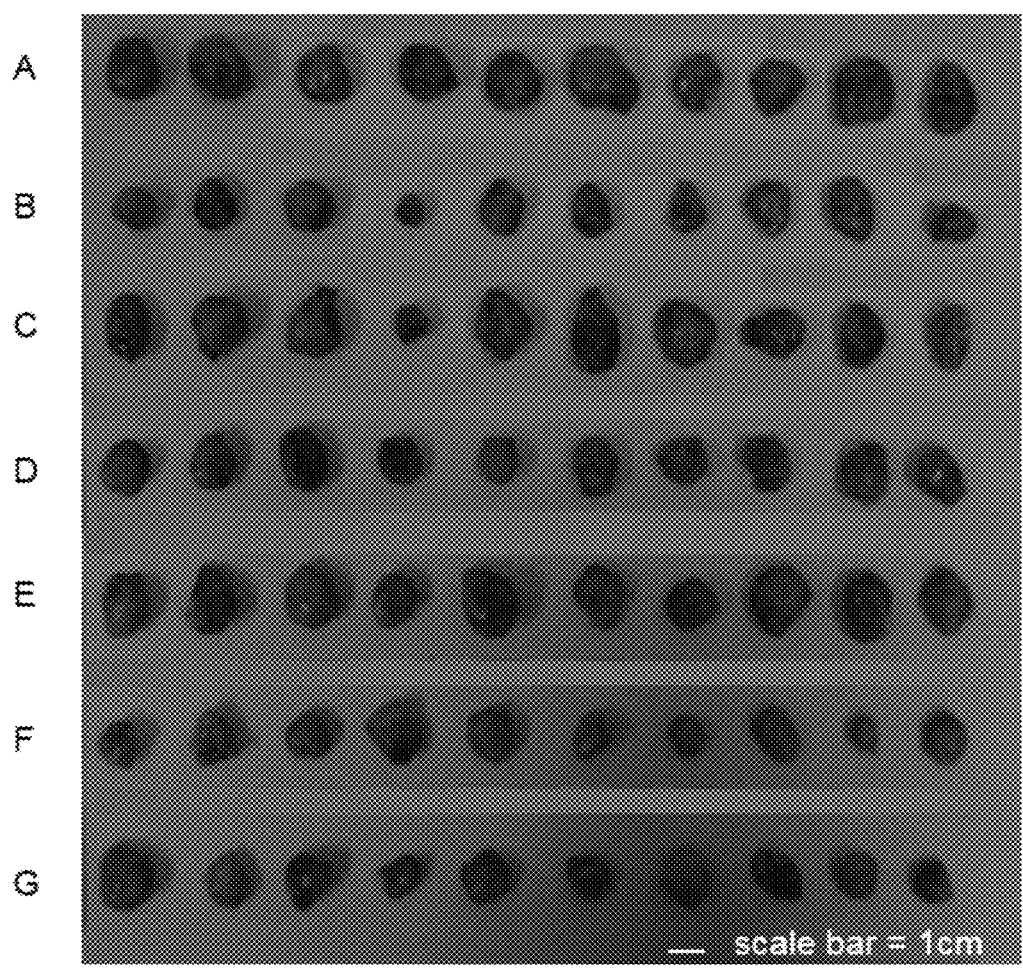
Figure 21:
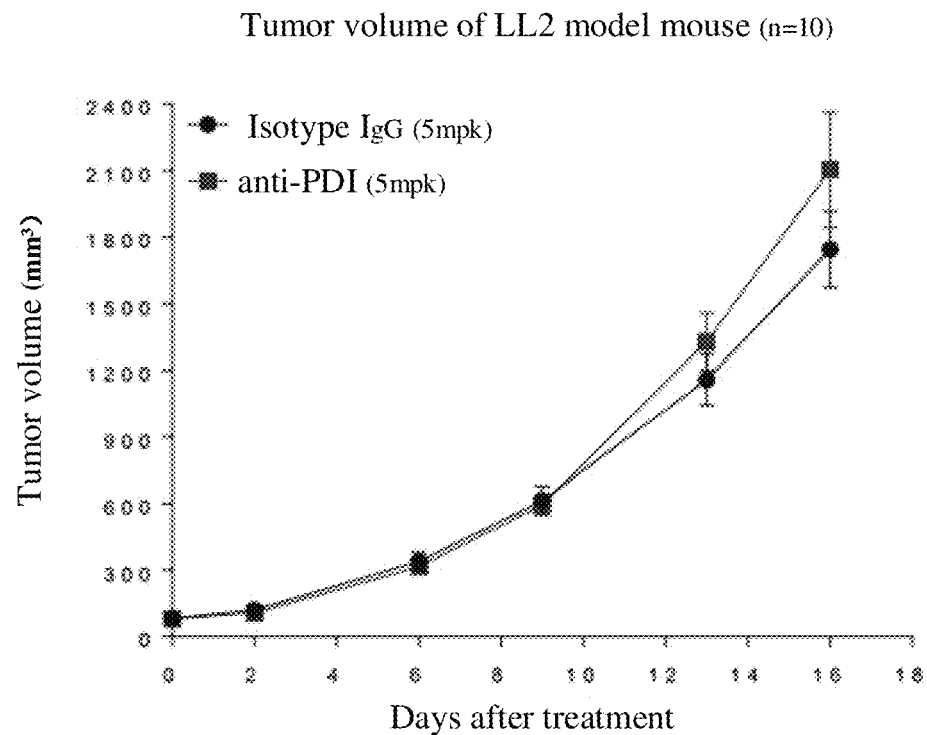

Results: in the PBS control group, the percentage of phagocytosis is 12% and the phagocytosis index was 0.11; and in the Pamica group, the percentage of phagocytosis is 66% and the phagocytosis index is 1.2, indicating that Pamica has a strong stimulation effect on the phagocytic function of macrophage. FIG. 16 shows that red blood cells are phagocytized by macrophages and FIG. 17 shows that red blood cells are not phagocytized by blue macrophages (by arrows).

Experimental Example 10 the Protection Test of Pamica Nasal Drop Mucosal Immune Formulation Alone Against Influenza in Mice Influenza virus: influenza virus subtype A mice-lung adaptive strain FM1, purchased from the Institute of Viral Disease Prevention and Control, Chinese Academy of Preventive Medicine.

Ribavirin: positive control drug, purchased from Shenyang Yanfeng Pharmaceutical Factory.

Mice: Kunming species, the mice of 8 g~10 g were used for FM1 virus passage, and the mice of 14 g~20 g were used for the following formal experiments.

The fatal pneumonia may be caused by nasal dripping with a suspension of influenza virus mice-lung adaptive strain FM1 at 5 $LD_{50}$/mouse. In the test, the mice were infected first and then administered. The test was performed in groups according to the following table.

| Groups | Dosage | Death rate % | $X^2$ | P value |
|---|---|---|---|---|
| influenza virus mice-lung adaptive strain FM1 | saline | 89 | | |
| Ribavirin positive control | 0.07 g/kg/d | 63 | 1.64 | >0.05 |
| nasal drops alone of the present disclosure | 0.1 ml/mouse | 43 | 3.88 | <0.05 |

The experimental results show that in the protection test in mice, the nasal drops of the present disclosure through the mucosal immune route has a better non-specific anti-influenza effect than ribavirin which is a recognized antiviral drug, and a significant anti-influenza effect shown by statistical analysis.

Experimental Example 11 the Effects of Pamica Mucosal Immune Formulation (Nasal Drops) Combined with Influenza Vaccine Through Nasal Mucosal Immunization and Subcutaneous Injection Immunization on Humoral Antibody IgA and on Influenza Virus Reproduction Titer, Compared to the Complete Freund's Adjuvant The experimental scheme is as follows:

Influenza virus: influenza virus mice-lung adaptive strain FM1 purchased from the Institute of Viral Disease Prevention and Control, Chinese Academy of Preventive Medicine.

Influenza vaccine: influenza virus split vaccine purchased from Hualan Biological Products Co., Ltd.

Complete Freund's adjuvant: Shanghai Via-geneprobio Technologies Co. Ltd.

Mucosal immune adjuvant of the present disclosure: from Xinfu (Beijing) Medical Technology Co., Ltd.

Mouse: Kunming species, the mice of 8 g~10 g were used for FM1 virus passage, and the mice of 14 g~20 g were used for the following formal experiments.

Complete Freund's adjuvant influenza vaccine: in a centrifuge tube, vaccine and complete Freund's adjuvant at the same volume were added homogeneously mixed in a vortex to form a water-in-oil emulsion.

Nasal drops combined with influenza vaccine of the present disclosure: the influenza vaccine and the mucosal immune adjuvant of the present disclosure were mixed in equal amounts to form an aqueous solvent.

Influenza vaccine: The influenza vaccine was mixed with PBS in equal amounts to form an aqueous solvent.
Immunization Method:

Subcutaneous injection immunization: mice were injected subcutaneously at 0 day and the $28^{th}$ days with 0.1 ml/mouse on the $42^{th}$ day, blood were drawn from some mice and the serum was separated, for antibody titer test. Other mice were infected by the suspension of influenza virus mice-lung adaptive strain FM1 at 5 $LD_{50}$/nasal drip. On the 5*day after infection, the virus titer of lung tissue was detected.

Nasal immunization: mice were immunized at 0.1 ml/mouse by nasal drip at 0 day and the $28^{th}$ days. On the $42^{th}$ day, blood was drawn from some mice to and the serum was separated for antibody titer test. Other mice were infected by the suspension of influenza virus mice-lung adaptive strain FM1 at 5 $LD_{50}$/nasal drip. On the $5^{th}$ day after infection, the virus titer of lung tissue was detected.

The experimental results of each group are shown in the following table:

Anti-influenza test of mucosal immune formulation combined with influenza vaccine by nasal drip

| Groups | Antibody index | Influenza virus titer after treatment |
|---|---|---|
| Subcutaneous injection immunization: | | |
| Influenza vaccine | $10^{3.1}$ | $10^4$ |
| Complete Freund's adjuvant influenza vaccine | $10^{5.5}$ | $10^{3.5}$ |
| Nasal drops of the present disclosure combined with influenza vaccine | $10^{4.5}$ | $10^{2.0}$ |
| Nasal mucosal immunization: | | |
| Influenza vaccine | $10^{2.5}$ | $10^{4.5}$ |
| Nasal drops of the present disclosure combined with influenza vaccine | $10^4$ | <10 |
| FM1 virus control | $10^{5.0}$ | |

The complete Freund's adjuvant is the gold standard for testing of promoting the body's cellular immunity. The test results show that the subcutaneous immunization of the mucosal immune formulation of the present disclosure combined with influenza vaccine produces antibodies 10 times lower than the complete Freund's adjuvant influenza vaccine does, but reduce the titer of influenza virus by 31.6 times than complete Freund's adjuvant influenza vaccine does; in particular, the nasal mucosal immunization in mouse shows that the nasal drop of the mucosal immune formulation of the present disclosure combined with the antigen produces antibodies 31.6 times higher than the simple influenza vaccine does, and reduces the titer of influenza virus by more than 3100 times, which has extremely significant effects.

Experimental Example 12 Pamica has a Clear Effect on the Preliminary Test of CIK Cell Effect-Target Experiment In the test carried out by Beijing Jingmeng Hi-Tech Stem Cell Technology Co., Ltd., the present disclosure has a clear effect in the preliminary test of the CIK cell effect-target experiment.

Sample number JSCIK2016042614; test date: Apr. 26, 2016; report date: Apr. 28, 2016.

Operation process: culturing and analysis were carried out according to the conventional CIK cell effect-target experiment, the experimental method is as shown in, for example, (The Immunotherapeutic Antitumor Effect of Dendritic Cells Co-cultured with Cytokine Induced Killer Cells, Jie Zhuang et al., Chinese Journal of Cell Biology, 2007, 29; 237-240).

Target cell: A549 Effector cell: cultured JSCIK2016042614

Conclusion: the killing ability of JSCIK2016042614 cells was comprehensively analyzed in combination with fluorescence microscope and detection by microplate reader as well as the error from the experiment itself and is medium at 1:10 (when the target-effect ratio was 1:10, the killing rate on the target cell A549 was 51.4%).

Experimental Example 13 the Anti-Cancer Effect of Pamica Mucosal Immune Preparation on the LL2 Lung Cancer Model of a Tumor-Bearing Mouse The anti-tumor effect of Pamica was tested by nasal spraying LL2 mouse transplanted tumor model. The tumor cells in this model grew rapidly, with tumor volume of $2201.9 \text{ mm}^3 \pm 68.01 \text{ mm}^3$ on the $14^{th}$ day after the inoculation and the experiment was over. Cisplatin as the positive control had the best effect on tumor shrinkage, followed by the Pamica intramuscular injection group. However, for Pamica nasal spray, except for the group administered at 0.1 mg/mouse, each nasal spray group administered at 0.2 mg/mouse has P<0.0001 compared with the vehicle-negative control group, showing a significant difference. Especially, in the same mouse model recorded in historical data, mouse type PD1 shows almost invalid. As explanation, the cisplatin group is more likely to show efficacy in this model with very rapid cell division. In general, Pamica has a remarkable effect in such a tumor-bearing mouse model under the new anti-cancer mechanism. In addition, no side effects were found in this mouse model.

The experiment groups are shown in the following table:

| Treatment | TV at day 14 | T/Cb (%) | pvalue |
|---|---|---|---|
| Vehicle | 2201.09 ± 68.01 | — | — |
| cisplatin (5 mg/kg) | 637.79 ± 62.87 | 28.9 | <0.0001 |
| Pamica-1 (200 µg, immediately administrated, nasal drip) | 1331.51 ± 139.21 | 60.4 | <0.0001 |
| Pamica-1 (200 µg, nasal drip) | 1163.83 ± 52.88 | 52.8 | <0.0001 |
| Pamica-1 (150 µg, nasal drip) | 1839.36 ± 83.57 | 83.5 | 0.0667 |
| Pamica-1 (200 µg, intramuscular injected) | 929.69 ± 109.95 | 41.7 | <0.0001 |
| Pamica-1 + cisplatin(200 µg + 5 mg/kg, nasal drip + I.V) | 799.63 ± 82.86 | 36.3 | <0.0001 |

The specific experimental results are shown in FIGS. 18~21.

In this experiment, the cells had a high tumor formation rate, and the tumor in the vehicle control group grew rapidly, with a tumor volume of $2201.09 \text{ mm}^3 \pm 68.01 \text{ mm}^3$ at the end of the experiment. In the positive control group, cisplatin showed obvious tumor inhibiting effect, indicating that this experiment is successful and the results were credible.

The test results show that in this study for the mouse transplanted tumor model of mouse lung cancer LL2 cell C57BL/6, groups except for the Pamica group administered at 150 µg/mouse show significant effect of inhibiting of tumor growth, regardless of nasal drip or intramuscular administration, and the statistical determination shows that there are extremely significant difference with P<0.0001; at the same time, no obvious toxic and side effects show in tumor-bearing mice.

Previous data from Huiyuan Biotech showed that the murine PD-1 antibody is relatively less effective in the LL2 model (tumor inhibition rate is less than 10%). Pamica, which also acts on the immune system, presents better effect than that of PD-1 antibody. Generally, it is believed that the anti-tumor efficacy of PD-1 antibody depends on the expression level of PD-L1 in tumor cells, or is related to mutation load, microsatellite instability-high (MSI-H) or defects in mismatch repair (dMMR), which in turn affects the drug effect thereof. As an immune adjuvant, Pamica has tumor inhibiting effect in a wider range than that of immune checkpoints, showing great development prospect.

Experimental Example 14 In Vivo Anti-Tumor Effect Study of Pamica in 4T1-Luc Mouse Model of In-Situ Breast Cancer This pharmacodynamic experiment was carried out for 9 groups: vehicle group, PD1 group, 6 Pamica treatment groups, and Pamica combined with PD1 administration group. The vehicle group was nasal drip administrated with PBS solution at 66.7 µL/mouse on the $16^{th}$ day after inoculation, once every two days; PD1 group was intraperitoneally injected with PD1 solution at 100 µg/mouse on the $16^{th}$ day after inoculation, once a week; 6 Pamica treatment groups were administrated as follows respectively: one group was nasal drip administrated with Pamica at 200 µg/mouse 7 days before inoculation, once every two days; one group was nasal drip administrated with Pamica at 200 µg/mouse on the day of inoculation, once every two days; one group was nasal drip administrated with Pamica at 200 µg/mouse on the $16^{th}$ day after inoculation, once every two days; one group was nasal drip administrated with Pamica at 300 µg/mouse on the $16^{th}$ day after inoculation, once every two days; one group was intramuscularly administrated with Pamica at 200 µg/mouse on the $16^{th}$ day after inoculation, once every two days; and one group was intramuscularly administrated with Pamica at 300 µg/mouse on the $16^{th}$ day after inoculation, once every two days; the Pamica combined with PD1 administration group was nasal drip administrated with Pamica at 200 µg/mouse on the $16^{th}$ day after inoculation, once every two days+intraperitoneally injected with Pamica at 100 µg/mouse on the $16^{th}$ day after inoculation, once a week. Female Balb/c mice were used in the experiment, measured for the tumor volume every three days, and weighed for the body weight every two days. The experiment was ended when the average tumor volume of the vehicle control group exceeded 2000 mm³, and the bioluminescence of the tumor was measured by the small animal in vivo imager. Finally, the organs of mice in each group were taken for HE staining.

The results of the pharmacodynamics test showed that the 7-day advanced group and the 0-day group had relatively weak abilities of inhibiting the growth and metastasis of tumor, and the two Pamica intramuscular injection groups had a stronger inhibiting effect on the growth and metastasis of tumor than that of the two Pamica nasal drip groups. Except for the 200 µg/mouse Pamica nasal drip group, the 300 µg/mouse Pamica nasal drip group, the 200 µg/mouse Pamica intramuscular injection group and the 300 µg/mouse Pamica intramuscular injection group all can significantly inhibit the growth and metastasis of tumor. At the end of the experiment, the tumor inhibition rates of the 200 µg/mouse Pamica nasal drip group and the 300 µg/mouse Pamica nasal drip group were 25% and 35%, respectively. The tumor inhibition rates of the 200 µg/mouse Pamica intramuscular injection group and the 300 µg/mouse Pamica intramuscular injection group were 56% and 61%, respectively.

The above results indicate that Pamica has a good effect on inhibiting the growth and metastasis of tumor in 4T1 breast cancer.

The experimental process and experimental results are described in detail below.

1. Experimental Method
1.1 Construction of 4T1-Luc Mouse Model of In-Situ Breast Cancer The female Balb/c mice were taken, 4T1-luc breast cancer cells in the logarithmic growth phase were selected, and inoculated under the fourth mammary gland of Balb/c mice at an amount of $1\times10^5$ cells/0.2 mL/mouse to construct in situ tumor-bearing mouse model. The volume of tumor mass was dynamically measured with vernier caliper. The tumor volume is calculated according to the following formula: $V=0.5\times L\times D2$ (wherein V is the tumor volume, L is the long diameter of the tumor, and D is the short diameter of the tumor).

1.2 Setting of Administration Time

For the Pamica nasal drip administrated 7 days before inoculation group (referred to as the 7-day advanced group), 10 mice were randomly selected 7 days before tumor inoculation, and were administered according to Table 1;

For the Pamica nasal drip administrated 0 day of inoculation group (referred to as the 0-day group), 10 mice were randomly selected on the day of tumor inoculation, and were administered according to Table 1;

For the vehicle group, when the tumor volume grew to about 80 mm$^3$, that is, on the 16$^{th}$ day after tumor inoculation, the administration began according to Table 1.

For the PD1 group, when the tumor volume grew to about 80 mm$^3$, that is, on the 16$^{th}$ day after tumor inoculation, the administration began according to Table 1.

For the 200 μg/mouse Pamica nasal drip group, when the tumor volume grew to about 80 mm$^3$, that is, on the 16th day after tumor inoculation, the administration began according to Table 1.

For the 300 μg/mouse Pamica nasal drip group, when the tumor volume grew to about 80 mm$^3$, that is, on the 16$^{th}$ day after tumor inoculation, the administration began according to Table 1.

For the 200 μg/mouse Pamica intramuscular injection group, when the tumor volume grew to about 80 mm$^3$, that is, on the 16$^{th}$ day after tumor inoculation, the administration began according to Table 1.

For the 300 μg/mouse Pamica intramuscular injection group, when the tumor volume grew to about 80 mm$^3$ that is, on the 16$^{th}$ day after tumor inoculation, the administration began according to Table 1.

TABLE 1

Experimental dosage and groups

| | Test sample | Animal | Route of administration | Dosage | Interval of administration |
|---|---|---|---|---|---|
| 1 | vehicle | 16 | nasal drip | 66.7 μL | once every two days |
| 2 | PD1 | 16 | intraperitoneal | 100 μg/mouse | once a week |
| 3 | Pamica | 16 | nasal drip (administered on the 16$^{th}$ day after inoculation) | 200 μg/mouse | once every two days |
| 4 | Pamica | 16 | nasal drip (administered on the 16$^{th}$ day after inoculation) | 300 μg/mouse | once every two days |
| 5 | Pamica | 16 | intramuscular injection (administered on the 16$^{th}$ day after inoculation) | 200 μg/mouse | once every two days |
| 6 | Pamica | 16 | intramuscular injection (administered on the 16$^{th}$ day after inoculation) | 300 μg/mouse | once every two days |
| 7 | Pamica | 10 | nasal drip (administered 7 days before inoculation) | 200 μg/mouse | once every two days |
| 8 | Pamica | 10 | nasal drip (administered 0 day after inoculation) | 200 μg/mouse | once every two days |
| 9 | Pamica + PD1 | 10 | nasal drip + intraperitoneal | 200 μg/mouse + 100 μg/mouse | once every two days + once a week |

1.3 Experimental End

The entire experiment ended on the 30$^{th}$ day after the administration because the rumor volume exceeded 2000 mm$^3$.

1.4 Index Observation

The rumor volume was measured for volume every three days, and the mice were weighed every two days. At the end of the experiment, the heart, liver, spleen, lung, kidney, and rumor were separated. The heart, liver, spleen, and kidney were fixed with 4% neutral formaldehyde, then paraffin sectioned and analyzed by HE staining, the tumor was photographed and weighed; the lung was fixed with Bouin's fixative for 16 hours, immersed in 50% alcohol for 2 hours, photographed, fixed with 4% neutral formaldehyde, paraffin-sectioned and analyzed by HE staining.

1.5 Small Animal In Vivo Imager

At the end of the administration, the mice were intraperitoneally administrated with 100 μL of Luciferin at a concentration of 30 mg/mL as the fluorescein substrate, and anesthetized with isoflurane. After 17 minutes, the mice were fixed in a small animal in vivo imager to observe the bioluminescence. The image acquisition parameters are as follows: acquisition time: 0.2 seconds; Bin value: 4; and F value: 2. Image processing software: Living Image® software (version 4.3.1; Caliper Life Sciences Inc.).

2. Statistical Analysis

The experimental data are all expressed as "mean t standard deviation", and the SPSS Statistics 19 (version 4.0.100.1124; SPSS Inc., IBM Company, USA) software was used for data analysis. One-factor analysis of variance ANOVA was used for data comparison, and the t-test was used for significant differences between groups: * $p<0.05$;  $p<0.01$; * $p<0.001$.

3. Experimental Results and Discussion 3.1 Tumor volume

Figure 22:
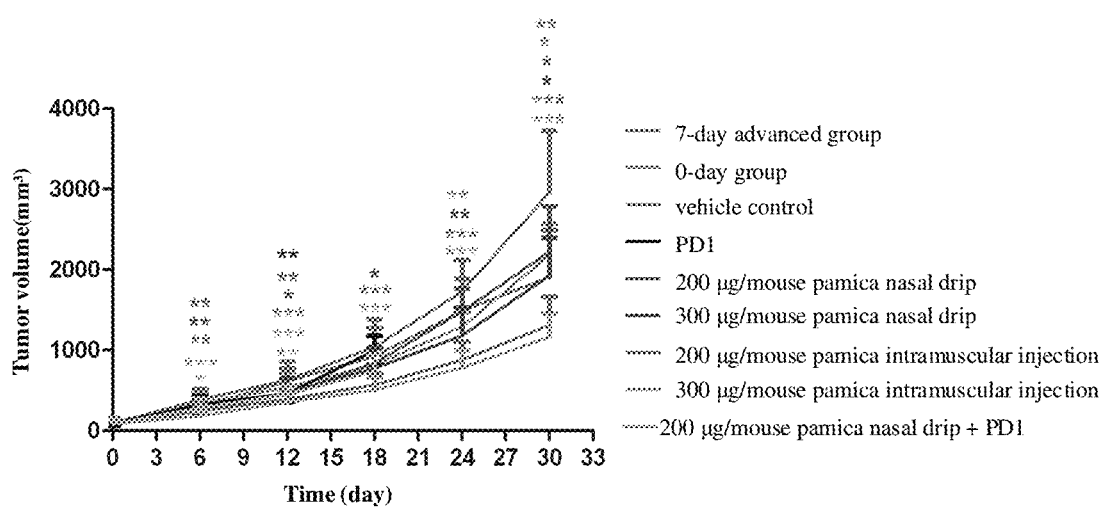
FIGS. 22~35 show in vivo anti-tumor effects of Pamica in 4T1-luc mouse model of in-situ breast cancer according to an embodiment of the present disclosure.

The curves of tumor volume changes are shown in FIG. 22.

TABLE 2 t-test results of tumor volume

| | 6 days | 12 days | 18 days | 24 days | 30 days |
|---|---|---|---|---|---|
| 7-day advanced group | | | | | ** |
| 0-day group | | | | ** | * |
| PD1 | | ** | | — | — |
| 200 μg/mouse Pamica nasal drip | ** | ** | | | * |
| 300 μg/mouse Pamica nasal drip | ** | * | | ** | * |
| 200 μg/mouse Pamica intramuscular injection | ** | *** | * | *** | *** |
| 300 μg/mouse Pamica intramuscular injection | *** | *** | *** | *** | *** |
| 200 μg/mouse Pamica nasal drip + PD1 | * | ** | *** | — | — |

Note:
Error bar indicates SD;
— indicates no data
*: indicates p < 0.05 compared with the vehicle group;
**: indicates p < 0.01 compared with the vehicle group;
***: indicates p < 0.001 compared with the vehicle group.

It can be seen from FIG. 22 and Table 2 that, the tumor inhibiting effects of the 7-day advanced group and the 0-day group are relatively weak, and the two intramuscular injection groups have better tumor inhibiting effects than the two nasal drip groups. The specific results are as follows.

The Pamica 7-day advanced group and 0-day group have certain tumor inhibiting effects in the later stage, and basically no tumor inhibiting effect in the early stage, indicating that the advanced administration or immediate administration has no obvious tumor killing effect, and laterally proving that Pamica is a tumor treatment vaccine, not a preventive vaccine. At the end of the experiment, the tumor inhibition rates of the 7-day advanced group and 0-day group were 36% and 26%, respectively.

The tumor volumes of the PD1 group on the $12^{th}$ day were significantly different from that of the vehicle group (**p<0.01), indicating that PD1 has a certain inhibiting effect in 4T1 mouse breast cancer.

In each treatment group of the PD1 combined with Pamica administration groups, most of the mice had died on the $20^{th}$ day after the administration, so there was no data from the later measurement for the two groups. Among them, the tumor volumes of the combined administration groups on the $6^{th}$, $12^{th}$, and $18^{th}$ day were significantly different from that of the vehicle group (*p<0.05, p<0.01, *p<0.001, respectively).

The 200 μg/mouse Pamica nasal drip group had a significant inhibiting effect in the early stage of administration, and a gradually weakened tumor inhibiting effect in the later stage of administration. The tumor volumes on the $6^{th}$ and $12^{th}$ day were significantly different from that of the vehicle group (**p<0.01). Except for the $18^{th}$ day, the tumor volumes of the 300 μg/mouse Pamica nasal drip group were significantly different from that of the vehicle group at other times. It shows that nasal drip administration is effective and the tumor inhibiting effect is dosage-dependent. At the end of the experiment, the tumor inhibition rates of the 200 μg/mouse Pamica nasal drip group and the 300 μg/mouse Pamica nasal drip group were 25% and 35%, respectively.

The tumor inhibiting effects of the two Pamica intramuscular injection dosage groups were similar during the whole administration process, and were significantly different from that of the vehicle group, and the tumor inhibiting effect of the two intramuscular injection groups were better than that of the two nasal drip groups. At the end of the experiment, the tumor inhibition rates of the 200 μg/mouse Pamica intramuscular injection group and the 300 μg/mouse Pamica intramuscular injection group were 56% and 61%, respectively.

3.2 Body Weight

Figure 23:
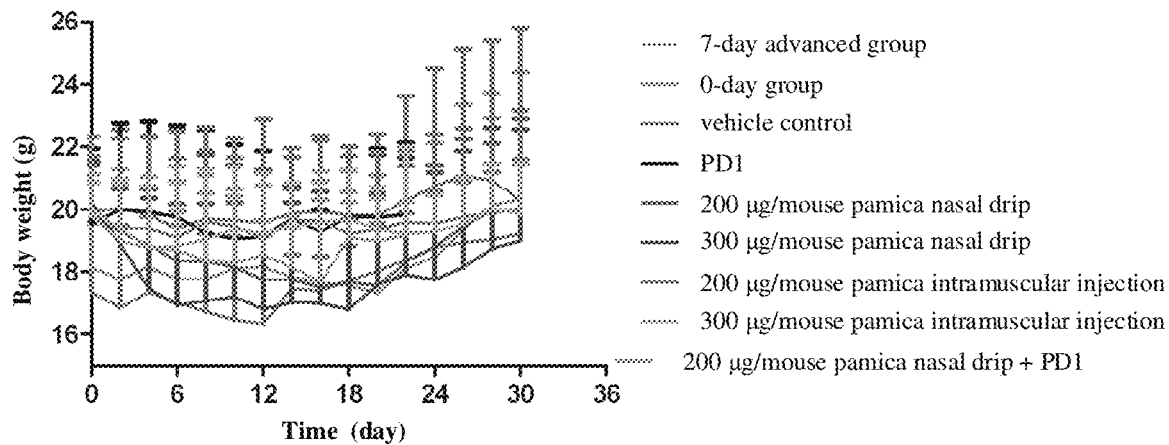

The curves of the body weight changes of mice are shown in FIG. 23.

TABLE 3

Statistical t-test results of body weight of mice in each group and vehicle group

| | 0 day | 2 days | 4 days | 6 days | 8 days | 10 days | 12 days | 14 days |
|---|---|---|---|---|---|---|---|---|
| 7-day advanced group | ** | ** | ** | ** | *** | ** | ** | *** |
| 0-day group | *** | *** | ** | ** | ** | ** | ** | *** |
| PD1 | | | | | | | | |
| 200 μg/mouse Pamica nasal drip | | * | * | ** | ** | *** | *** | *** |
| 300 μg/mouse Pamica nasal drip | | ** | *** | *** | ** | *** | *** | *** |
| 200 μg/mouse Pamica intramuscular injection | | | | | | | | |
| 300 μg/mouse Pamica intramuscular injection | | ** | * | | | | | |
| 200 μg/mouse Pamica nasal drip + PD1 | | | * | | ** | ** | ** | *** |

| | 16 days | 18 days | 20 days | 22 days | 24 days | 26 days | 28 days | 30 days |
|---|---|---|---|---|---|---|---|---|
| 7-day advanced group | *** | *** | * | * | * | * | | |
| 0-day group | *** | ** | ** | ** | * | | | |
| PD1 | — | — | — | — | — | — | — | — |
| 200 μg/mouse Pamica nasal drip | *** | *** | *** | ** | * | * | | |
| 300 μg/mouse Pamica nasal drip | *** | ** | ** | ** | ** | ** | * | |
| 200 μg/mouse Pamica intramuscular injection | | | | | | | | |

TABLE 3-continued

Statistical t-test results of body weight of mice in each group and vehicle group

| | | | | | |
|---|---|---|---|---|---|
| 300 μg/mouse Pamica intramuscular injection | * | * | * | | |
| 200 μg/mouse Pamica nasal drip + PD1 | — | — | — | — | — |

Note:
Error bar indicates SD;
— indicates no data
* indicates p < 0.05 compared with the vehicle group;
** indicates p < 0.01 compared with the vehicle group;
*** indicates p < 0.001 compared with the vehicle group.

It can be seen from FIG. 23 and Table 3 that the body weights of the mice in the PD1 and combined administration groups were not significantly different from that of the vehicle group during the effective measurement time, indicating that the side effects thereof are less. Except in the later stage of administration, the body weights of the 7-day advanced group, 0-day group, 200 μg/mouse Pamica nasal drip group, and 300 μg/mouse Pamica nasal drip group were significantly lower than that of the vehicle group at other times. There was no significant difference between the 200 μg/mouse Pamica intramuscular injection group and the vehicle group during the entire administration period. The body weight of the 300 μg/mouse Pamica intramuscular injection group was lower than that of the vehicle group in the mid-stage of administration, and was not significantly different from the vehicle group in the early stage and later stage of administration.

The above results indicate that intramuscular injection has little effect on the body weight of mice and has less side effect, and intranasal administration has certain side effect in mice.

3.3 Tumor Weight, Spleen Weight and Tumor Photos

Figure 24:
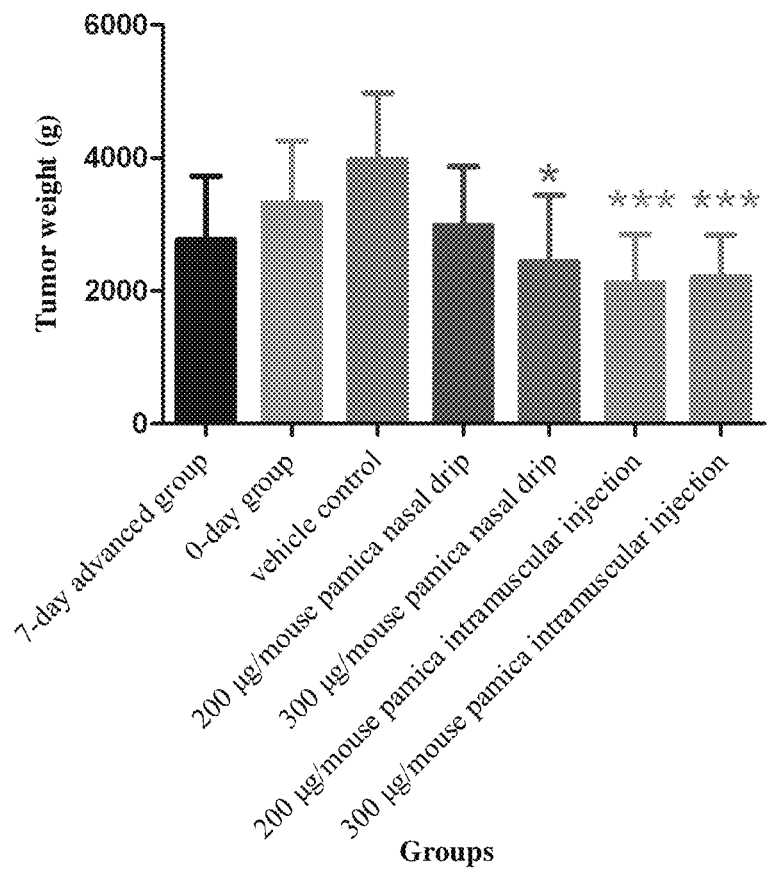
Figure 25:
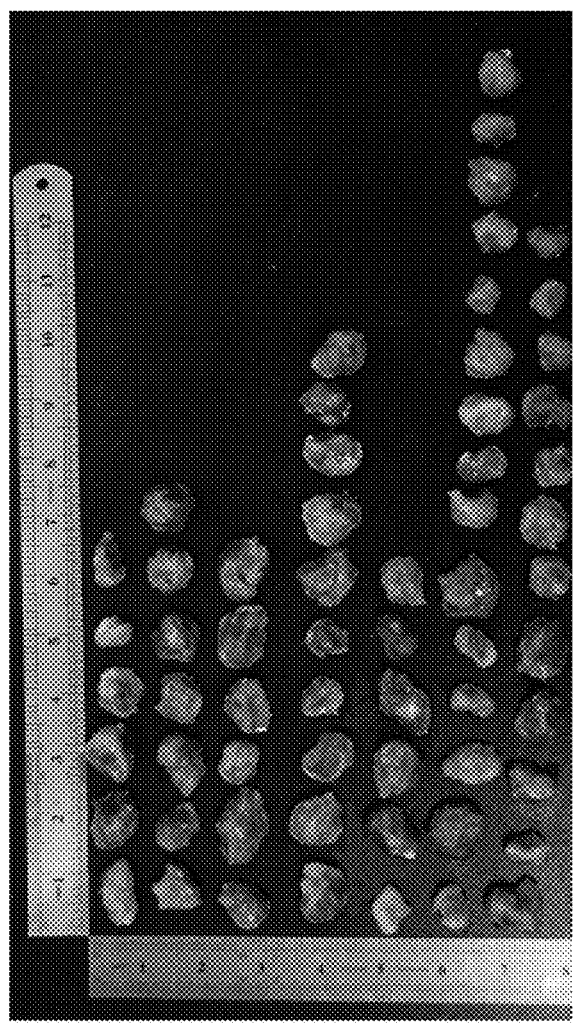

It can be seen from FIG. 24 and FIG. 25 that there was no significant difference in tumor weight between the 7-day advanced group or the 0-day group compared and the control group, and the two Pamica intramuscular injection groups had a stronger inhibiting effect on the growth of tumor than the two Pamica nasal drip groups. Except for the 200 μg/mouse Pamica nasal drip group, the 300 pig/mouse Pamica nasal drip group, the 200 μg/mouse Pamica intramuscular injection group and the 300 pig/mouse Pamica intramuscular injection group can all be significantly inhibit the growth of tumor, with statistical difference compared with the vehicle group (*p<0.05. p<0.01. *p<0.001, respectively).

Figure 26:
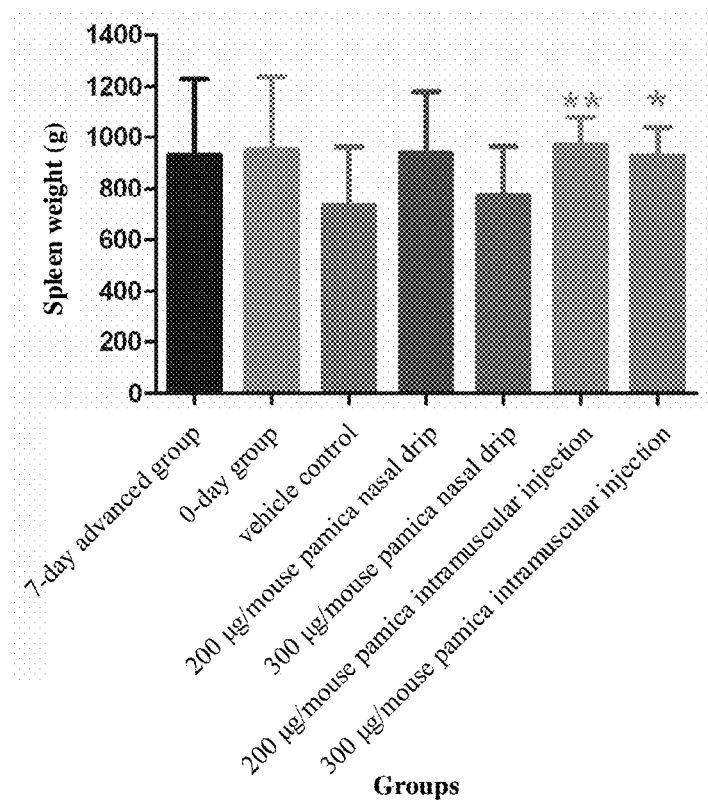

Spleen is the largest immune organ of the body, accounts for 25% of the total lymphatic tissue of the body, contains a large number of lymphocytes and macrophages, and is the center of the cellular immunity and humoral immunity of body. It can be seen from FIG. 26 that the spleen weights of the 200 pig/mouse Pamica intramuscular injection group and 300 pig/mouse Pamica intramuscular injection group was significantly higher than that of the vehicle group, with statistical differences (**p<0.01, *p<0.05, respectively), indicating that the immune response of the intramuscular injection group may be stronger.

3.4 Lung Photos

Figure 27:
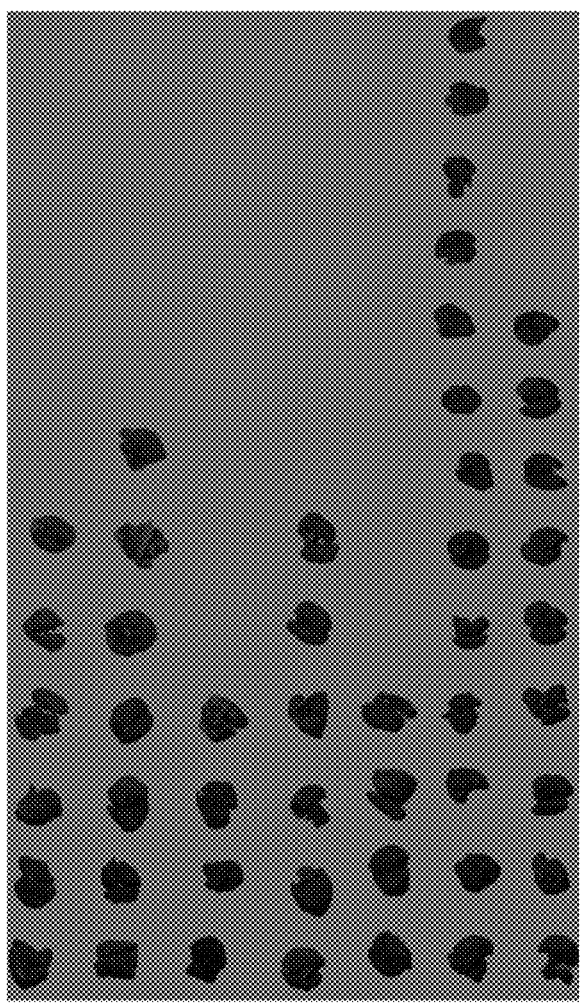
Figure 28:
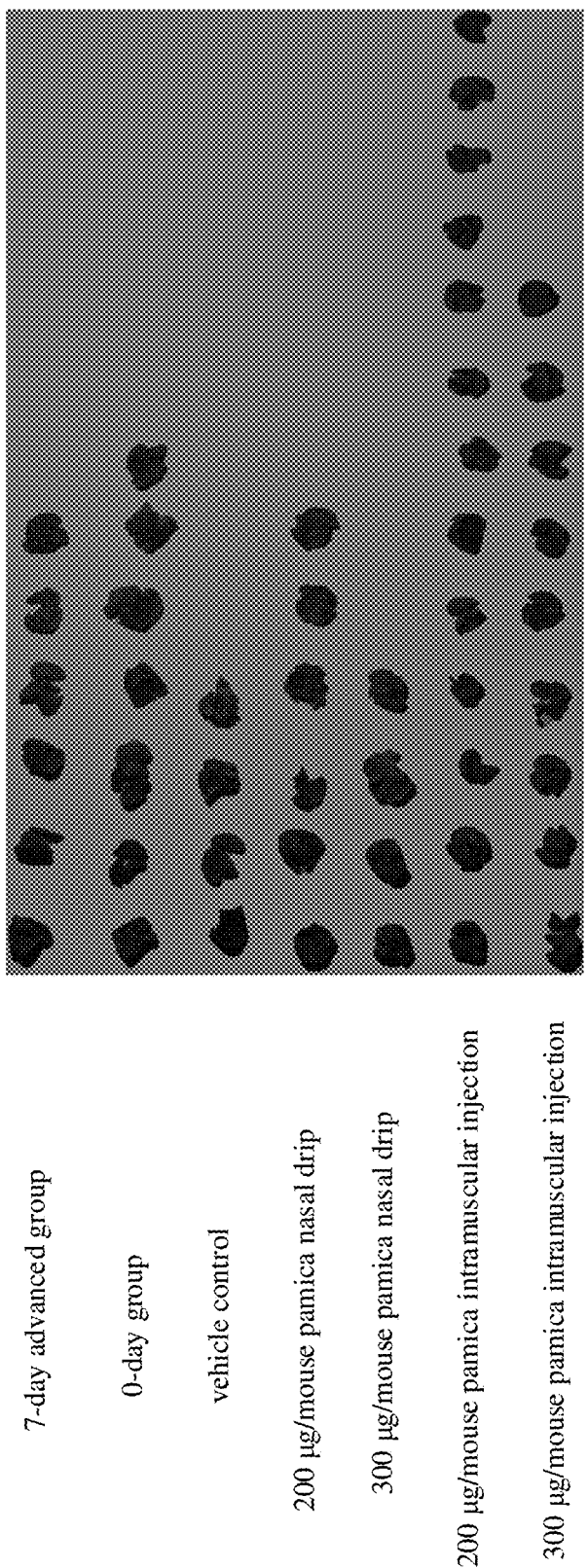
Figure 29:
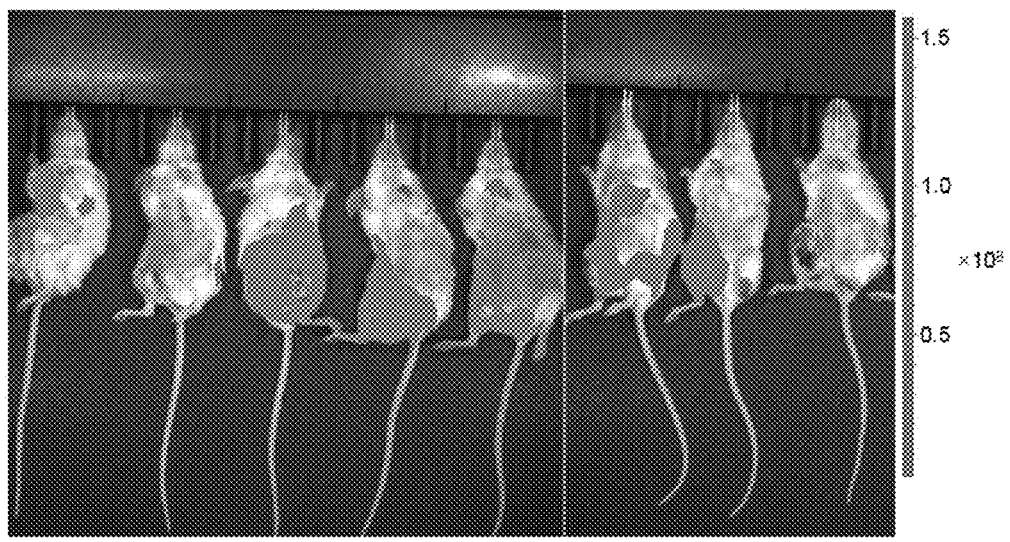
Figure 30:
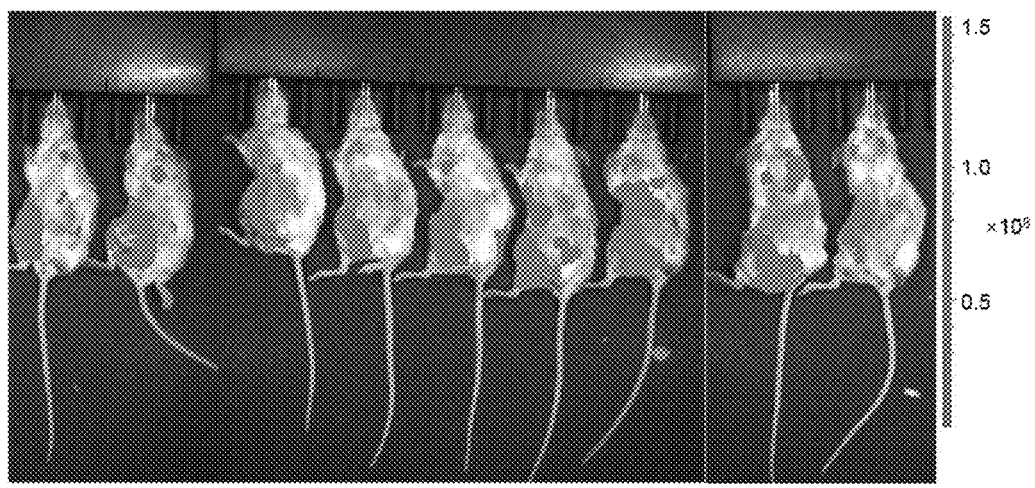
Figure 31:
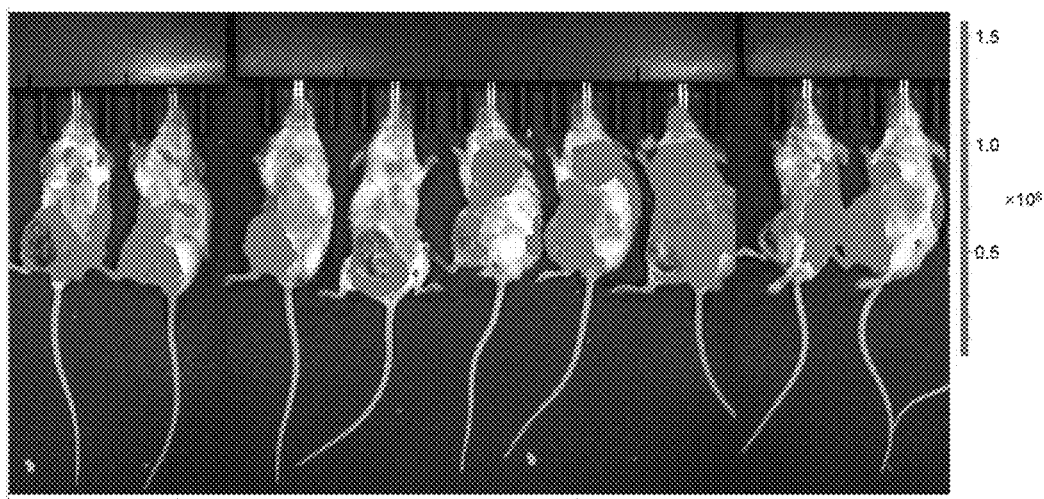
Figure 32:
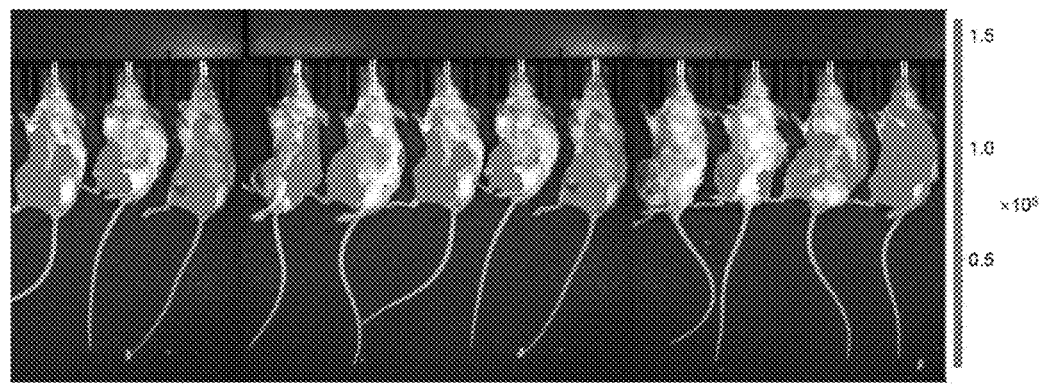
Figure 33:
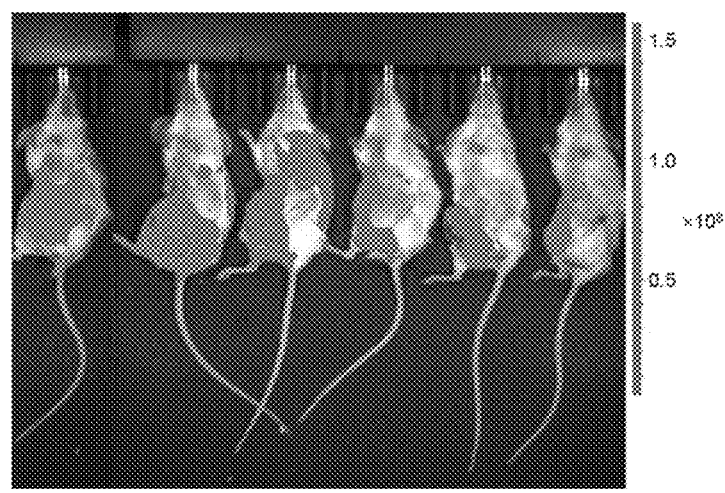
Figure 34:
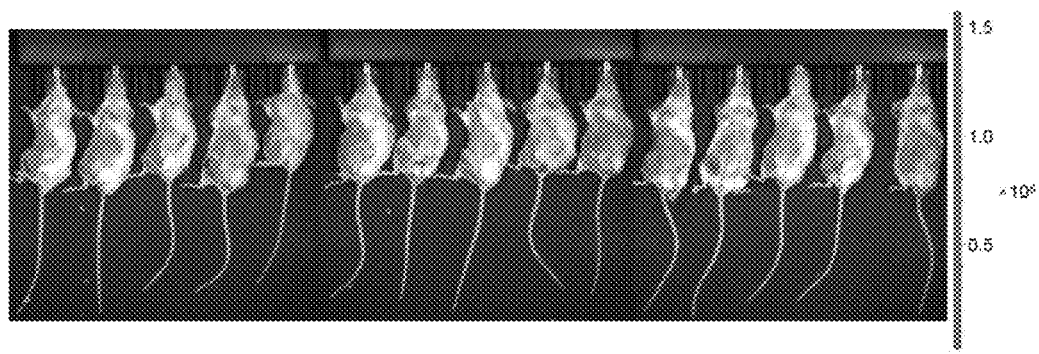
Figure 35:
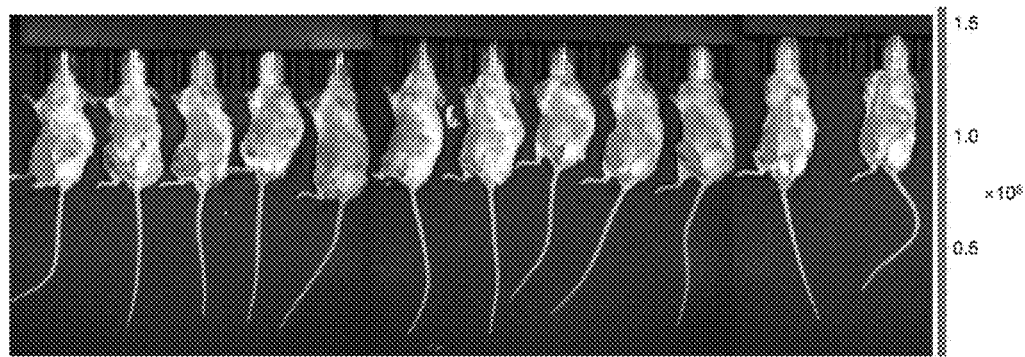

It can be seen from FIG. 27 and FIG. 28 that there are many white tumor nodules in the surface of lung tissue in the vehicle group, the 7-day advanced group, and the 0-day group, indicating that the 7-day advanced group and the 0-day group basically have no effect on inhibiting the lung metastasis of 4T1. There are fewer nodules in the surface of lung tissue of the 200 μg/mouse Pamica nasal drip group and 300 μg/mouse Pamica nasal drip group, the 200 μg/mouse Pamica intramuscular injection group and 300 μg/mouse Pamica intramuscular injection group have the least nodules in the surface of lung tissue, indicating that the two nasal drip groups and the two intramuscular injection groups can effectively inhibit the lung metastasis of 4T1, and the intramuscular injection group has a stronger ability of inhibiting the lung metastasis of 4T1 than that of the nasal drip group.

3.5 Small Animal Imager

It can be seen from FIG. 29-FIG. 35 that, the bioluminescence intensities of tumor sites and metastases of the vehicle group, 7-day advanced group, and 0-day group are stronger. The bioluminescence intensities of the tumor site and metastasis in the 200 μg/mouse Pamica nasal drip group and the 300 μg/mouse Pamica were weakened, and the bioluminescence intensities of tumor sites and metastasis in the 200 μg/mouse Pamica intramuscular injection group and 300 μg/mouse Pamica intramuscular injection group were the weakest, indicating that the intramuscular injection group has a stronger ability of inhibiting the growth and metastasis of 4T1 breast cancer than that of the nasal drip group, which is consistent with the above results.

4. Conclusion

In this experiment, we successfully established a 4T1-luc mouse model of in-situ breast cancer. The tumor grew rapidly, and the tumor volume exceeded 2000 mm$^3$ at the end of the experiment.

The test results show that in this study of the mouse breast cancer 4T1-luc cell Balb/c mouse orthotopic tumor model, except for that in the PD1 and the combined administration group, a large number of mice died due to PD1, thus only part of the experimental data was obtained, the other each group all had a certain tumor inhibiting effect in a certain period of time. The 7-day advanced group, 0-day group and 200 μg/mouse Pamica nasal drip group had no obvious tumor inhibiting effect, 200 μg/mouse Pamica nasal drip group, 200 μg/mouse Pamica intramuscular injection group and 300 μg/mouse Pamica intramuscular injection group all showed obvious tumor inhibiting effects.

Experimental Example 15 the Use of Pamica in the Treatment of Patients Infected with Human Papilloma Virus (HPV)

| Name (gender, age) | Before administration | Administration method | After administration | Administration time |
|---|---|---|---|---|
| Zhang X (female, 28 years old) | High-risk human papilloma virus infection (positive-HPV16 infection) | spray administrated once every other day, 2.4 mg each time | High-risk human papilloma virus HPV16 turns negative | 2017 Aug. 9 to 2018 Jan. 5 |
| XX Zhang (female, 30 years old) | High-risk human papilloma virus infection (positive-HPV18 infection) | spray administrated once every other day, 2.4 mg each time | High-risk human papilloma virus HPV18 turns negative | 2017 Nov. 4 to 2018 Jan. 25 |
| XX Qu (female, 34 years old) | High-risk human papilloma virus infection (positive-HPV18 infection) | spray administrated once every other day, 2.4 mg each time | High-risk human papilloma virus HPV18 turns negative | 2017 Oct. 23 to 2018 Jan. 13 |

Experimental Example 16 the Use of Pamica in the Treatment of Breast Cancer

1. Positive Control Drugs:
PD1, paclitaxel injection
2. Construction of an Orthotopic Breast Cancer Animal Model of 4T1-Bearing Mouse The female BALB/c mice were taken; 4T1-luc breast cancer cells in the logarithmic growth phase were selected, and inoculated at an amount of $1 \times 10^5$ cells/0.2 mL/mouse under the fourth mammary gland of BALB/c mice to construct an orthotopic tumor-bearing mouse model. The volume of tumor mass was dynamically measured with vernier caliper. The tumor volume is calculated according to the following formula: $V=0.5 \times L \times D2$ (where V is the tumor volume, L is the long diameter of the tumor, and D is the short diameter of the tumor).
3. Influence on the Growth and Spontaneous Metastasis of 4T1 Breast Cancer In Situ
3.1 Group setting and dosage regimen ① for the PBS group, a few days after tumor inoculation. PBS was administered by nasal drip, 100 μL/mouse, once every other day;

② for the PD1 group, a few days after tumor inoculation, PD1 was administered intraperitoneally, 100 μg/mouse, once a week;

③ for the paclitaxel group, a few days after tumor inoculation, paclitaxel was administered by tail vein injection, 10 mg/kg, once a week;

④ for the Pamica nasal drip group, a few days after tumor inoculation, Pamica was administered by nasal drip, 100 μL (0.3 mg)/mouse, once every other day, with 50 μL of nasal drip in the morning on the day of administration, and 50 μL of nasal drip in the afternoon;

⑤ for the Pamica intramuscular injection group, a few days after tumor inoculation. Pamica was injected intramuscularly, 100 μL (0.3 mg)/mouse, administered once every other day;

⑥ for the combined administration group, a few days after tumor inoculation, PD1 intraperitoneal (100 μg/mouse, administered once a week)+Pamica nasal drip (100 μL/mouse, administered once every other day);

⑦ for the combined administration group, a few days after tumor inoculation, paclitaxel tail vein injection (10 mg/kg, administered once a week)+Pamica nasal drip (100 μL/mouse, administered once every other day).

3.2 Number of animals in each group: 15 animals in each group (there are 5 redundant animals in each group).
3.3 Time to end the experiment: according to the actual situation (the mouse died, or the difference between the administration group and the control group is obvious), the experiment may end early.
3.4 Experimental protocol The in situ 4T1-luc breast cancer model was established, and the small animal in vivo imager was used for early detection and grouping. Administration was performed according to the group setting and dosage regimen under item 6.1. The tumor volume (measured once every 3 days), weight change (measured once every 3 days), tumor weight (detected in the end), spleen weight (detected in the end), TUNEL staining (detected in the end) were measured. The lung was fixed with Bouin's fixative and then photographed. Each tissue and organ was fixed with neutral formaldehyde, then stained with H&E (detected in the end), and the bioluminescence intensity of tumor in situ and metastasis at different time points and final time points was observed by a small animal in vivo imager. The effects of inhibiting the growth and metastasis of tumor in situ between each group were comprehensively compared.

Experiments have proved that Pamica has obvious effects in reducing the tumor volume of breast cancer, controlling tumor weight and spleen weight, and promoting tumor cell apoptosis, and other aspects.

Finally, it should be noted that the above embodiments are only intended for illustration, but not to limit the technical solutions of the present disclosure; although the present disclosure has been described in detail with reference to the foregoing examples, those of ordinary skill in the art should understand that it is still possible to make modifications to the technical solutions recited in the foregoing examples, or make equivalent replacements to some or all of the technical features; and these modifications or replacements do not make the essence of the corresponding technical solutions deviate from the scope of the technical solutions of the examples of the present disclosure.

Industrial Utility

The complex of the present disclosure has moderate viscosity and molecular weight, and is convenient to use in pharmaceutical application; it has stable chemical properties, and is hardly degraded in long-term storage and safe to use. The complex, if used alone, can significantly potentiate the non-specific immune response of the body and achieve the purpose of preventing and treating diseases, and if used in combination with other drugs, has better anti-tumor, anti-viral and anti-(super) bacteria efficacy and is easily absorbed by patients.

The invention claimed is:

1. A method for preparing a complex for potentiating an immune response, comprising:
   heating a polyinosinic-polycytidylic acid at 80° C.~99° C. for 70 min~120 min, and then
   contacting a polyinosinic-polycytidylic acid, at least a cationic stabilizer, and a soluble calcium salt in a liquid reaction system;
   the cationic stabilizer is a water-soluble non-antibiotic amino compound having a molecular weight of less than or equal to 5 kDa, or a graft formed by the water-soluble non-antibiotic amino compound and one or more of methoxypolyethylene glycol, polyethylene glycol, polyethylenimine, folic acid and galactose.

2. The method according to claim 1, wherein the water-soluble non-antibiotic amino compound is one or more selected from the group consisting of chitosan oligosaccharides, chitooligosaccharides, glucosamines, cationic liposomes, DEAE-dextran, polyacrylamide, polyamines, tetraaminofulvene, and polyethyleneimine.

3. The method according to claim 1, wherein the cationic stabilizer is selected from the group consisting of a chitosan oligosaccharide, a graft of chitosan oligosaccharide and methoxypolyethylene glycol, and a graft of chitosan oligosaccharide, methoxypolyethylene glycol and polyethyleneimine.

4. The method according to claim 1, wherein the graft has a molecular weight of less than or equal to 50 kDa.

5. The method according to claim 1, wherein in the liquid reaction system, the polyinosinic-polycytidylic acid has a concentration of 0.1 mg/ml~10 mg/ml;
   optionally, in the liquid reaction system, the concentration of the polyinosinic-polycytidylic acid is 0.5 mg/ml~5 mg/ml.

6. The method according to claim 1, wherein in the liquid reaction system, the cationic stabilizer has a concentration of 0.5 mg/ml~51.2 mg/ml;
   optionally, in the liquid reaction system, the concentration of the cationic stabilizer is 0.8 mg/ml~25.6 mg/ml.

7. The method according to claim 6, wherein in the liquid reaction system, the concentration of calcium ions in the soluble calcium salt is 0.1 mM~1 mM.

8. The method according to claim 3, wherein the chitosan oligosaccharide has a degree of deacetylation that is greater than or equal to 70%.

9. The method according to claim 1, wherein the soluble calcium salt is $CaCl_2$ and/or $CaNO_3$.

10. The method according to claim 1, comprising preparing polyinosinic-polycytidylic acid by reacting a solution of polycytidylic acid in PBS with a solution of polyinosinic acid in PBS at a temperature from 40° C.~50° C.

11. The method according to claim 10, wherein the polycytidylic acid and polyinosinic acid have a molecular weight that is greater than 23,000 Daltons;
   optionally, the molecular weight of the polycytidysic acid is in a range from 66,000 Daltons~660,000 Daltons;
   optionally, the molecular weight of the polyinosinic acid is in a range from 66,000 Daltons~660,000 Daltons.

12. The method according to claim 10, wherein the base pairing reaction is carried out at pH=6.8~7.6.

13. The method according to claim 1, wherein
   before contacting, the polyinosinic-polycytidylic acid is heated at 88° C.~92° C. for 70 min~120 min.

14. The method according to claim 1, wherein the liquid reaction system is at a temperature of 40° C.~50° C.

15. The method according to claim 1, wherein a method for preparing the graft comprises:
   firstly, activating one or more of methoxypolyethylene glycol, polyethylene glycol, polyethylenimine, folic acid and galactose using carbonyl diimidazole, and then grafting an activated product with the water-soluble non-antibiotic amino compound in ionic liquid [bmim] Cl;
   optionally, the graft is a graft of chitosan oligosaccharide and methoxypolyethylene glycol, firstly activating methoxypolyethylene glycol (MPEG) using carbonyl diimidazole (CDI), and then grafting an activated MPEG with the chitosan oligosaccharide (COS) in ionic liquid [bmim] Cl;
   optionally, the grafting is performed at 60° C.~80° C. under a non-oxidizing atmosphere.

16. A method for
   adding a cross-linking agent solution dropwise to an obtained complex while stirring until Tyndall effect appears in the reaction system, and then stirring to obtain nanoparticles;
   the cross-linking agent is at least one selected from the group consisting of sodium tripolyphosphate, sodium alginate, phenylboronic acid, and catechol;
   optionally, the cross-linking agent solution further comprises one or more of an immune cell therapy drug, an antibody therapy drug, a chemical drug, a substance that promotes mucosal immune absorption or mucosal adhesion, an immunomodulator, an antigen, a pattern recognition receptor-ligand, and a pharmaceutically acceptable salt or excipient;
   optionally, the method further comprises: co-incubating the complex or the nanoparticles with one or more of the immune cell therapy drug, the antibody therapy drug, the chemical drug, the substance that promote mucosal immune absorption or mucosal adhesion, the immunomodulator, the antigen, the pattern recognition receptor-ligand, and the pharmaceutically acceptable salt or excipient;
   optionally, the antigen is a protein or a polypeptide antigen;
   optionally, the antigen includes a tumor, a virus, a bacterium, a fungus or a parasite antigen;
   optionally, the tumor includes those arising from any lesions in bone, bone connection, muscle, lung, trachea, pharynx, nose, heart, spleen, artery, vein, blood, capillary, lymph node, lymphatic vessel, lymphatic fluid, oral cavity, pharynx, esophagus, stomach, duodenum, small intestine, colon, rectum, anus, appendix, liver, gallbladder, pancreas, parotid gland, sublingual gland, urinary kidney, ureter, bladder, urethra, ovary, fallopian tube, uterus, vagina, vulva, scrotum, testes, vas deferens, penis, eyes, ears, nose, tongue, skin, brain, brainstem, medulla oblongata, spinal cord, cerebro-spinal fluid, nerves, thyroid, parathyroid gland, adrenal gland, pituitary gland, pineal gland, pancreatic islet, thymus, gonad, sublingual gland, and parotid gland;
   optionally, the bacterium includes one or more of *Staphylococcus, Streptococcus, Listeria, Erysipelothrix, Renibacterium, Bacillus, Clostridium, Mycobacterium, Actinomyces, Nocardia, Corynebacterium, Rhodococcus, Bacillus anthracis*, erysipelas *bacillus, Bacillus tetani, Listeria monocytogenes, Bacillus perfringens, Bacillus* gangraenae emphysematosae, *tuberculosis, Escherichia coli, Bacterium proteus, Shigella dysente-*

*riae*, Pneumobacillus, *Bacterium burgeri, Clostridium perfringens, Haemophilus influenzae, Haemophilus parainfluenzae, Moraxella catarrhalis, Acinetobacter, Yersinia, Legionella pneumophila, Bordetella pertussis, Bordetella parapertussis, Shigella, Pasteurella, Vibrio cholerae*, and *Vibrio Parahemolyticus;* optionally, the parasite includes one or more of parasites in the digestive tract, intraluminal parasites, intrahepatic parasites, intrapulmonary parasites, brain tissue parasites, intravascular parasites, intralymphatic parasites, muscle tissue parasites, intracellular parasites, bone tissue parasites, and intraocular parasites;

optionally, the virus includes one or more of adeniviridae, arenaviridae, astroviridae, bunyaviridae, cliciviridae, flaviviridae, hepatitis delta virus, hepeviridae, mononegavirales, nidovirales, piconaviridae, orthomyxoviridae, papillomaviridae, parvoviridae, polyomaviridae, poxviridae, reoviridae, retroviridae or togaviridae;

optionally, the fungus includes one or more of *Coccidioides immitis, Coccidioides posadasii, Histoplasma capsulatum, Histoplasma duboisii, Blastomyces lobo, Paracoccidioides brasiliensis, Blastomyces dermatitis, Sporothrix schenckii, Penicillium marneffei, Candida albicans, Candida glabrata, Candida tropicalis, Candida lusitaniae, Pneumocystis carinii, Aspergillus, Exophiala jeanselmei, Fonsecaea Pedrosoi, Fonsecaea compacta*, Chromomyces *verruciformis*, Pigmentation dermatitis, *Geotrichum candidum, Pseudallescheria boydii, Cryptococcus neoformans, Trichosporon Cutaneum, Rhizopus oryzae, Mucor indicus, Absidia corymbifera, Syncephalastrum racemosum, Basidiobolus ranarum, Conidiobolus coronatus, Conidiobolus incongruus, Enterocytozoon bieneusi, Encephalitozoon intestinalis, Rhinosporidium seeberi*, hyalohyphomycet, and phaeohyphomycete, optionally, the immune cell therapy drug is one or more selected from the group consisting of tumor infiltrating lymphocytes, dendritic cells, cytokine induced killer cells, dendritic cells-cytokine induced killer cells, natural killer cells, γδT cells, CD3AK, CAR-T and TCR-T;

optionally, the antibody therapeutic drug is selected from the group consisting of an anti-PD1 antibody, an anti-PDL1 antibody, an anti-CTLA4 antibody and an anti-CD antigen antibody;

optionally, the chemical drug is one or more selected from the group consisting of an alkylating agent, an antimetabolity, an antitumor antibiotic, a plant antitumor drug, a hormone drug and a miscellaneous drug;

wherein the miscellaneous drug is selected from the group consisting of L-asparaginase, cisplatin, carboplatin, oxaliplatin, dacarbazine, hexamethylmelamine drugs, and derivatives thereof;

optionally, the substance that promotes mucosal immune absorption or mucosal adhesion is one or more selected from the group consisting of anionic surfactants, cationic surfactants, zwitterionic surfactants, nonionic surfactants, special surfactants, chelating agents, adhesives, polylactic acid-glycolic acid copolymers, dextrans, and polysaccharides;

optionally, the immunomodulator is one or more selected from the group consisting of cytokines, chemokines, stem cell growth factors, lymphotoxins, hematopoietic factors, colony stimulating factors (CSFs), interferons, erythropoietins, thrombopoietins, tumor necrosis factors (TNFs), interleukins (ILs), granulocyte-colony stimulating factors (G-CSFs), granulocyte macrophage-colony stimulating factors (GM-CSFs) and stem cell growth factors;

optionally, the pattern recognition receptor-ligand is selected from the group consisting of a TLR receptor-ligand, a RLR receptor-ligand, a CLR receptor-ligand, and a NLR receptor-ligand.

17. A complex for potentiating an immune response prepared according to the method of claim 1.

18. A method for promoting an in vivo immune response in a host to an antigen, regulating and potentiating immune cell activity in a host, helping a host to reduce fatigue, or alleviating pain in a host, comprising administrating to the host the complex for potentiating an immune response prepared according to the method of claim 1, or a vaccine composition comprising the complex for potentiating an immune response prepared according to the method of claim 1 and at least a antigen, or a pharmaceutical composition comprising the complex for potentiating an immune response prepared according to the method of claim 1, wherein the pharmaceutical composition further comprises one or more of an immune cell therapy drug, an antibody therapy drug, a chemical drug, a substance that promotes mucosal immune absorption or mucosal adhesion, an immunomodulator, a pathogenic antigen, a pattern recognition receptor-ligand, and a pharmaceutically acceptable excipient.

\* \* \* \* \*